(12) United States Patent
Walker et al.

(10) Patent No.: US 9,693,813 B2
(45) Date of Patent: *Jul. 4, 2017

(54) SKELETAL MANIPULATION METHOD

(71) Applicant: NuVasive Specialized Orthopedics, Inc., San Diego, CA (US)

(72) Inventors: Blair Walker, Mission Viejo, CA (US); Scott Pool, Laguna Hills, CA (US); Jay R. McCoy, Temecula, CA (US); Arvin Chang, Yorba Linda, CA (US)

(73) Assignee: NuVasive Specialized Orthopedics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/880,980

(22) Filed: Oct. 12, 2015

(65) Prior Publication Data

US 2016/0030089 A1    Feb. 4, 2016

Related U.S. Application Data

(63) Continuation of application No. 14/629,426, filed on Feb. 23, 2015, now Pat. No. 9,179,960, which is a (Continued)

(51) Int. Cl.
*A61B 17/70* (2006.01)
*A61B 17/88* (2006.01)
(Continued)

(52) U.S. Cl.
CPC .......... *A61B 17/8866* (2013.01); *A61B 17/68* (2013.01); *A61B 17/707* (2013.01);
(Continued)

(58) Field of Classification Search
CPC .............. A61B 17/7016; A61B 17/707; A61B 17/7216; A61B 17/68; A61B 17/88;
(Continued)

(56) References Cited

U.S. PATENT DOCUMENTS

| 2,702,031 A | 2/1955 | Wenger |
| 3,810,259 A | 5/1974 | Summers |

(Continued)

FOREIGN PATENT DOCUMENTS

| CN | 101040807 | 9/2007 |
| DE | 8515687 | 12/1985 |

(Continued)

OTHER PUBLICATIONS

Hennig, A., Incavo, S., Beynnon, B., Abate, J., Urse, J., Kelly, S. "The Safety and Efficiency of a New Adjustable Plate Used for Proximal Tibial Opening Wedge Osteotomy in the Treatment of Unicompartmental Knee Osteoarthritis", Journal of Knee Surgery, 2007, vol. 20, No. 1, pp. 6-14, Thieme Medical Publishers, New York, United States.

(Continued)

*Primary Examiner* — Pedro Philogene
(74) *Attorney, Agent, or Firm* — Jeremy A. Smith; Bradley Arant Boult Cummings LLP

(57) ABSTRACT

A method of treating scoliosis in a subject includes securing a scoliosis treatment device to first and second locations on the subject's skeletal system, the scoliosis treatment device including a first portion, a second portion moveably mounted relative to the first portion, and an adjustment device disposed on the device and configured to change a distraction force between the first location and the second location, the adjustment device including a rotationally mounted magnetic element configured to move the second portion relative to the first portion in response to rotation of the magnetic element. An external adjustment device is provided external to the subject and is able to adjust the distraction force between the first location and second location.

38 Claims, 44 Drawing Sheets

Related U.S. Application Data continuation of application No. 13/849,405, filed on Mar. 22, 2013, now Pat. No. 9,271,781, which is a continuation of application No. 13/277,980, filed on Oct. 20, 2011, now Pat. No. 8,419,734, which is a continuation of application No. 12/121,499, filed on May 15, 2008, now Pat. No. 8,057,472.

(60) Provisional application No. 60/983,917, filed on Oct. 30, 2007.

(51) Int. Cl.
| | | |
|---|---|---|
| *A61B 17/72* | (2006.01) | |
| *A61B 17/80* | (2006.01) | |
| *A61B 17/68* | (2006.01) | |
| *A61B 17/00* | (2006.01) | |
| *A61B 17/56* | (2006.01) | |

(52) U.S. Cl.
CPC ...... *A61B 17/7016* (2013.01); *A61B 17/7216* (2013.01); *A61B 17/8004* (2013.01); *A61B 17/88* (2013.01); *A61B 17/7044* (2013.01); *A61B 17/7065* (2013.01); *A61B 17/7266* (2013.01); *A61B 2017/00411* (2013.01); *A61B 2017/00876* (2013.01); *A61B 2017/564* (2013.01); *A61B 2017/681* (2013.01)

(58) Field of Classification Search
CPC ............ A61B 17/8866; A61B 17/8004; A61B 17/7044; A61B 17/7065; A61B 17/7266; A61B 2017/681; A61B 2017/00411; A61B 2017/00876; A61B 2017/564
USPC ...................................... 606/246–279, 54–59
See application file for complete search history.

(56) References Cited

U.S. PATENT DOCUMENTS

| | | |
|---|---|---|
| 3,900,025 A | 8/1975 | Barnes, Jr. |
| 3,976,060 A | 8/1976 | Hildebrandt et al. |
| 4,078,559 A | 3/1978 | Nissinen |
| 4,448,191 A | 5/1984 | Rodnyansky et al. |
| 4,522,501 A | 6/1985 | Shannon |
| 4,537,520 A | 8/1985 | Ochiai et al. |
| 4,573,454 A | 3/1986 | Hoffman |
| 4,658,809 A | 4/1987 | Ulrich |
| 4,854,304 A | 8/1989 | Zielke |
| 4,973,331 A | 11/1990 | Pursley et al. |
| 5,010,879 A | 4/1991 | Moriya et al. |
| 5,030,235 A | 7/1991 | Campbell, Jr. |
| 5,074,882 A | 12/1991 | Grammont et al. |
| 5,092,889 A | 3/1992 | Campbell, Jr. |
| 5,261,908 A | 11/1993 | Campbell, Jr. |
| 5,263,955 A | 11/1993 | Baumgart et al. |
| 5,290,289 A | 3/1994 | Sanders et al. |
| 5,336,223 A | 8/1994 | Rogers |
| 5,364,396 A | 11/1994 | Robinson et al. |
| 5,466,261 A | 11/1995 | Richelsoph |
| 5,527,309 A | 6/1996 | Shelton |
| 5,575,790 A | 11/1996 | Chen et al. |
| 5,626,579 A | 5/1997 | Muschler et al. |
| 5,632,744 A | 5/1997 | Campbell, Jr. |
| 5,672,175 A | 9/1997 | Martin |
| 5,672,177 A | 9/1997 | Seldin |
| 5,700,263 A | 12/1997 | Schendel |
| 5,704,939 A | 1/1998 | Justin |
| 5,720,746 A | 2/1998 | Soubeiran |
| 5,762,599 A | 6/1998 | Sohn |
| 5,800,434 A | 9/1998 | Campbell, Jr. |
| 5,827,286 A | 10/1998 | Incavo et al. |
| 5,902,304 A | 5/1999 | Walker et al. |
| 5,961,553 A | 10/1999 | Coty et al. |
| 6,033,412 A | 3/2000 | Losken et al. |
| 6,074,882 A | 6/2000 | Eckardt |
| 6,106,525 A | 8/2000 | Sachse |
| 6,162,223 A | 12/2000 | Orsak |
| 6,183,476 B1 | 2/2001 | Gerhardt et al. |
| 6,200,317 B1 | 3/2001 | Aalsma et al. |
| 6,336,929 B1 | 1/2002 | Justin |
| 6,358,283 B1 | 3/2002 | Hogfors et al. |
| 6,375,682 B1 | 4/2002 | Fleischmann et al. |
| 6,416,516 B1 | 7/2002 | Stauch et al. |
| 6,417,750 B1 | 7/2002 | Sohn |
| 6,510,345 B1 | 1/2003 | Van Bentem |
| 6,537,196 B1 | 3/2003 | Creighton, IV et al. |
| 6,554,831 B1 | 4/2003 | Rivard et al. |
| 6,565,576 B1 | 5/2003 | Stauch et al. |
| 6,657,351 B2 | 12/2003 | Chen et al. |
| 6,706,042 B2 | 3/2004 | Taylor |
| 6,765,330 B2 | 7/2004 | Baur |
| 6,796,984 B2 | 9/2004 | Soubeiran |
| 6,835,207 B2 | 12/2004 | Zacouto et al. |
| 6,849,076 B2 | 2/2005 | Blunn et al. |
| 6,918,910 B2 | 7/2005 | Smith et al. |
| 6,971,143 B2 | 12/2005 | Domroese |
| 7,029,472 B1 | 4/2006 | Fortin |
| 7,063,706 B2 | 6/2006 | Wittenstein |
| 7,135,022 B2 | 11/2006 | Kosashvili et al. |
| 7,357,635 B2 | 4/2008 | Belfor et al. |
| 7,441,559 B2 | 10/2008 | Nelson et al. |
| 7,458,981 B2 | 12/2008 | Fielding |
| 7,481,841 B2 | 1/2009 | Hazebrouck et al. |
| 7,485,149 B1 | 2/2009 | White |
| 7,531,002 B2 | 5/2009 | Sutton et al. |
| 7,601,156 B2 | 10/2009 | Robinson |
| 7,611,526 B2 | 11/2009 | Carl et al. |
| 7,666,184 B2 | 2/2010 | Stauch |
| 7,753,915 B1 | 7/2010 | Eksler et al. |
| 7,776,091 B2 | 8/2010 | Mastrorio et al. |
| 7,794,476 B2 | 9/2010 | Wisnewski |
| 7,811,328 B2 | 10/2010 | Molz, IV et al. |
| 7,887,566 B2 | 2/2011 | Hynes |
| 8,016,837 B2 | 9/2011 | Giger et al. |
| 8,043,299 B2 | 10/2011 | Conway |
| 8,057,472 B2 * | 11/2011 | Walker ............... A61B 17/7016 128/898 |
| 8,105,360 B1 | 1/2012 | Connor |
| 8,105,363 B2 | 1/2012 | Fielding et al. |
| 8,147,517 B2 | 4/2012 | Trieu et al. |
| 8,177,789 B2 | 5/2012 | Magill et al. |
| 8,211,179 B2 | 7/2012 | Molz, IV et al. |
| 8,216,275 B2 | 7/2012 | Fielding et al. |
| 8,298,240 B2 | 10/2012 | Giger et al. |
| 8,419,734 B2 * | 4/2013 | Walker ............... A61B 17/7016 606/57 |
| 8,419,801 B2 | 4/2013 | DiSilvestro et al. |
| 8,439,915 B2 | 5/2013 | Harrison et al. |
| 8,469,908 B2 | 6/2013 | Asfora |
| 8,486,110 B2 | 7/2013 | Fielding et al. |
| 8,568,457 B2 * | 10/2013 | Hunziker ........... A61B 17/7016 606/246 |
| 8,894,663 B2 | 11/2014 | Giger et al. |
| 9,179,960 B2 * | 11/2015 | Walker ............... A61B 17/7016 |
| 2002/0050112 A1 | 5/2002 | Koch et al. |
| 2002/0188296 A1 | 12/2002 | Michelson |
| 2003/0144669 A1 | 7/2003 | Robinson |
| 2004/0023623 A1 | 2/2004 | Stauch et al. |
| 2004/0138663 A1 | 7/2004 | Kosashvili et al. |
| 2004/0193266 A1 | 9/2004 | Meyer |
| 2005/0004417 A1 | 1/2005 | Nelson et al. |
| 2005/0055025 A1 | 3/2005 | Zacouto et al. |
| 2005/0080427 A1 | 4/2005 | Govari et al. |
| 2005/0090823 A1 | 4/2005 | Bartim |
| 2005/0107787 A1 | 5/2005 | Kutsenko |
| 2005/0113831 A1 | 5/2005 | Franck et al. |
| 2005/0159637 A9 | 7/2005 | Nelson et al. |
| 2005/0159754 A1 | 7/2005 | Odrich |
| 2005/0234448 A1 | 10/2005 | McCarthy |
| 2005/0246034 A1 * | 11/2005 | Soubeiran .......... A61B 17/7216 623/23.45 |
| 2005/0251109 A1 | 11/2005 | Soubeiran |
| 2005/0261779 A1 | 11/2005 | Meyer |

(56) References Cited

U.S. PATENT DOCUMENTS

| | | |
|---|---|---|
| 2006/0004447 A1 | 1/2006 | Mastrorio et al. |
| 2006/0004459 A1 | 1/2006 | Hazebrouck et al. |
| 2006/0009767 A1 | 1/2006 | Kiester |
| 2006/0015118 A1 | 1/2006 | Richter et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1* | 3/2006 | Gordon ............ A61B 17/7016 606/86 A |
| 2006/0052782 A1 | 3/2006 | Morgan et al. |
| 2006/0058792 A1 | 3/2006 | Hynes |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0085043 A1 | 4/2006 | Stevenson |
| 2006/0136062 A1 | 6/2006 | DiNelio et al. |
| 2006/0142767 A1 | 6/2006 | Green et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0200134 A1 | 9/2006 | Freid et al. |
| 2006/0204156 A1 | 9/2006 | Takehara et al. |
| 2006/0235424 A1 | 10/2006 | Vitale et al. |
| 2006/0271107 A1 | 11/2006 | Harrison et al. |
| 2006/0293683 A1 | 12/2006 | Stauch |
| 2007/0010814 A1 | 1/2007 | Stauch |
| 2007/0010887 A1 | 1/2007 | Williams et al. |
| 2007/0016202 A1 | 1/2007 | Kraft et al. |
| 2007/0043376 A1 | 2/2007 | Leatherbury et al. |
| 2007/0050030 A1 | 3/2007 | Kim |
| 2007/0173837 A1 | 7/2007 | Chan et al. |
| 2007/0179493 A1 | 8/2007 | Kim |
| 2007/0191846 A1 | 8/2007 | Bruneau et al. |
| 2007/0213751 A1 | 9/2007 | Scirica et al. |
| 2007/0233098 A1 | 10/2007 | Mastrorio et al. |
| 2007/0239159 A1 | 10/2007 | Altarac et al. |
| 2007/0239161 A1 | 10/2007 | Giger et al. |
| 2007/0244488 A1 | 10/2007 | Metzger et al. |
| 2007/0255088 A1 | 11/2007 | Jacobson et al. |
| 2007/0255273 A1 | 11/2007 | Fernandez et al. |
| 2007/0264605 A1 | 11/2007 | Belfor et al. |
| 2007/0270803 A1* | 11/2007 | Giger ................ A61B 17/8076 606/60 |
| 2007/0276368 A1 | 11/2007 | Trieu et al. |
| 2007/0276369 A1 | 11/2007 | Allard et al. |
| 2007/0276378 A1 | 11/2007 | Harrison et al. |
| 2007/0288024 A1 | 12/2007 | Gollogly |
| 2008/0027436 A1 | 1/2008 | Cournoyer et al. |
| 2008/0033436 A1 | 2/2008 | Song et al. |
| 2008/0048855 A1 | 2/2008 | Berger |
| 2008/0065181 A1 | 3/2008 | Stevenson |
| 2008/0161933 A1 | 7/2008 | Grotz et al. |
| 2008/0167685 A1 | 7/2008 | Allard et al. |
| 2008/0177319 A1 | 7/2008 | Schwab |
| 2008/0177326 A1 | 7/2008 | Thompson |
| 2008/0228186 A1 | 9/2008 | Gall et al. |
| 2008/0234681 A1 | 9/2008 | Baynham |
| 2008/0255615 A1 | 10/2008 | Vittur et al. |
| 2008/0272928 A1 | 11/2008 | Shuster et al. |
| 2009/0030462 A1 | 1/2009 | Buttermann |
| 2009/0048618 A1* | 2/2009 | Harrison ............ A61B 17/0483 606/153 |
| 2009/0076597 A1 | 3/2009 | Dahlgren et al. |
| 2009/0082690 A1 | 3/2009 | Philips et al. |
| 2009/0088766 A1 | 4/2009 | Magill et al. |
| 2009/0093820 A1 | 4/2009 | Trieu et al. |
| 2009/0093890 A1 | 4/2009 | Gelbart |
| 2009/0105766 A1 | 4/2009 | Thompson et al. |
| 2009/0192514 A1 | 7/2009 | Feinberg et al. |
| 2009/0204156 A1 | 8/2009 | McClintock et al. |
| 2010/0049204 A1* | 2/2010 | Soubeiran ............ A61B 17/025 606/90 |
| 2010/0228167 A1 | 9/2010 | Ilovich et al. |
| 2010/0249847 A1 | 9/2010 | Jung et al. |
| 2011/0004076 A1 | 1/2011 | Janna et al. |
| 2012/0203282 A1 | 8/2012 | Sachs et al. |
| 2013/0296859 A1 | 11/2013 | Walker et al. |
| 2014/0163664 A1 | 6/2014 | Goldsmith |
| 2015/0105824 A1 | 4/2015 | Moskowitz et al. |
| 2015/0173820 A1 | 6/2015 | Walker et al. |

FOREIGN PATENT DOCUMENTS

| | | |
|---|---|---|
| DE | 102005045070 | 4/2007 |
| EP | 1905388 | 4/2008 |
| FR | 2900563 | 11/2007 |
| FR | 2901991 | 12/2007 |
| JP | 05-104022 | 4/1993 |
| JP | 2007-050339 | 3/2007 |
| WO | WO 99/51160 | 10/1999 |
| WO | WO 2006/090380 | 8/2006 |
| WO | WO 2007/015239 | 2/2007 |
| WO | WO 2007/025191 | 3/2007 |
| WO | WO 2007/118179 | 10/2007 |
| WO | WO 2007/144489 | 12/2007 |
| WO | WO 2008/003952 | 1/2008 |
| WO | WO 2008/040880 | 4/2008 |
| WO | WO 2009/058546 | 5/2009 |

OTHER PUBLICATIONS

Dorsey, W., Miller, B., Tadje, J., Bryant, C. "The Stability of Three Commercially Available Implants Used in Medial Opening Wedge High Tibial Osteotomy", Journal of Knee Surgery, 2006, vol. 19. No. 2, pp. 95-98, Thieme Medical Publishers, New York, United States.

International Preliminary Report on Patentability dated Apr. 28, 2011, for PCT/US2009/060266, filed Oct. 9, 2009, Applicant: Ellipse Technologies, Inc. et al., Forms PCT/IB/373 and PCT/ISA/237 (8 pages).

PCT International Preliminary Report on Patentability (Chapter I of the Patent Cooperation Treaty) for PCT/US2008/079743, Applicant: Ellipse Technologies, Inc., Form PCT/IB/326 and 373, dated May 14, 2010 (13 pages).

PCT International Search Report for PCT/US2009/060266, Applicant: Ellipse Technologies, Inc., Form PCT/ISAI210 and 220, dated Dec. 10, 2009 (4 pages).

PCT Written Opinion of the International Search Authority for PCT/US2009/060266, Applicant: Ellipse Technologies, Inc., Form PCT/ISA/237, dated Dec. 10, 2009 (5 pages).

PCT International Search Report and Written Opinion for PCT/US08/79743, Applicant Ellipse Technologies, Inc., Forms PCT/ISA/210, 220, and 237 dated Dec. 12, 2008 (17 pages).

Tello C., "Harrington Instrumentation without Arthrodesis and Consecutive Distraction Program for Young Children with Sever Spinal Deformities: Experience and Technical Details", Orthopedic Clinics of North America, vol. 25, No. 2 1994. pp. 333-351. (19 pages).

Guichet, J., Deromedis, B., Donnan, L., Peretti, G., Lascombes, P., Bado,F., "Gradual Femoral Lengthening with the Albizzia Intramedullary Nail", Journal of Bone and Joint Surgery American Edition, 2003, vol. 85, pp. 838-848, (12 pages).

Marco Teli, M.D. et al. Measurement of Forces Generated During Distraction of Growing Rods. Marco Teli, J. Child Orthop (2007) 1:257-258.

Hazem Elsebaie M.D., Single Growing Rods (Review of 21 cases). Changing the Foundations: Does it affect the Results?, J Child Orthop. (2007) 1:258.

Abe, J., Nagata, K., Ariyoshi, M., Inoue, A., "Experimental External Fixation Combined with Pecutaneous Discectomy in the Management of Scoliosis", Spine, 1999, vol. 24, No. 7, pp. 646-653, Lippincott Co., Philadelphia, U.S.A.

Buchowski, J., Bhatnagar, R., Skaggs, D., Sponseller, P., "Temporary Internal Distraction as an Aid to Correction of Severe Scoliosis", Journal of Bone and Joint Surgery American Edition, 2006, vol. 88A, No. 9, pp. 2035-2041.

Buchowski, J., Skaggs, D., Sponseller, P., Temporary Internal Distraction as an Aid to Correction of Severe Scoliosis. Surgical

(56) References Cited

OTHER PUBLICATIONS

Technique, Journal of Bone and Joint Surgery American Edition, 2007, vol. 89A No. Supp 2 (pt. 2), pp. 297-309, Journal of Bone and Joint Surgery, Boston, U.S.A.

Burke, J. "Design of a Minimally Invasive Non Fusion Device for the Surgical Management of Scoliosis in the Skeletally Immature", Studies in Health Technology and Informatics, 2006, vol. 123. pp. 378-384, IOS Press, Amsterdam, The Netherlands.

Daniels, A., Gemperline, P., Grahn, A., Dunn, H., "A New Method for Continuous Intraoperative Measurement of Harrington Rod Loading Patterns", Annals of Biomedical Engineering, 1984, vol. 12, No. 3, pp. 233-246, Dordrecht Kluwer Academic/Plenum Publishers, New York, U.S.A.

Edelan, H., Eriksson, G., Dahlberg, E., "Instrument for distraction by limited surgery in scoliosis treatment", Journal of Biomedical Engineering, 1981, vol. 3, No. 2, pp. 143-146, Butterfield Scientific Limited, Guilford, England.

Ember, T., Noordeen, H., "Distraction forces required during growth rod lengthening", Journal of Bone and Joint Surgery British Edition, 2006, vol. 88B, No. Supp II, p. 229, Churchill Livingstone, London, England.

Gao et al., CHD7 Gene Polymorph isms Are Associated with Susceptibility to Idiopathic Scoliosis, American Journal of Human Genetics, vol. 80, pp. 957-965 (May 2007).

Gebhart, M., Neel, M., Soubeiran, A., Dubousset, J., "Early clinical experience with a custom made growing endoprosthesis in children with malignant bone tumors of the lower extremity actioned by an external permanent magnet: the Phenix M system", International Society of Limb Salvage 14th International Symposium on Limb Salvage, Sep. 13, 2007, Hamburg, Germany.

Gillespie, R., O'Brien, J., "Harrington Instrumentation without Fusion", The Journal of Bone and Joint Surgery British Edition, 1981, vol. 63B, No. 3, p. 461, Churchill Livingstone, London, England.

Grass, P., Soto, A., Araya, H., "Intermittent Distracting Rod for Correction of High Neurologic Risk Congenital Scoliosis", Spine, 1997, vol. 22, No. 16, pp. 1922-1927, Lippincott Co., Philadelphia, U.S.A.

Grimer, R., Chotel, F., Abudu, S., Tillman, R., Carter, S., "Non-invasive extendable endoprosthesis for children—expensive but worth it", International Society of Limb Salvage 14th International Symposium on Limb Salvage, Sep. 13, 2007, Hamburg, Germany.

Gupta, A., Meswania, J., Pollock, R., Cannon, S., Briggs, T., Taylor, S., Blunn, G., "Non-Invasive Distal Femoral Expandable Endoprosthesis for Limb-Salvage Surgery in Paediatric Tumours", The Journal of Bone and Joint Surgery British Edition, 2006, vol. 88-B, No. 5, pp. 649-654, Churchill Livingstone, London, England.

Hankemeier, S., Gosling, T., Pape, H., Wiebking, U., Krettek, C., "Limb Lengthening with the Intramedullary Skeletal Kinetic Distractor (ISKD)", Operative Orthopadie und Traumatologie, 2005, vol. 17, No. 1, pp. 79-101, Urban & Vogel, Munich, Germany.

Harrington, P., "Treatment of Scoliosis: Correction and Internal Fixation by Spine Instrumentation", The Journal of Bone and Joint Surgery American Edition, 1962, vol. 44A, No. 4, pp. 591-610, Journal of Bone and Joint Surgery. Boston, U.S.A.

Klemme, W., Denis, F., Winter, R., Lonstein, J., Koop, S., "Spinal Instrumentation without Fusion for Progressive Scoliosis in Young Children", Journal of Pediatric Orthopedics. 1997, vol. 17, No. 6, pp. 734-742, Raven Press, New York, U.S.A.

Lonner, B., "Emerging minimally invasive technologies for the management of scoliosis", Orthopedic Clinics of North America, 2007; vol. 38, No. 3, pp. 431-440, Saunders, Philadelphia, U.S.A.

Mineiro, J., Weinstein, S., "Subcutaneous Rodding for Progressive Spinal Curvatures: Early Results", Journal of Pediatric Orthopedics, 2002, vol. 22, No. 3, pp. 290-295, Raven Press, New York, U.S.A.

Moe, J., Kharrat, K., Winter, R., Cummine, J., "Harrington Instrumentation without Fusion Plus External Orthotic Support for the Treatment of Difficult Curvature Problems in Young Children", Clinical Orthopaedics and Related Research, 1984, No. 185. pp. 35-45, Lippincott Co., Philadelphia, U.S.A.

Nachemson, A., Elfstrom, G., "Intravital Wireless Telemetry of Axial Forces in Harrington Distraction Rods in Patients with Idiopathic Scoliosis", The Journal of Bone and Joint Surgery American Edition, 1971, vol. 53A, No. 3, pp. 445-465, Journal of Bone and Joint Surgery, Boston, U.S.A.

Nachlas, I., Borden, J., "The cure of experimental scoliosis by directed growth control". The Journal of Bone and Joint Surgery American Edition, 1951, vol. 33, No. A:1, pp. 24-34, Journal of Bone and Joint Surgery, Boston, U.S.A.

Newton, P., "Fusion less Scoliosis Correction by Anterolateral Tethering _,_Can it Work?", 39th Annual Scoliosis Research Society Meeting, Sep. 6, 2004, Buenos Aires, Argentina (transcript and slides supplied).

Rathjen, K., Wood, M., McClung, A., Vest, Z., "Clinical and Radiographic Results after Implant Removal in Idiopathic Scoliosis", Spine, 2007, vol. 32, No. 20, pp. 2184-2188, Lippincott Co., Philadelphia, U.S.A.

Reyes-Sanchez, A., Rosales, L., Miramontes, V., "External Fixation for Dynamic Correction of Severe Scoliosis", The Spine Journal, 2005, vol. 5, No. 4, pp. 418-426, Elsevier Science Inc., New York, U.S.A.

Rinsky, L., Gamble, J., Bleck, E., "Segmental Instrumentation Without fusion in Children with Progressive Scoliosis", Journal of Pediatric Orthopedics, 1985, vol. 5, No. 6, pp. 687-690, Raven Press, New York, U.S.A.

Schmerling, M., Wilkov, M., Sanders, A., "Using the Shape Recovery of Nitinol in the Harrington Rod Treatment of Scoliosis", Journal of Biomedical Materials Research, 1976, vol. 10, No. 6, pp. 879-892, Wiley, Hoboken, U.S.A.

Sharke, P., "The Machinery of Life", Mechanical Engineering Magazine, Feb. 2004, Printed from Internet site Oct. 24, 2007 http://www.memagazine.org/contents/currentlfeatures/moflife/moflife.html.

Smith J., "The Use of Growth-Sparing Instrumentation in Pediatric Spinal Deformity", Orthopedic Clinics of North America, 2007, vol. 38, No. 4, pp. 547-552, Saunders, Philadelphia, U.S.A.

Soubeiran, A., Gebhart, M., Miladi, L., Gnffet, J., Neel, M., Dubousset, J., "The Phenix M System. A Mechanical Fully Implanted Lengthening Device Externally Controllable Through the Skin with a Palm Size Permanent Magnet; Applications to Pediatric Orthopaedics", 6th European Research Conference in Pediatric Orthopaedics, Oct. 6, 2006, Toulouse, France.

Soubeiran, A., Gebhart, M., Miladi, L., Griffet, J., Neel, M., Dubousset, J., "The Phenix M system, a fully implanted non invasive lengthening device externally controllable through the skin with a palm size permanent magnet. Applications in limb salvage" International Society of Limb Salvage 14th International Symposium on Limb Salvage, Sep. 13, 2007, Hamburg, Germany.

Takaso, M., Moriya, H., Kitahara, H., Minami, S., Takahashi, K., Isobe, K., Yamagata, M., Otsuka, Y., Nakata, Y., Inoue, M., "New remote-controlled growing-rod spinal instrumentation possibly applicable for scoliosis in young children", Journal of Orthopaedic Science, 1998, vol. 3, No. 6, pp. 336-340, Springer-Verlag, Tokyo, Japan.

Thompson, G., Akbarnia, B., Campbell, R., "Growing Rod Techniques in Early-Onset Scoliosis", Journal of Pediatric Orthopedics, 2007, vol. 27, No. 3, pp. 354-361, Raven Press, New York, U.S.A.

Thompson, G., Lenke, L., Akbarnia, B., McCarthy, R., Campbell, Jr., R. "Early Onset Scoliosis: Future Directions", 2007, Journal of Bone and Joint Surgery American Edition, vol. 89A, No. Supp 1, pp. 163-166, Journal of Bone and Joint Surgery, Boston, U.S.A.

Trias, A, Bourassa, P., Massoud, M., "Dynamic Loads Experienced in Correction of Idiopathic Scoliosis Using Two Types of Harrington Rods", Spine, 1979, vol. 4, No. 3, pp. 228-235, Lippincott Co., Philadelphia, U.S.A.

Verkerke, G., Koops, H., Veth, R, Oldhoff, J., Nielsen, H., vanden Kroonenberg, H., Grootenboer, H., van Krieken, F., "Design of a Lengthening Element for a Modular Femur Endoprosthetic System", Proceedings of the Institution of Mechanical Engineers Part H: Journal of Engineering in Medicine, 1989, vol. 203, No. 2, pp. 97-102, Mechanical Engineering Publications, London, England.

Verkerke, G., Koops, H., Veth, R, van den Kroonenberg, H., Grootenboer, H., Nielsen, H., Oldhoff, J., Postma, A, "An Extend-

(56) References Cited

OTHER PUBLICATIONS able Modular Endoprosthetic System for Bone Tumour Management in the Leg", Journal of Biomedical Engineering, 1990, vol. 12, No. 2, pp. 91-96, Butterfield Scientific Limited, Guilford, England.
Verkerke, G., Koops, H., Veth, R, Grootenboer, H., De Boer, L., Oldhoff, J., Postma, A. "Development and Test of an Extendable Endoprosthesis for Bone Reconstruction in the Leg", The International Journal of Artificial Organs, 1994, vol. 17, No. 3, pp. 155-162, Wichtig Editore, Milan, Italy.
Wenger, H., "Spine Jack Operation in the Correction of Scoliotic Deformity", Archives of Surgery, 1961, vol. 83, pp. 123-132 (901-910), American Medical Association, Chicago, U.S.A.
White, A, Panjabi, M., The Clinical Biomechanics of Scoliosis, Clinical Orthopaedics and Related Research, 1976, No. 118, pp. 100-112, Lippincott Co., Philadelphia, U.S.A.
Non-Final Office Action dated Apr. 13, 2011 in U.S. Appl. No. 12/121,438, filed May 15, 2008, Applicant: Scott Pool, (29 pages).
Non-Final Office Action dated Apr. 6, 2011 in U.S. Appl. No. 12/121,355, filed May 15, 2008, Applicant: Scott Pool, (26 pages).
Japanese Office Action received Mar. 12, 2015 in Japanese Patent Application No. 2010-531128 and English translation in 8 pages.

\* cited by examiner

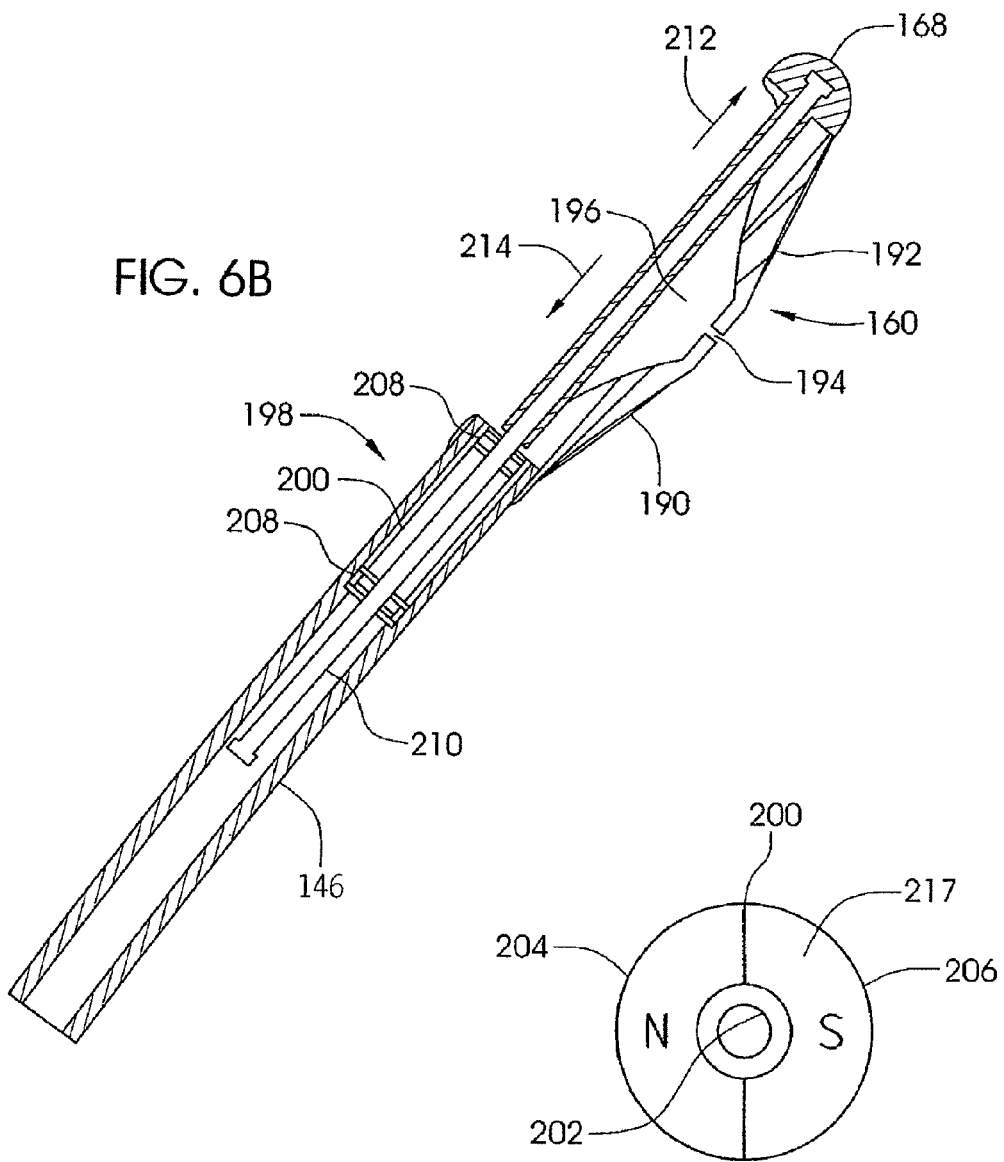

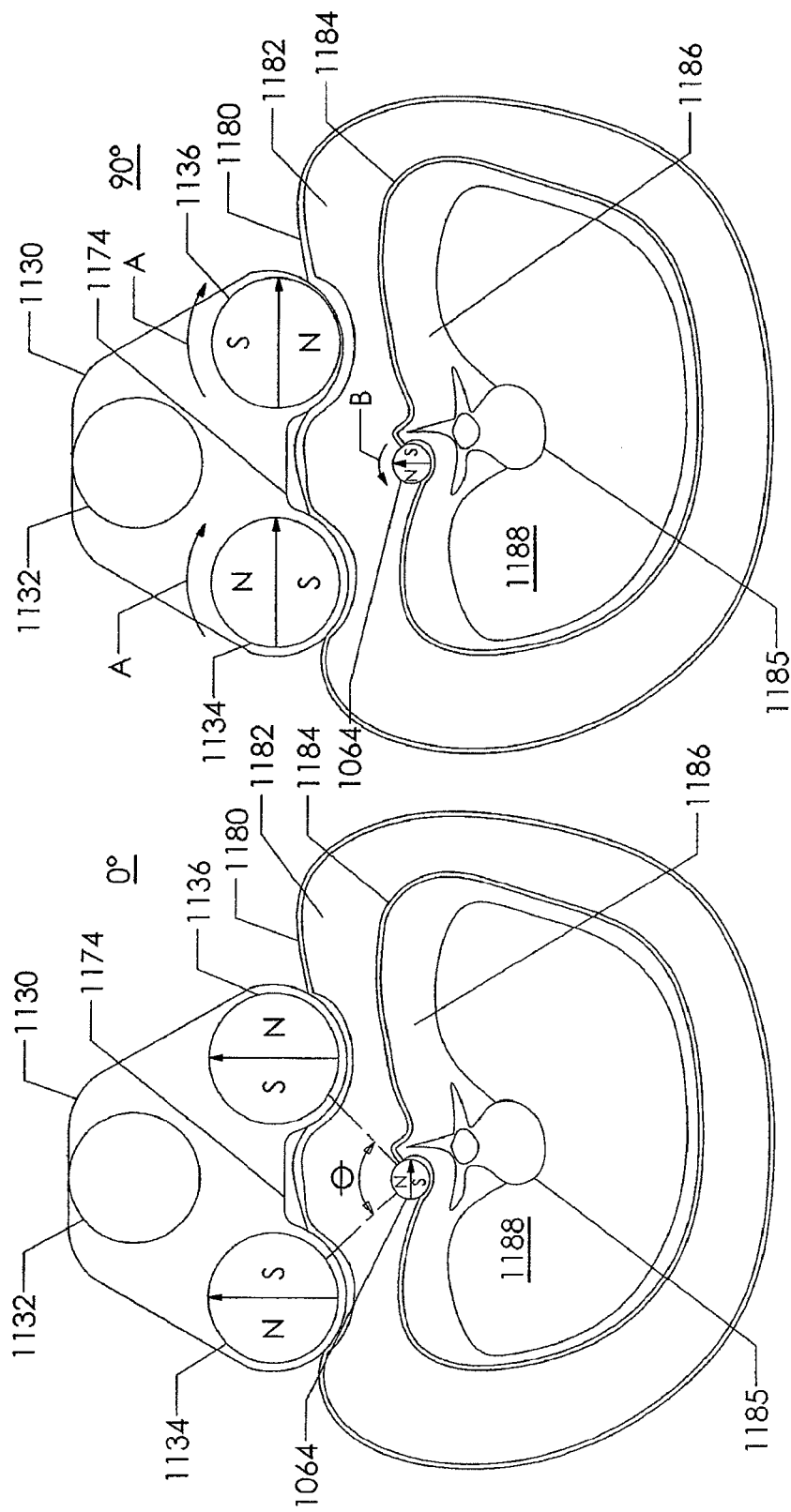

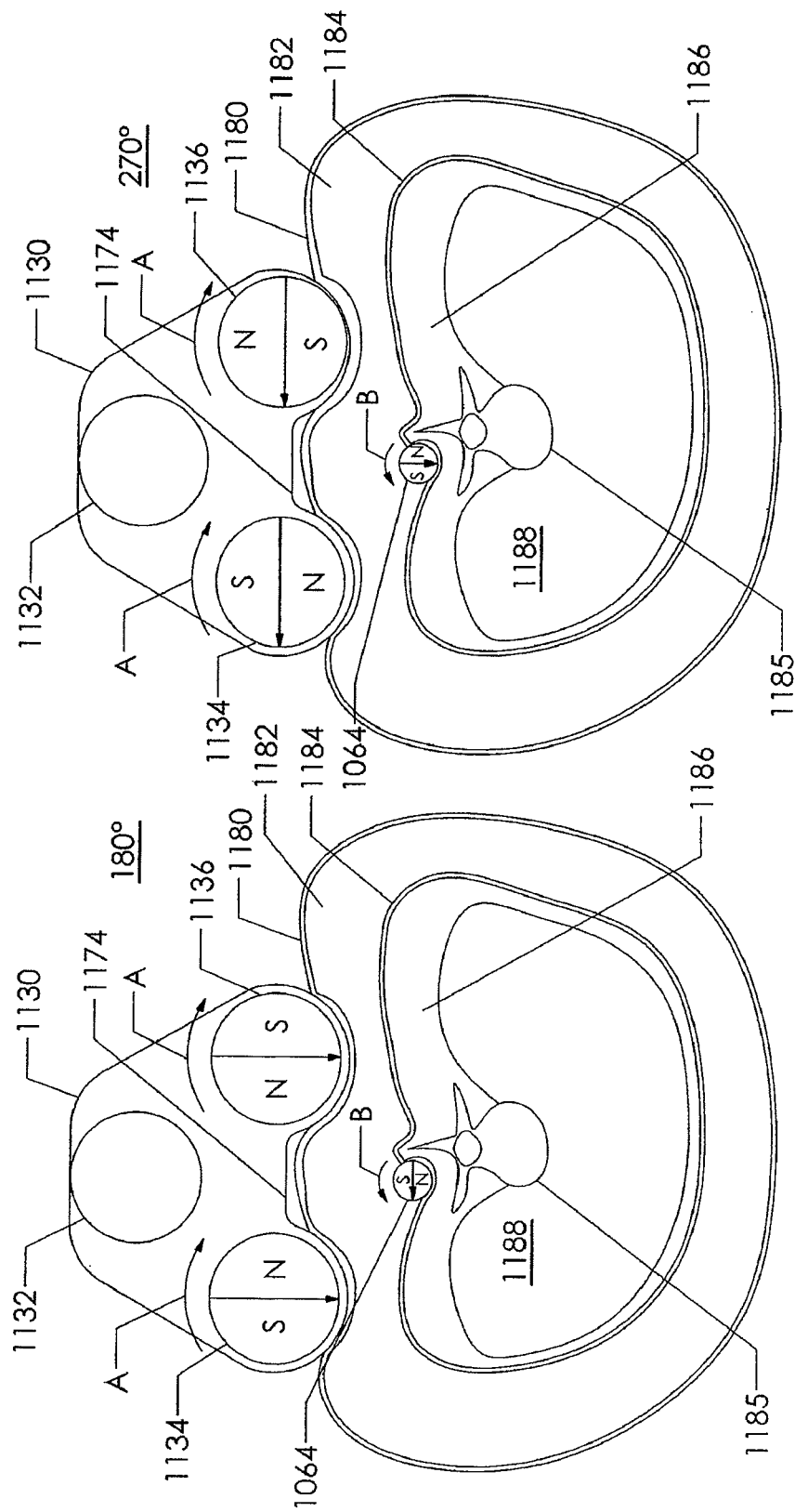

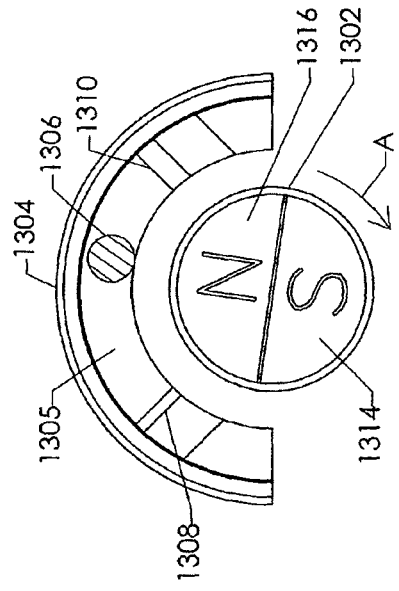
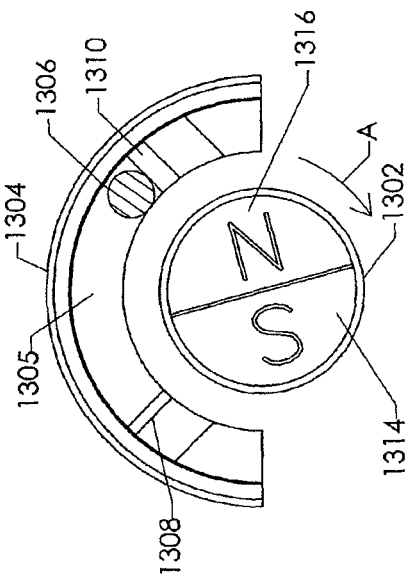
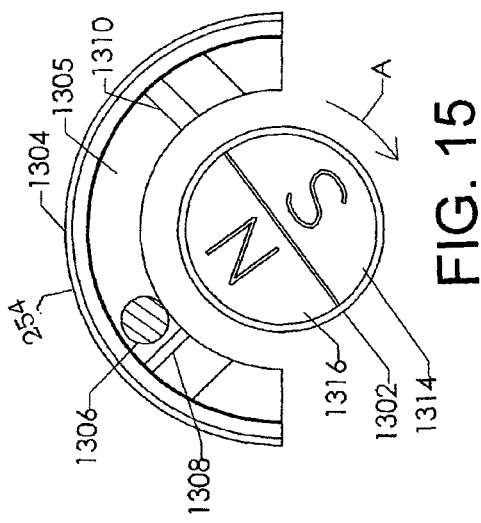
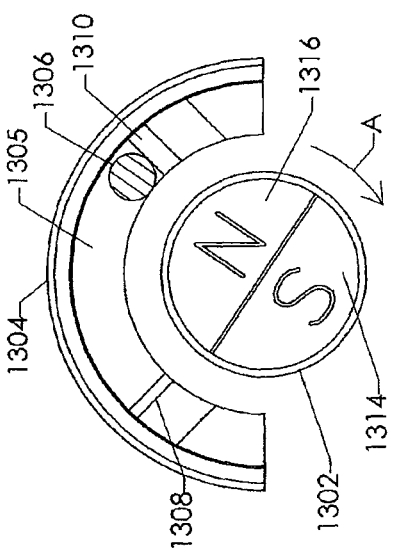
FIG. 15
FIG. 16
FIG. 17
FIG. 18

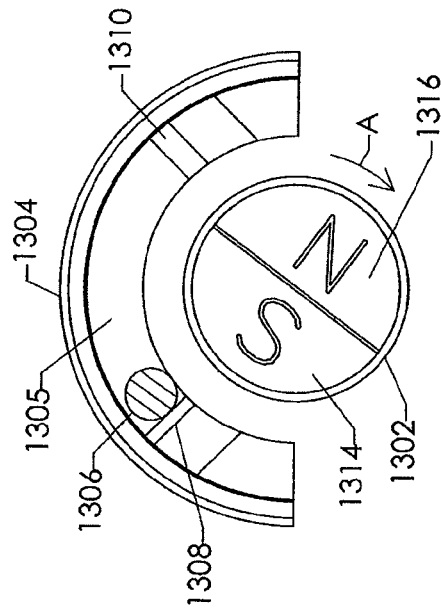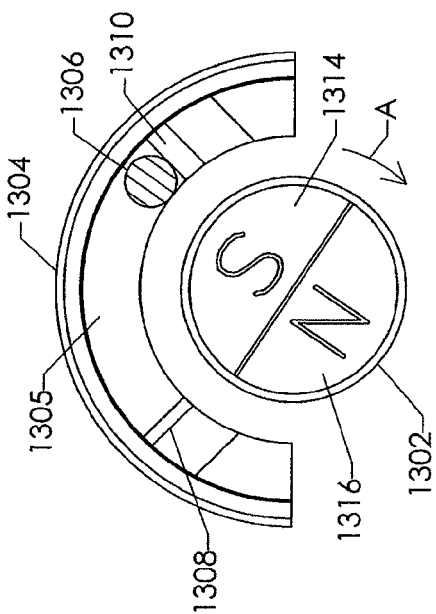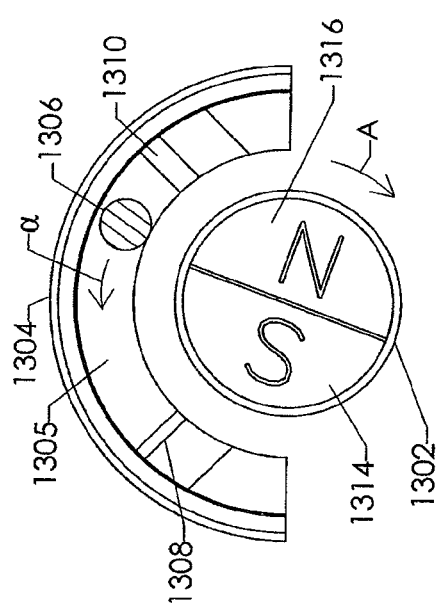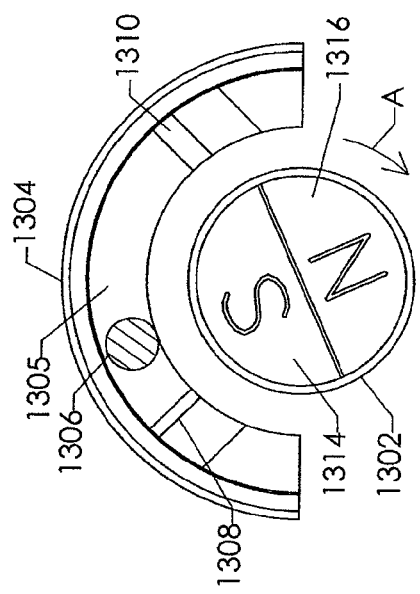
FIG. 19
FIG. 20
FIG. 21
FIG. 22

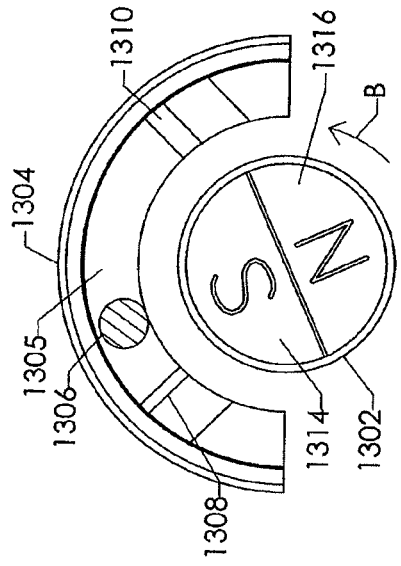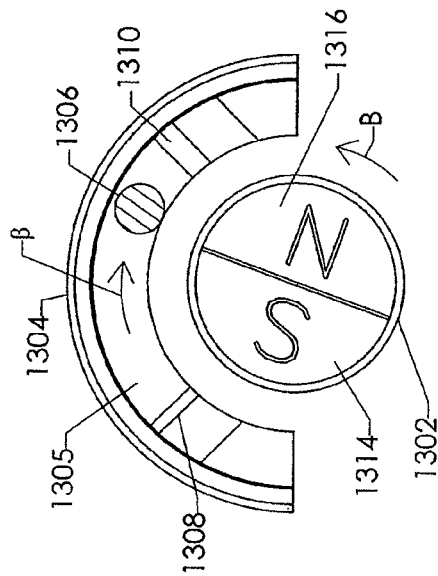
FIG. 23  FIG. 24
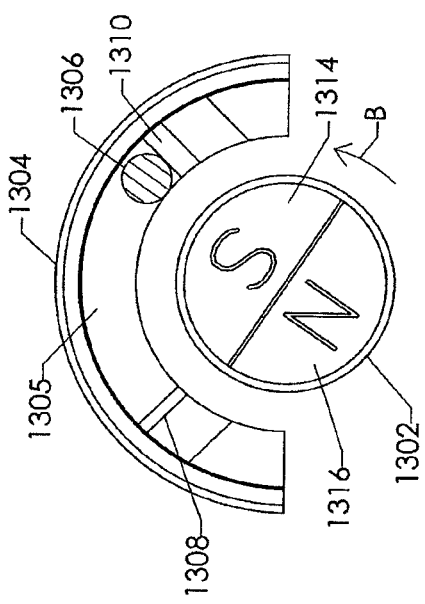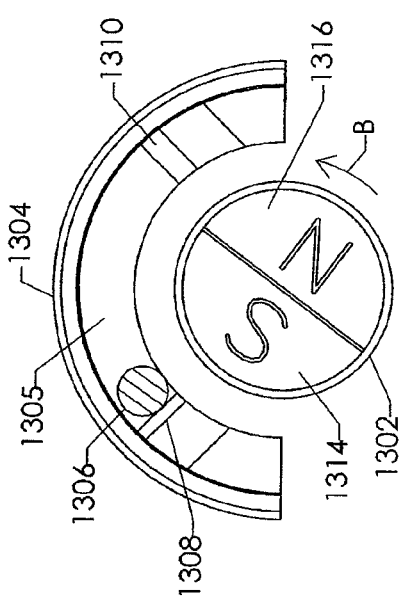
FIG. 25  FIG. 26

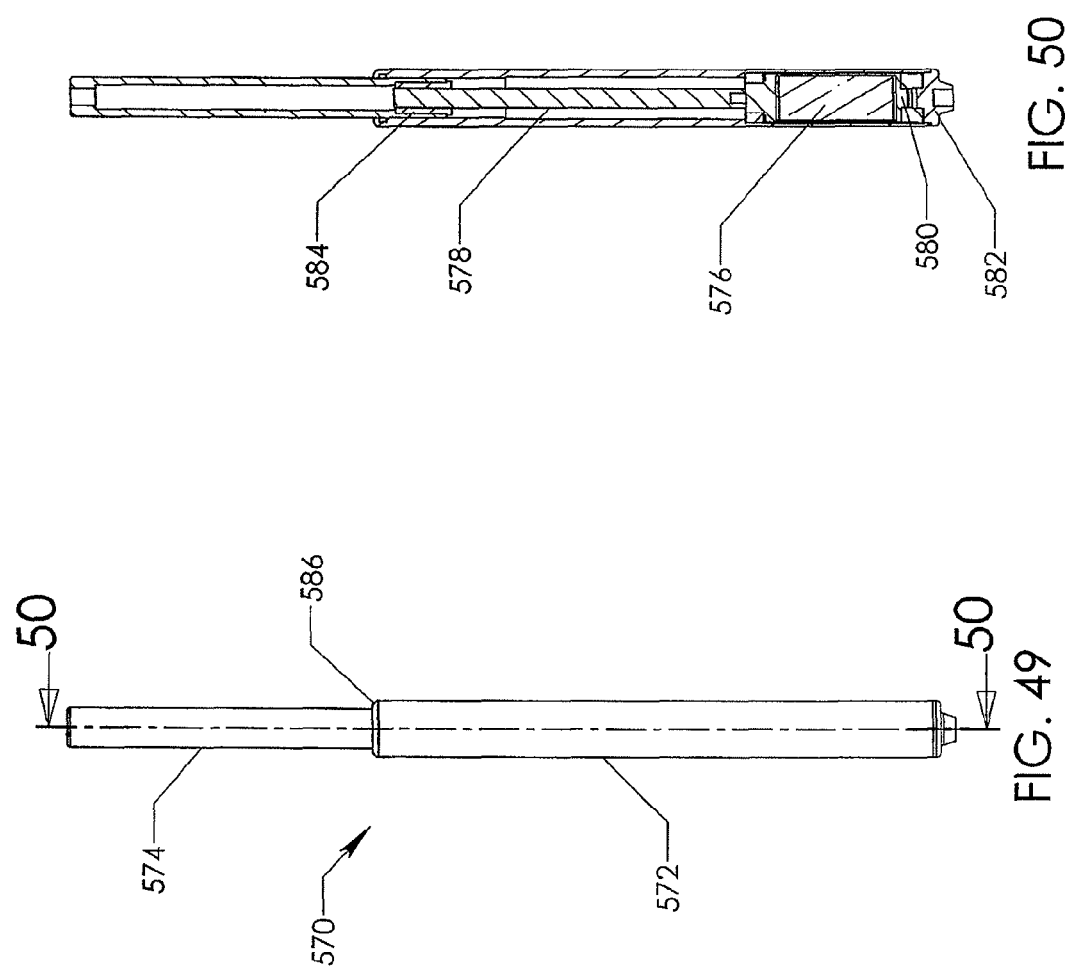

SKELETAL MANIPULATION METHOD

RELATED APPLICATION

Any and all applications for which a foreign or domestic priority claim is identified in the Application Data Sheet as filed with the present application are hereby incorporated by reference under 37 CFR 1.57.

FIELD OF THE INVENTION

The field of the invention generally relates to medical devices for treating disorders of the skeletal system.

Scoliosis is a general term for the sideways (lateral) curving of the spine, usually in the thoracic or thoracolumbar region. Scoliosis is commonly broken up into different treatment groups, Adolescent Idiopathic Scoliosis. Early Onset Scoliosis and Adult Scoliosis.

Adolescent Idiopathic Scoliosis (AIS) typically affects children between ages 10 and 16, and becomes most severe during growth spurts that occur as the body is developing. One to two percent of children between ages 10 and 16 have some amount of scoliosis. Of every 1000 children, two to five develop curves that are serious enough to require treatment. The degree of scoliosis is typically described by the Cobb angle, which is determined, usually from x-ray images, by taking the most tilted vertebrae above and below the apex of the curved portion and measuring the angle between intersecting lines drawn perpendicular to the top of the top vertebrae and the bottom of the bottom. The term idiopathic refers to the fact that the exact cause of this curvature is unknown. Some have speculated that scoliosis occurs when, during rapid growth phases, the ligamentum flavum of the spine is too tight and hinders symmetric growth of the spine. For example, as the anterior portion of the spine elongates faster than the posterior portion, the thoracic spine begins to straighten, until it curves laterally, often with an accompanying rotation. In more severe cases, this rotation actually creates a noticeable deformity, wherein one shoulder is lower than the other. Currently, many school districts perform external visual assessment of spines, for example in all fifth grade students. For those students in whom an "S" shape or "C" shape is identified, instead of an "I" shape, a recommendation is given to have the spine examined by a physician, and commonly followed-up with periodic spinal x-rays.

Typically, patients with a Cobb angle of 20° or less are not treated, but are continually followed up, often with subsequent x-rays. Patients with a Cobb angle of 40° or grater are usually recommended for fusion surgery. It should be noted that many patients do not receive this spinal assessment, for numerous reasons. Many school districts-do no perform this assessment, and many children do not regularly visit a physician, so often, the curve progresses rapidly and severely. There is a large population of grown adults with untreated scoliosis, in extreme cases with a Cobb angle as high as or greater than 90°. Many of these adults, though, do not have pain associated with this deformity, and relatively normal lives, though oftentimes with restricted mobility and motion. In AIS, the ratio of females to males for curves under 10° is about one to one, however, at angles above 30°, females outnumber males by as much as eight to one. Fusion surgery can be performed on the AIS patients or on adult scoliosis patients. In a typical posterior fusion, surgery, an incision is made down the length of the back and Titanium or stainless steel straightening rods are placed along the curved portion. These rods are typically secured to the vertebral bodies, for example with bone screws, or more specifically pedicle screws, in a manner that allows the spine to be straightened. Usually, at the section desired for fusion, the intervertebral disks are removed and bone graft material is placed to create the fusion. If this is autologous material, the bone is harvested from a hip via a separate incision.

Alternatively, the fusion surgery may be performed anteriorly. A lateral and anterior incision is made for access. Usually, one of the lungs is deflated in order to allow access to the spine front this anterior approach. In a less-invasive version of the anterior procedure, instead of the single long incision, approximately five incisions, each about three to four cm long are made in several of the intercostal spaces (between the ribs) on one side of the patient. In one version of this minimally invasive surgery, tethers and bone screws are placed and are secured to the vertebra on the anterior convex portion of the curve. Currently, clinical trials are being performed which use staples in place of the tether/screw combination. One advantage of this surgery in comparison with the posterior approach is that the scars from the incisions are not as dramatic, though they are still located in a visible area, when a bathing suit, for example, is worn. The staples have had some difficulty in the clinical trials. The staples tend to pull out of the bone when a critical stress level is reached.

Commonly, after surgery, the patient will wear a brace for a few months as the fusing process occurs. Once the patient reaches spinal maturity, it is difficult to remove the rods and associated hardware in a subsequent surgery, because the fusion of the vertebra usually incorporates the rods themselves. Standard practice is to leave this implant in for life. With either of these two surgical methods, after fusion, the patient's spine is now straight, but depending on how many vertebra were fused, there are often limitations in the degree of flexibility, both in bending and twining. As these fused patients mature, the fused section can impart large stresses on the adjacent non-fused vertebra, and often, other problems including pain can occur in these areas, sometimes necessitating further surgery. Many physicians are now interested in fusionless surgery for scoliosis, which may be able to eliminate some of the drawbacks of fusion.

One group of patients in which the spine is especially dynamic is the subset known as Early Onset Scoliosis (EOS), which typically occurs in children before the age of five, and more often in boys than in girls. This is a more rare condition, occurring in only about one or two out of 10,000 children, but can be severe, sometimes affecting the normal development of organs. Because of the fact that the spines of these children will still grow a large amount after treatment, non-fusion distraction devices known as growing rods and a device known as the VEPTR—Vertical Expandable Prosthetic Titanium Rib ("Titanium Rib") have been developed. These devices are typically adjusted approximately every six months, to match the child's growth, until the child is at least eight years old, sometimes until they are 15 years old. Each adjustment requires a surgical incision to access the adjustable portion of the device. Because the patients may receive the device at an age as early as six months old, this treatment requires a large number of surgeries. Because of the multiple surgeries, these patients have a rather high preponderance of infection.

Returning to the AIS patients, the treatment methodology for those with a Cobb angle between 20° and 48° is quite controversial. Many physicians proscribe a brace (for example, the Boston Brace), that the patient must wear on their body and under their clothes 18 to 23 hours a day until they become skeletally mature, for example to age 16.

Because these patients are all passing through their socially demanding adolescent years, it is quite a serious prospect to be forced with the choice of either wearing a somewhat bulky brace that covers most of the upper body, having fusion surgery that may leave large scars and also limit motion, or doing nothing and running the risk of becoming disfigured and possibly disabled. It is commonly known that many patients have at times hidden their braces, for example, in a bush outside of school, in order to escape any related embarrassment. The patient compliance with brace wearing has been so problematic, that there have been special braces constructed which sense the body of the patient, and keep track of the amount of time per day that the brace is worn. Patients have even been known to place objects into unworn braces of this type in order to fool the sensor. Coupled with the inconsistent patient compliance with brace usage, is a feeling by many physicians that braces, even if used properly, are not at all effective at curing scoliosis. These physicians may agree that bracing can possibly slow down or even temporarily stop curve (Cobb angle) progression, but they have noted that as soon as the treatment period ends and the brace is no longer worn, often the scoliosis rapidly progresses, to a Cobb angle even more severe than it was at the beginning of treatment. Some say the reason for the supposed ineffectiveness of the brace is that it works only on a portion of the torso, and not on the entire spine. Currently a prospective, randomized 500 patient clinical trial known as BrAIST (Bracing in Adolescent Idiopathic Scoliosis Trial) is enrolling patients, 50% of whom will be treated with the brace and 50% of who will simply be watched. The Cobb angle data will be measured continually up until skeletal maturity, or until a Cobb angle of 50° is reached, at which time the patient will likely undergo surgery.

Many physicians feel that the BrAIST trial will show that braces are completely ineffective. If this is the case, due quandary about what to do with AIS patients who have a Cobb angle of between 20° and 40° will only become more pronounced. It should be noted that the "20° to 40°" patient population is as much as ten times larger than the "40° and greater" patient population.

Currently, genetic scientists are at work to find one or more genes that may predispose scoliosis. Once identified, some are still skeptical as to whether gene therapy would be possible to prevent scoliosis, however the existence of a scoliosis gene would no doubt allow for easier and earlier identification of probable surgical patients.

SUMMARY OF THE INVENTION

In a first embodiment, a method of bating scoliosis in a subject includes securing a scoliosis treatment device to first and second locations on the subject's skeletal system, the scoliosis treatment device including a first portion, a second portion moveably mounted relative to the first portion, and an adjustment device disposed on the device and configured to change a distraction force between the first location and the second location, the adjustment device including a rotationally mounted magnetic element configured to move the second portion relative to the first portion in response to rotation of the magnetic element. An external adjustment device is provided external to the subject, the external adjustment device including a first rotating magnet adapted to rotate about a first axis and a second rotating magnet spaced apart from the first rotating magnet and adapted to rotate about a second, separate axis. The implant is adjusted non-invasively by moving the first and second rotating magnets of the external adjustment device so as to increase the distraction force between the first location and second location.

In another embodiment, a method of treating scoliosis includes securing a scoliosis treatment device to first and second locations on the subject's skeletal system, the scoliosis treatment device including a first portion, a second portion, moveably mounted relative to the first portion, and an adjustment device disposed on the device and configured to change a distraction force between the first location and the second location, the adjustment device having a rotationally mounted magnetic element. An external adjustment device is provided external to the subject, the external adjustment device including first and second rotating magnetic fields rotating about separate axes, the first and second rotating magnetic fields being disposed on the same side of the subject's body. The implant is non-invasively adjusted by rotating the first and second magnetic fields of the external adjustment device so as to increase the distraction force between the first location and second location.

In still another embodiment, a method of treating scoliosis in a subject includes identifying a genetic susceptibility of a subject having a Cobb angle of less than or equal to 30° to develop a Cobb angle of greater than or equal to 40°. A scoliosis treatment device is secured to first and second locations on the subject's skeletal system, the scoliosis treatment device including a first portion, a second portion moveabiy mounted relative to the first portion, and an adjustment device disposed on the device and configured to change a distraction force between the first location and the second location, the adjustment device having a rotationally mounted magnetic element. An external adjustment device is provided external to the subject, the external adjustment device having at least one rotating magnet adapted to rotate about an axis. The implant is non-invasively adjusted by rotating the at least one rotating magnet of the external adjustment device.

In still another embodiment, a method of non-invasively adjusting a magnetically-driven device implanted within a subject includes locating the subject within a magnetic field created by a magnetic resonant imaging instrument and rotating the subject about an axis of rotation.

In yet another embodiment, a method of treating scoliosis in a skeletally mature subject having an initial Cobb angle of more than 40° includes securing a scoliosis treatment device to first and second locations on the subject's skeletal system, the scoliosis treatment device including a first portion, a second portion moveably mounted relative to the first portion, and an adjustment device disposed on the device and configured to change a distraction force between the first location and the second location, the adjustment device having a rotationally mounted magnetic element. An external adjustment device is provided external to the subject, the external adjustment device including at least one rotating magnet adapted to rotate about an axis. The implant is periodically adjusted in a non-invasive manner by rotating the at least one rotating magnet of the external adjustment device so as to reduce the Cobb angle of the subject from the initial Cobb angle.

BRIEF DESCRIPTION OF THE DRAWINGS

FIG. 6B illustrates a detailed view of portion A of FIG. 6A in accordance with an embodiment of the present invention.

FIG. 6E illustrates, an end view of a cylindrical magnetic member for actuating a clamp in accordance with an embodiment of the present invention.

FIG. 13A illustrates a cross-sectional representation of the external adjustment device being positioned on a patient's skin. FIG. 13A illustrates the permanent magnet of the implantable interface in the 0° position.

FIG. 13B illustrates a cross-sectional representation of the external adjustment device being positioned on a patient's skin. FIG. 13B illustrates the permanent magnet of the implantable interface in the 90° position.

FIG. 13C illustrates a cross-sectional representation of the external adjustment device being positioned on a patient's skin. FIG. 13C illustrates the permanent magnet of the implantable interface in the 180° position.

FIG. 13D illustrates a cross-sectional representation of the external adjustment device being positioned on a patient's skin. FIG. 13D illustrates the permanent magnet of the implantable interface in the 270° position.

FIGS. 15-22 illustrate cross-sectional views of the driven magnet along with the acoustic or sonic indicator housing illustrating the rotational orientation of the magnet and the magnetic ball. Various states are illustrated as the magnet rotates in the clockwise direction.

FIGS. 23-30 illustrate cross-sectional views of the driven magnet along with the acoustic or sonic indicator housing illustrating the rotational orientation of the magnet and the magnetic ball. Various states are illustrated as the magnet rotates in the counter-clockwise direction.

FIG. 49 illustrates an adjustable portion of a distraction device according to one embodiment.

FIG. 50 illustrates a cross-sectional view of the adjustable portion of FIG. 49 taken along the line 50-50 of FIG. 49.

DETAILED DESCRIPTION OF THE ILLUSTRATED EMBODIMENT

Figure 1:
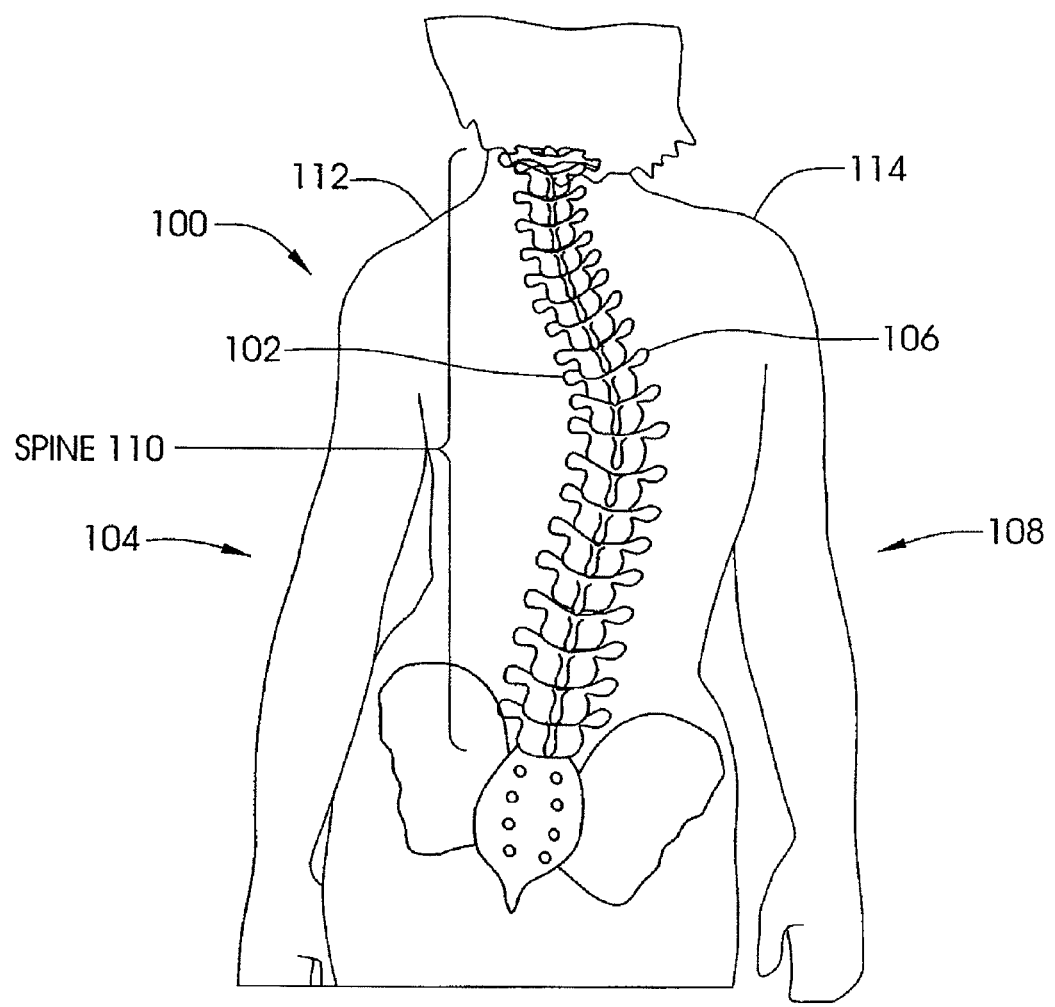
FIG. 1 illustrates the spine of a person with scoliosis.

FIG. 1 illustrates a patient 100 with scoliosis. The concave portion 102 of the spinal curve can be seen on the left side 104 of the patient 100, and the convex portion 106 can be seen on tire right side 108 of the patient 100. Of course, in other patients, the concave portion 102 may appear on the right side 108 of the patient 100 while the convex portion 106 may be found on the left side 104 of the patient. In addition, as seen in FIG. 1, some rotation of the spine 110 is present, and unevenness between the left shoulder 112 and right shoulder 114 is seen.

Figure 2:
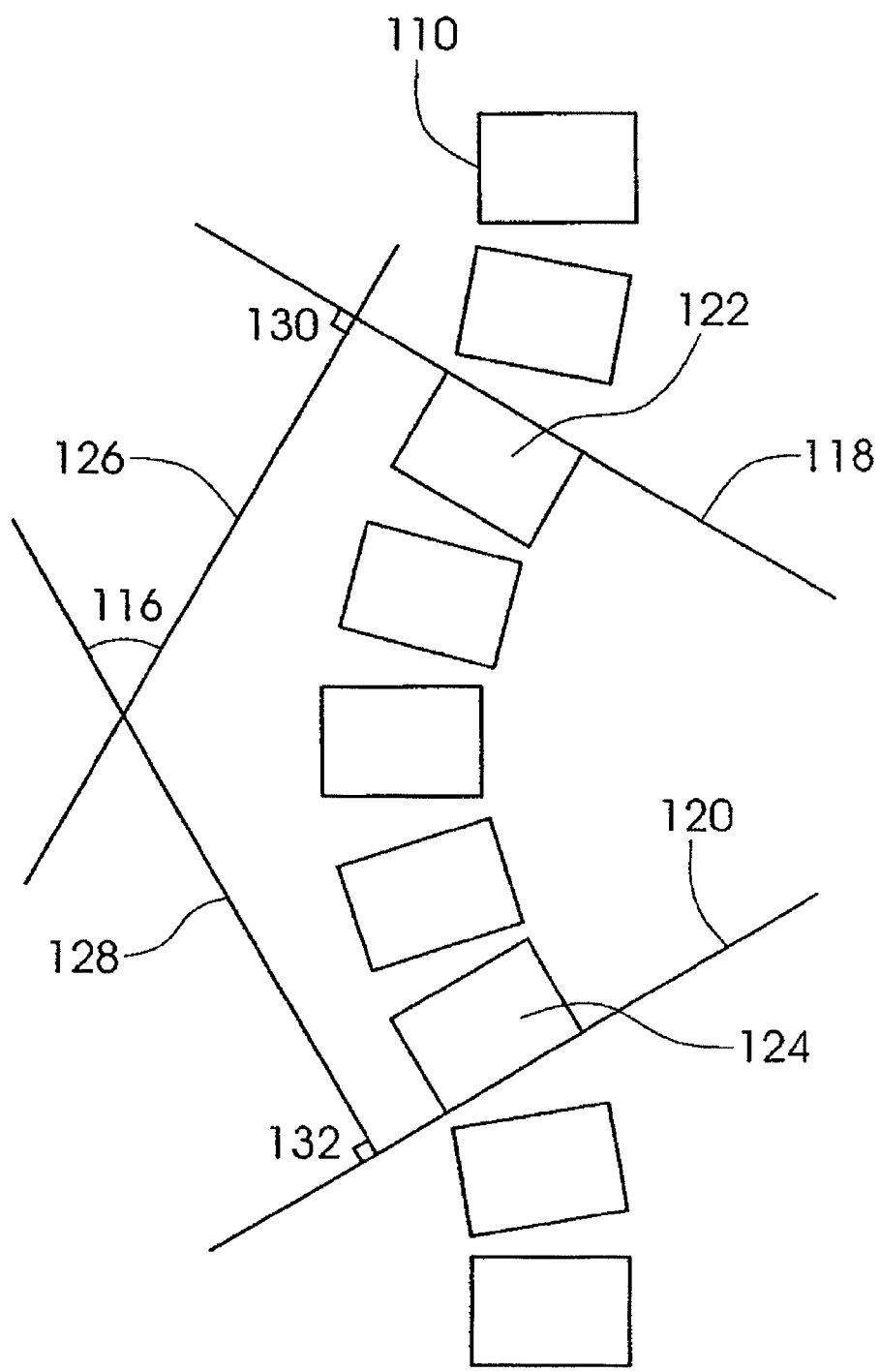
FIG. 2 illustrates the Cobb angle of a scoliotic spine.

FIG. 2 illustrates the Cobb angle 116 of a spine 110 of a patient with scoliosis. To determine the Cobb angle, lines 118 and 120 are drawn from vertebra 122 and 124, respectively. Intersecting perpendicular lines 126 and 128 are drawn by creating 90° angles 130 and 132 from lines 118 and 120. The angle 116 created from the crossing of the perpendicular lines 126 and 128 is defined as the Cobb angle. In a perfectly straight spine, this angle is 0°.

Figure 3:
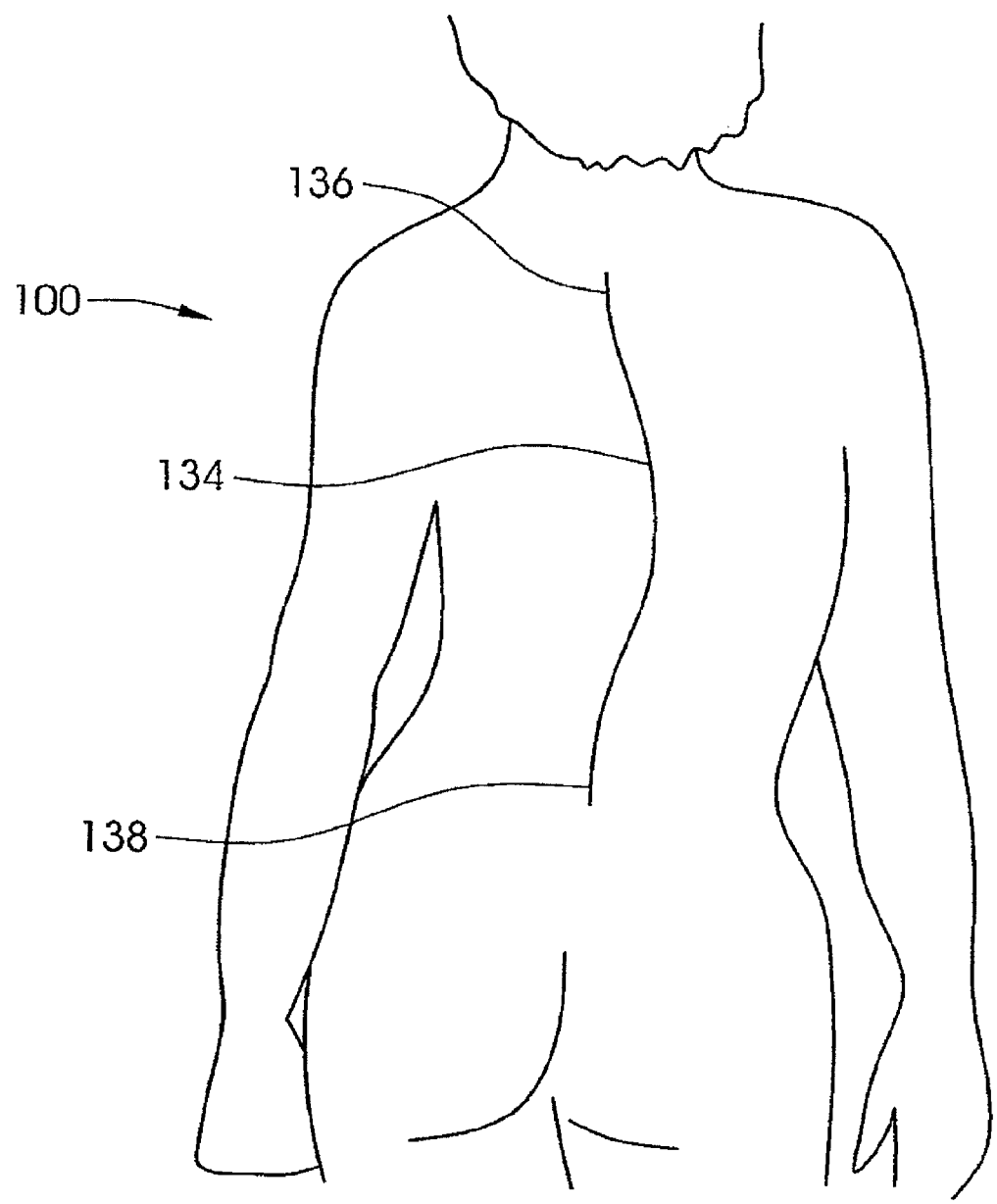
FIG. 3 illustrates the large incision made during prior art scoliosis fusion surgery.

In many Adolescent Idiopathic Scoliosis (AIS) patients with a Cobb angle of 40° or greater, spinal fusion surgery is typically the first option. FIG. 3 illustrates a long incision 134 formed in the patient 100 which is typically made during posterior scoliosis fusion surgery. This type of fusion surgery is known in the prior art. The long incision 134 extends between an upper end 136 and a lower end 138. The length of this incision 134 is longer than the length of the section of the vertebra to be fused. The actual length between the upper end 136 and the lower end 138 varies, depending on the size of the patient, and the extent of the scoliosis, but in AIS patients this length is significantly longer than 15 cm. More typically, it is longer than 25 cm.

Figure 4:
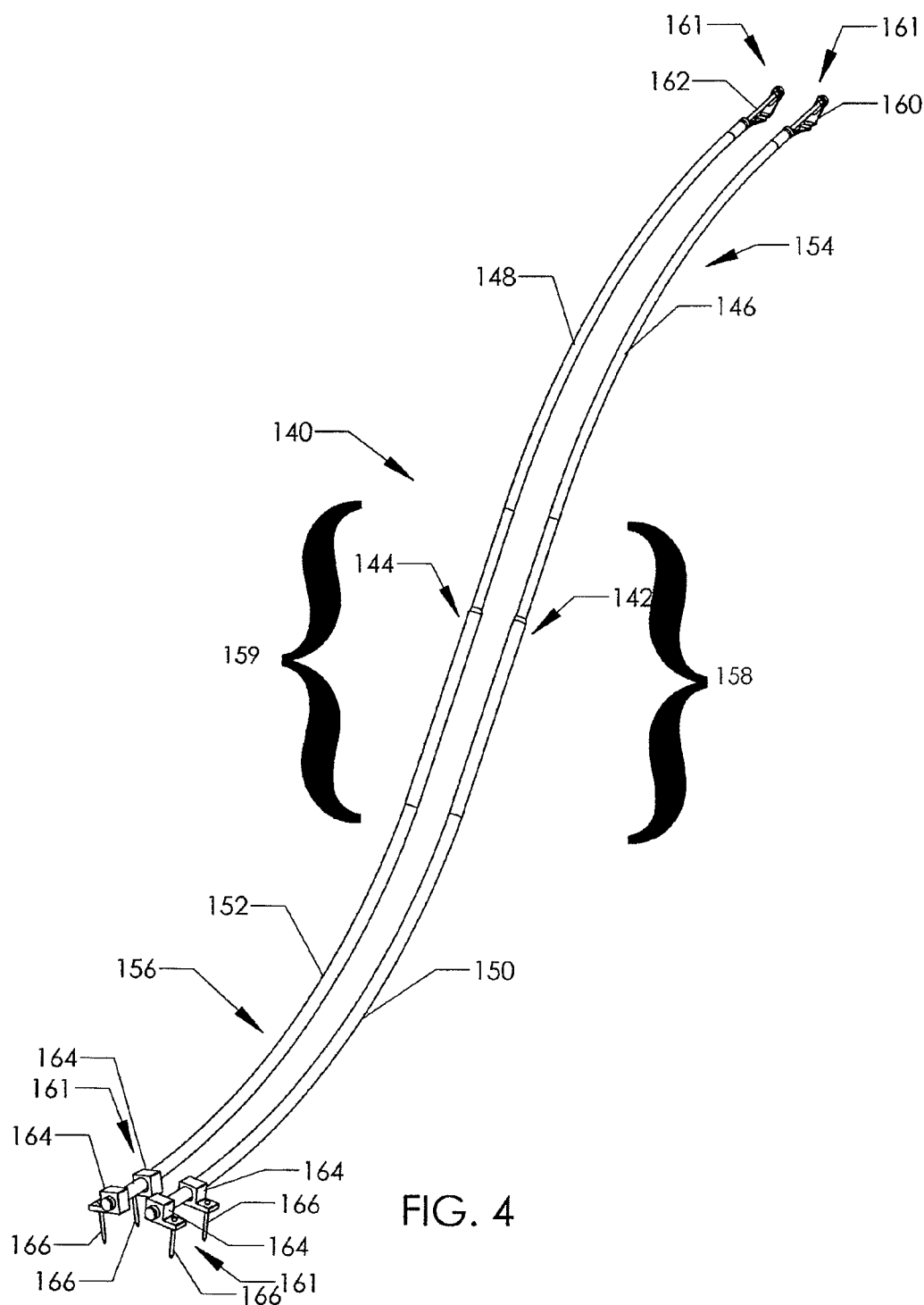
FIG. 4 illustrates a two rod embodiment of the present invention.
Figure 5:
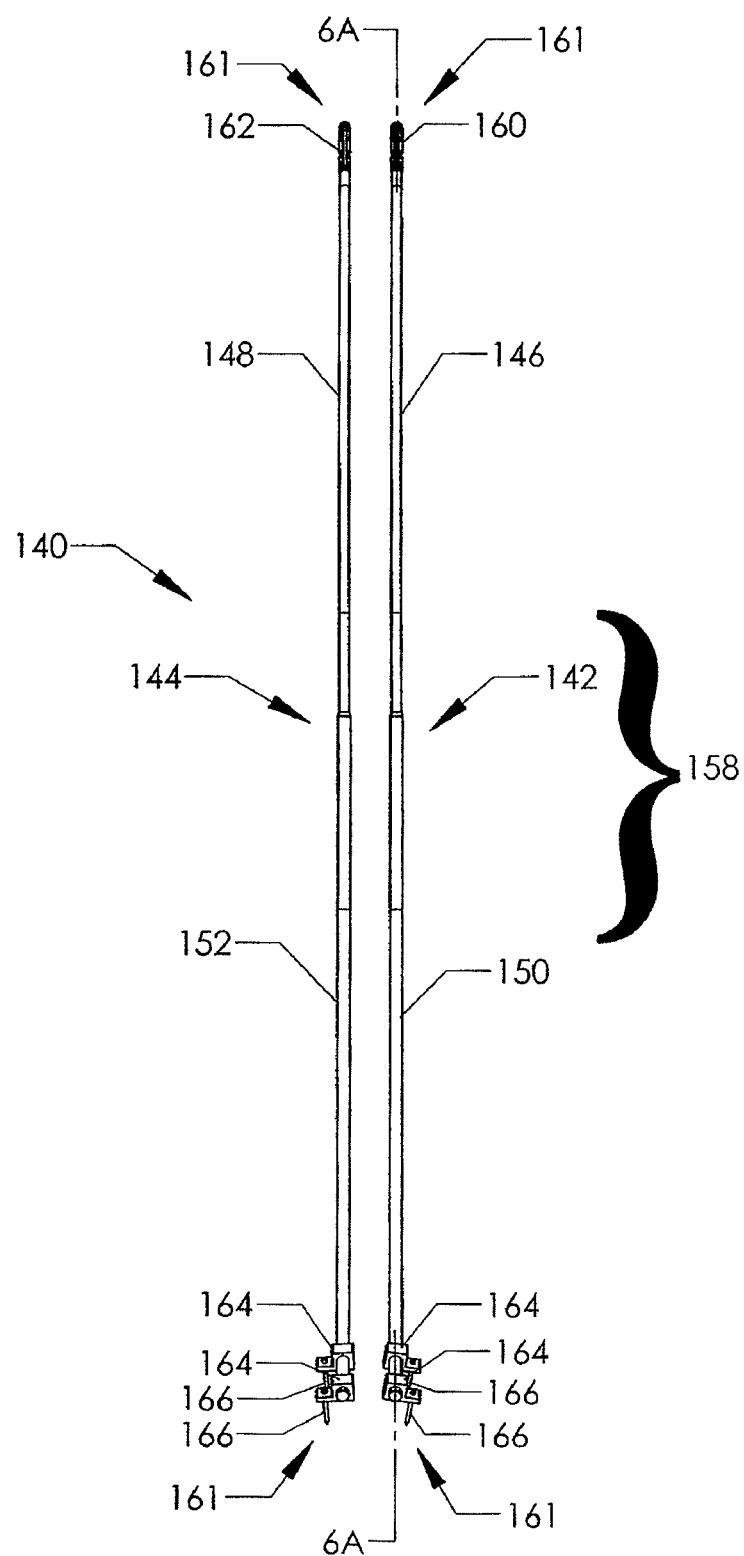
FIG. 5 illustrates a posterior view of the two rod embodiment of the present invention.

FIGS. 4 and 5 illustrate a distraction device 140 for treating scoliosis according to one embodiment of the invention. The distraction device 140, which is an implantable device, includes a first adjustable rod 142 and a second adjustable rod 144. For patient distraction, a first adjustable rod 142 is positioned on one side of the spine 110 while the second adjustable rod 144 is positioned on the opposing side of the spine 110. The spine 110 is omitted from view in FIGS. 4 and 5 for sake of clarity. While the distraction device 140 illustrated in FIGS. 4 and 5 comprises first and second adjustable rods 142, 144, it should be understood that in alternative embodiments, the distraction device 140 may include just a single adjustable rod 142 (the second adjustable rod 144 being omitted entirely) that is implanted within the patient.

Referring back to FIGS. 4 and 5, each adjustable rod 142, 144 includes a first elongate member 146, 148 and a second elongate member 150, 152, that are coupled together by an adjustable portion 158, 159. The adjustable portions 158, 159 include a variable overlapping region between the first elongate members 146, 148 and the second elongate members 150, 152 which allows for the non-invasive adjustment of the length of each adjustable rod 142, 144. In this particular embodiment, the first elongate elements 146, 148 are telescopically contained within hollow receiving portions of the second elongate elements 150, 152, and the adjustable portions 158, 159 are substantially straight. As illustrated, the adjustable rods 142, 144 have an upper curve 154 and a lower curve 156, which allow them to better conform to the natural front-to-back curve of the spine. For example, the upper curve 154 conforms to the normal kyphosis of the upper thoracic region and the lower curve 156 conforms to the normal lordosis of the lumbar region. In one aspect of the invention, the curved portions 154, 156 are bendable in order to better conform to a patient's specific spinal configuration. For the example, the curved portions 154, 156 may be made of a malleable or elastic-type material such that the surgeon can manually alter the particular shape of each adjustable rod 142, 144 to the specific needs of the patient. In a large number of scoliosis patients, especially adolescent idiopathic scoliosis patients, the scoliotic curve does not include the lower lumbar levels of the spine and so the lower curve 156 is not necessary. As explained above, the embodiment illustrated in FIGS. 4 and 5 represents a dual rod configuration. With this configuration, both rods 142, 144 are inserted through the same incision, and can be placed along the spine 110 on two opposite sides of the center line of the spine 110. Alternatively, each may be placed through its own, smaller incision.

Figure 37:
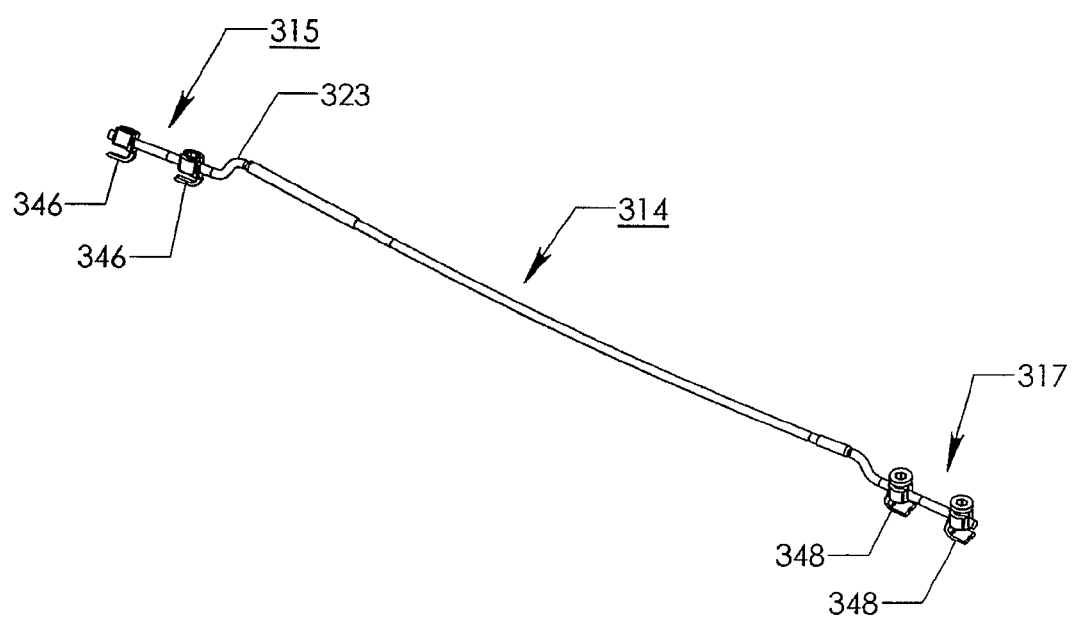
FIG. 37 illustrates a distraction device according to another embodiment. Anchors in the form of hooks are illustrated at opposing ends of the distraction rod.
Figure 38:
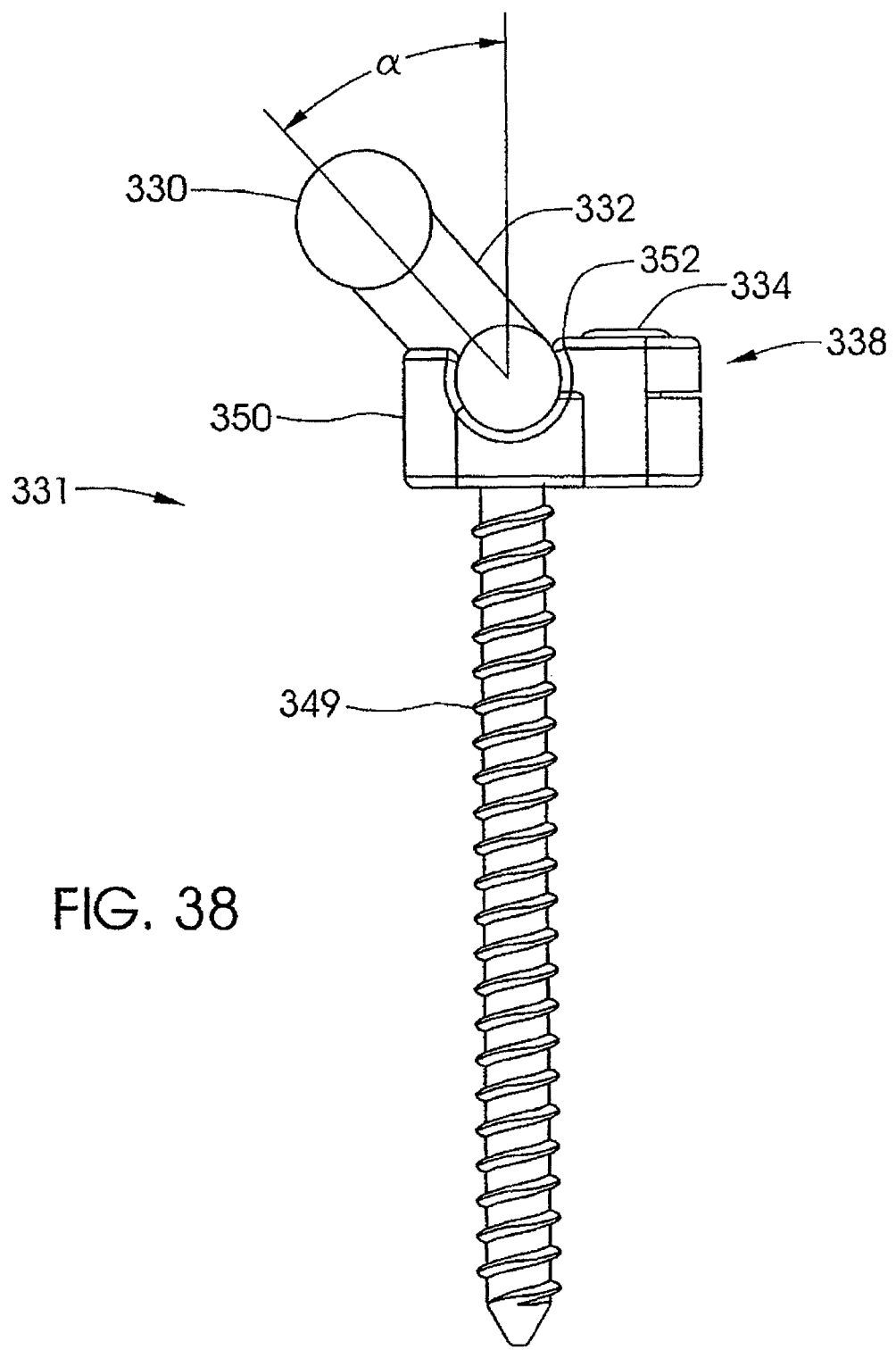
FIG. 38 illustrates a side view of a pedicle screw system used in accordance with the embodiment illustrated in FIG. 36.

Alternatively, a single adjustable rod version 142 can be used, preferably positioned on the concave side of the scoliosis curve. Yet another variation includes a single adjustable rod 142 that does not have either or both of the curves (i.e., curves 154 and 156 omitted). A straight adjustable rod 142 of this nature may be placed further lateral (to the side of the spine 110), and not necessarily have to hug the front-to-back contours of the spine 110 or the muscle covering the spine 110. In still another embodiment, the first elongate member (e.g., 146, 148) and the second elongate member (e.g., 150, 152) do not telescope in relation to one another, but rather are in parallel, at least along the adjustable portion 158, 159. The distraction device 140 is implanted in the patient 100 in order to straighten the scoliotic spine 110. For this reason, each end of the adjustable rods 142, 144 advantageously contains an anchor 161 that allows for securement to a location in the skeletal system. For example, the anchor 161 at either end may include a clamp for clamping to a skeletal structure. Alternatively, either end may comprise a bracket for securing to a section of bone with the use of a bone screw or pedicle screw. The embodiment in FIG. 4 illustrates a clamp 160, 162 at the upper end of the first elongate members 146, 148 and brackets 164 at the end of the second elongate members 150, 152. The brackets 164 can be secured to the second elongate members 150, 152 by a variety of methods, including set screws, welding, soldering, swaging, crimping or mechanical joints. Screws 166 secure the brackets 164 to bony structures, such as the vertebral bodies or the sacrum. The clamp 160, 162 can be used to clamp the distraction device 140 to a rib or the articulation of the rib with the vertebra at the facet. FIGS. 37 and 38, which are described in more detail below, illustrate alternative anchors 161 that may be used to secure the first elongate members 146, 148 or second elongate members 150, 152 to the skeletal structure.

The distraction device 140 is configured such that the adjustable portion(s) 158, 159 change at least one of the distance or force between the anchor or affixation points (e.g., at the spine or other anatomical structure) of the first elongate member(s) 146, 148 and the second elongate member(s) 150, 152. For example, the adjustable portion(s) 158, 159 may increase the length between the anchor or affixation points. Similarly, the adjustable portion(s) 158, 159 may increase the force (e.g., distraction force) between the anchor or affixation points. The adjustable portion(s) 158, 159 may alter both the distance and force at the same time.

Figure 6A:
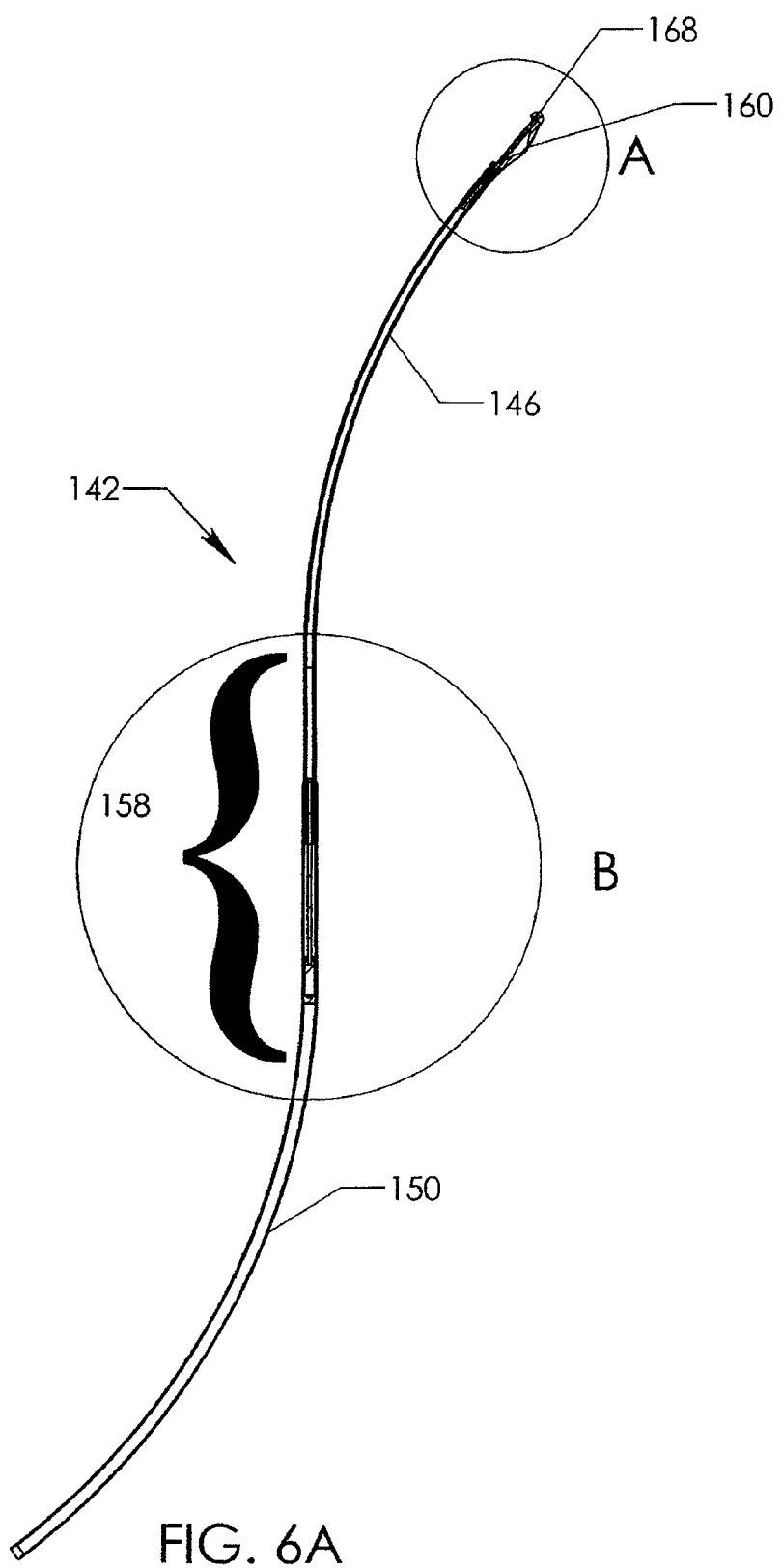
FIG. 6A illustrates a sectional view of a single rod in accordance with an embodiment of the present invention taken through line 6A-6A of FIG. 5.
Figure 7:
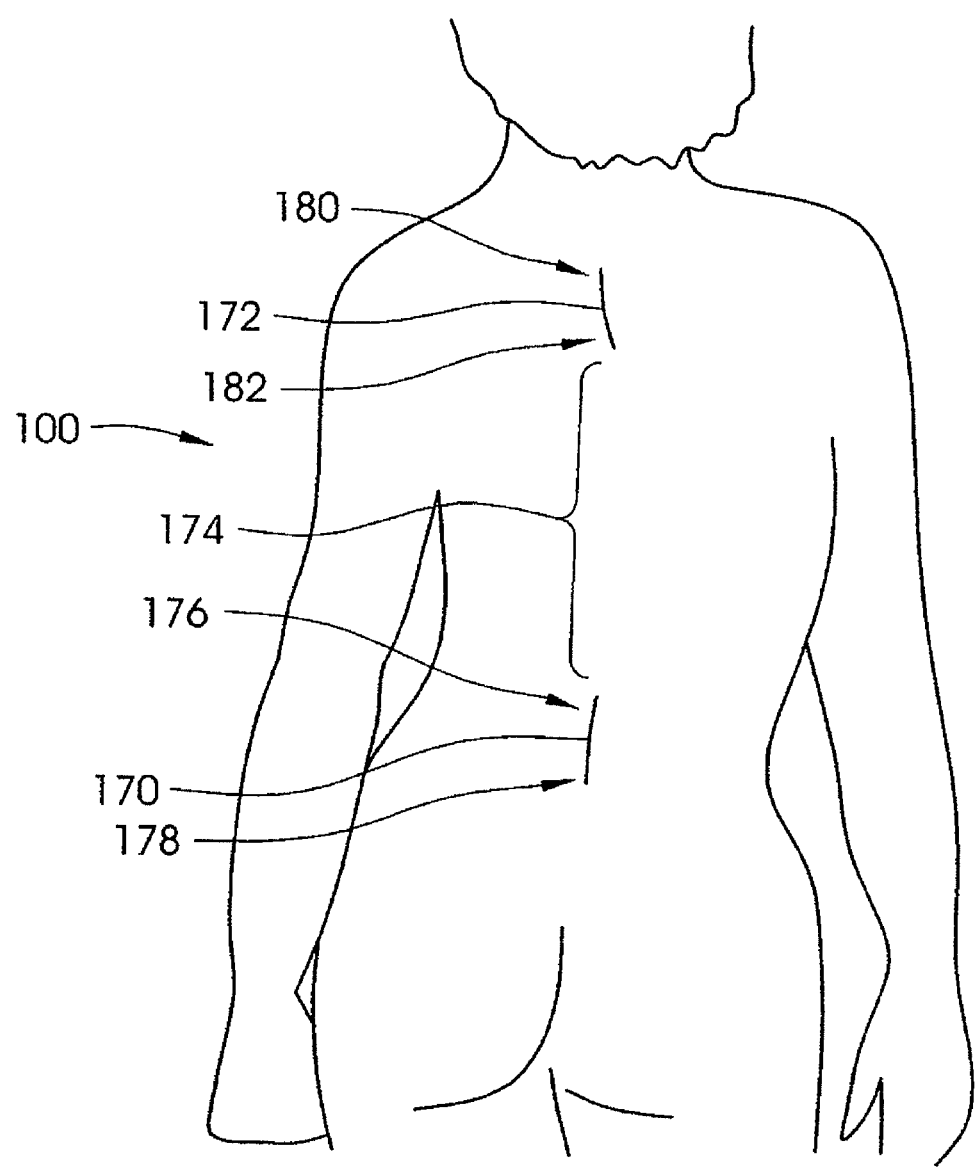
FIG. 7 illustrates the two smaller incisions winch are possible using the system of the invention.

FIG. 6A illustrates a sectional view of the first adjustable rod 142 indicating the location of the adjustable portion 158 and the clamp 160. The tip 168 of clamp 160 is shaped to allow for blunt dissection of tissue, so that the adjustable rod 142 may be placed under the skin and pushed for much of the length of the spine 110, so that a large portion of the long incision 134 of FIG. 3 is not necessary. This allows for, for instance, alternative incision geometry, such as that illustrated in FIG. 7. As seen in FIG. 7, a lower incision 170 is made having an upper end 176 and a lower end 178 (for example, by a scalpel) and the first adjustable rod 142 is placed through the lower incision 170 and under the skin. Using a dissection technique, the first adjustable rod 142 is inserted under the skin along an intermediate area 174. The dissection technique may include the use of a scope (laparoscope, arthroscope, endoscope, or the like) and an additional dissecting tool, but usually can be done without these tools. The additional dissecting tool may include, for example, a tapered sheath, which is advanced over the first adjustable rod 142, dissecting the tissue along the way, while being visualized by scope, for example on a monitor. Alternatively, the additional dissecting tool may be a blunt dissecting tool, consisting of two fingers which can be spread apart and brought together, once again, while being visualized by the scope.

Once the clamp 160 of the first adjustable rod 142 (as seen in FIG. 6A) is advanced to the location near the anatomy to be clamped, an upper incision 172 is made having an upper end 180 and a lower end 182 and the location near the anatomy to be clamped is exposed by dissection. The clamp 160 is then actuated to clamp this anatomical structure, and additionally, the opposite end of the first adjustable rod 142 is secured, for example by a bone screw (e.g., pedicle screw) and bracket combination. The adjustment device of the adjustable rod 142 (to be described later) may be adjusted prior to the securement of either end of the first adjustable rod 142, so that the desired length is achieved. After securement of both ends, first adjustable rod 142 may then be adjusted in order to adjust the distraction distance or distraction force between the two locations in the anatomy to a desired amount in one aspect of the invention, the length of the first adjustable rod 142 may first be adjusted manually by the physician without using the remotely-operated adjustment device as described herein. For example, the initial length of the adjustable rod 142 may be manually set by the physician by pushing or pulling the first and second elongate members 146, 150 relative to one another. Alternatively, the length of the adjustable rod 142 may be adjusted by trimming or removing a portion of the length of the adjustable rod 142.

By having the physician adjust the length of the adjustable rod 142 during initial placement, a distraction force may be applied to the spine 110 without having to use any displacement distance or force that is provided by the remotely-operated adjustment device. For example, there typically is a limited degree of movement that is provided by the remotely-operated adjustment device. When the physician applies a first or initial distraction force upon implantation, the budget of available displacement for the remotely-operated adjustment device is saved for later adjustments.

Still referring to FIG. 7, the two incisions are then closed using standard techniques. As described, the single long incision is now replaced by two, shorter incisions 170, 172, whose combined length when added together is less than the length of the single long incision illustrated in FIG. 3. For example, lower incision 170 and upper incision 172 each has a length of less than 15 cm, and preferably, each has a length of less than 7.5 cm, and more preferably, less than 5 cm.

Figure 8:
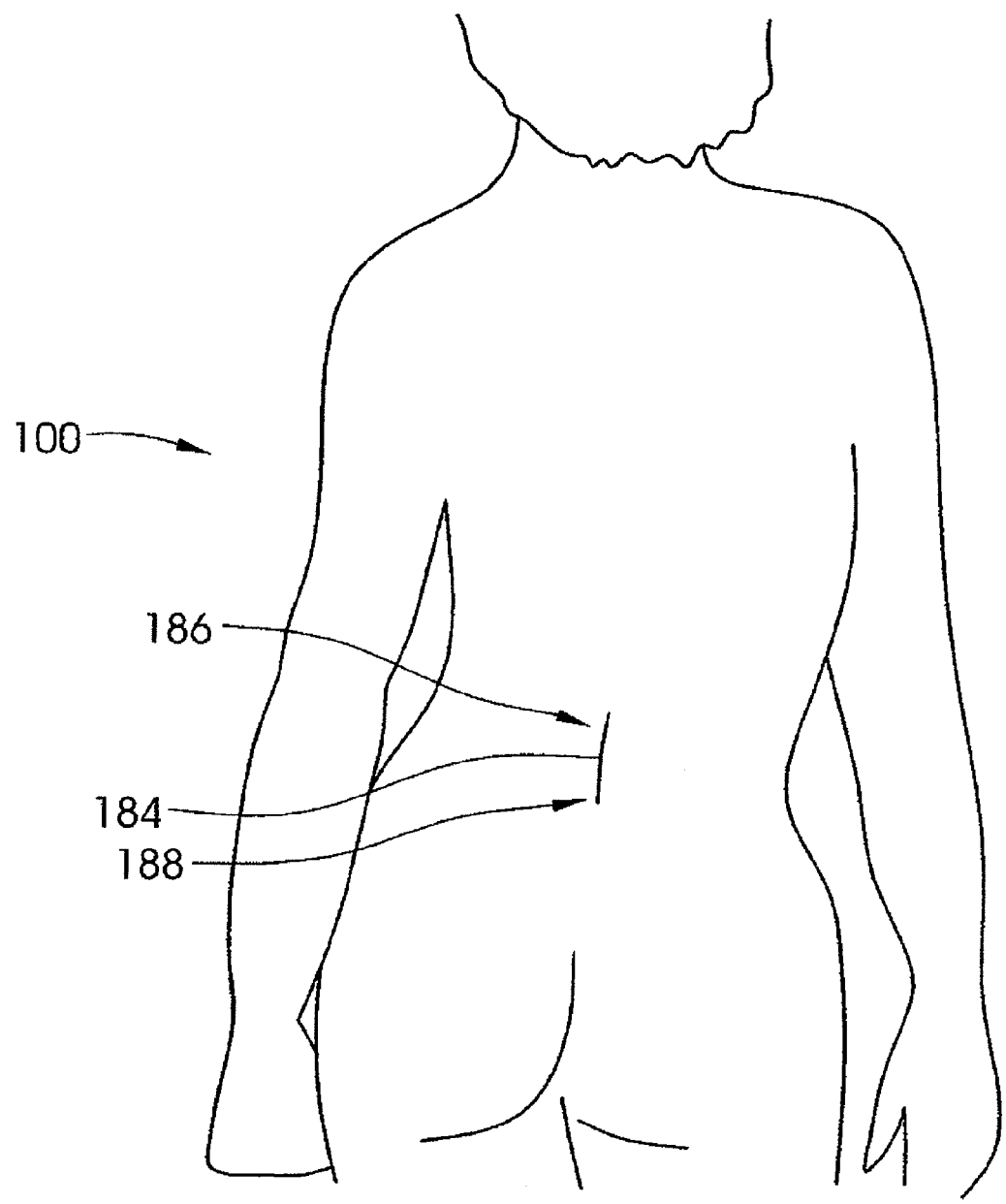
FIG. 8 illustrates a single small incision which is possible using another embodiment of the system of the invention.

An optional magnetic clamping device is illustrated in FIG. 6B, which allows for the entire procedure to be done under a single short incision 184, as seen in FIG. 8. As previously described, a single short incision 184 having an upper end 186 and a lower end 188 is made (for example, by a scalpel) and the first adjustable rod 142 is placed through the single small incision 184 and under the skin. Using a dissection technique, the first adjustable rod 142 is inserted under the skin towards the upper target location. As previously described, this dissection technique may include the use of a scope (laparoscope, arthroseope, endoscope, or the like) and an additional dissecting tool. Once the clamp 160 of the first adjustable rod 142 is advanced to the location near the anatomy to be clamped, one or more dissecting tools and a scope are used to expose the target location, for example a rib or facet articulation. Referring to FIG. 6B, the magnetically-operated clamp 160 includes a first finger 190 and a second finger 192. The first linger 190 is permanently coupled to first elongate element 146 while the second finger 192 is longitudinally adjustable in relation to first linger 190, so that gap 194 may be increased or decreased in response to actuation. A closure device 198 is operated by an external adjustment device such as that illustrated in FIGS. 10-12 in order to increase or decrease gap 194, and therefore open or close clamp 160. As will be described, the clamp 160 is magnetically adjustable, and so the clamping process may be performed non-invasively, therefore making a second incision unnecessary.

The magnetically-operated clamp 160 may be particularly useful if as expected, the evidence of the ineffectiveness of braces becomes stronger, many physicians will be searching for less invasive procedures to treat scoliosis. Patients will demand that the procedures be as minimally invasive as possible, and one of the big elements in their decision to undergo surgery is the size of the incision, and thus size of the scar, both during and alter healing. AIS patient whose Cobb angles are greater than 40° are more likely to be treated with fusion surgery, but patients in the 20° to 40° range may be treatable using fusionless methods which harness the growing power of their spine. Currently, it is known that female AIS patients who have not yet reached menarche (the first menstrual period) are more likely to have a curve that will progress farther. Additionally, AIS patients whose age is younger are more likely to have their curves progress. One or more "scoliosis genes" have recently been discovered, and work is being done to create a genetic test that allows identification of a patient whose curve is very likely to progress beyond 40° at a time when her Cobb angle is less than 40°, for example 20°. Because braces are a questionable option, it is expected that a minimally invasive, non-fusion procedure will be the procedure of choice for these patients. Though the incision 184 in FIG. 8 is depicted as a vertical incision, alternatively, it may be made horizontally. For example, the horizontal incision may be made so that it is just below and parallel to the "bikini line", allowing the resulting scar to be more concealed. This could also be done with incision 170 in FIG. 7.

Figure 10:
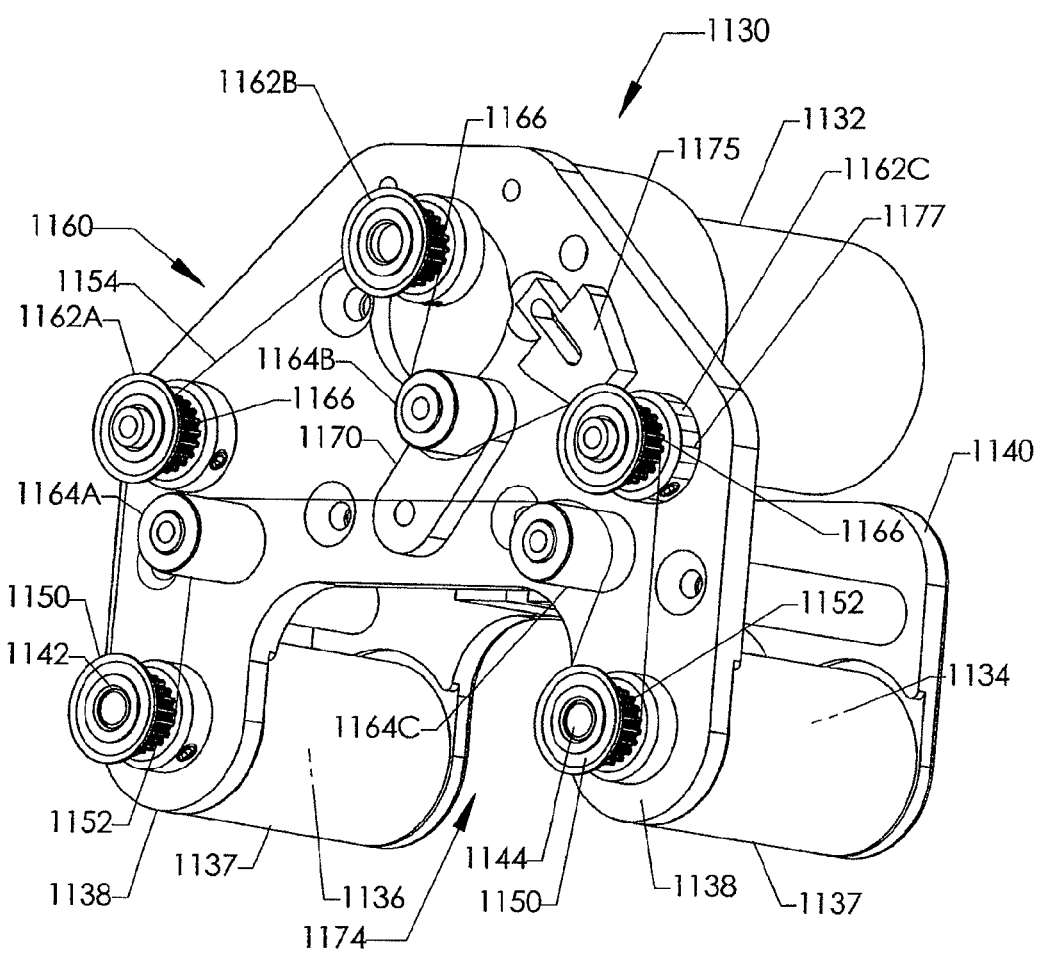
FIG. 10 illustrates a perspective view of an external adjustment device according to one embodiment. The outer housing or cover is removed to illustrate the various aspects of the external adjustment device.
Figure 11:
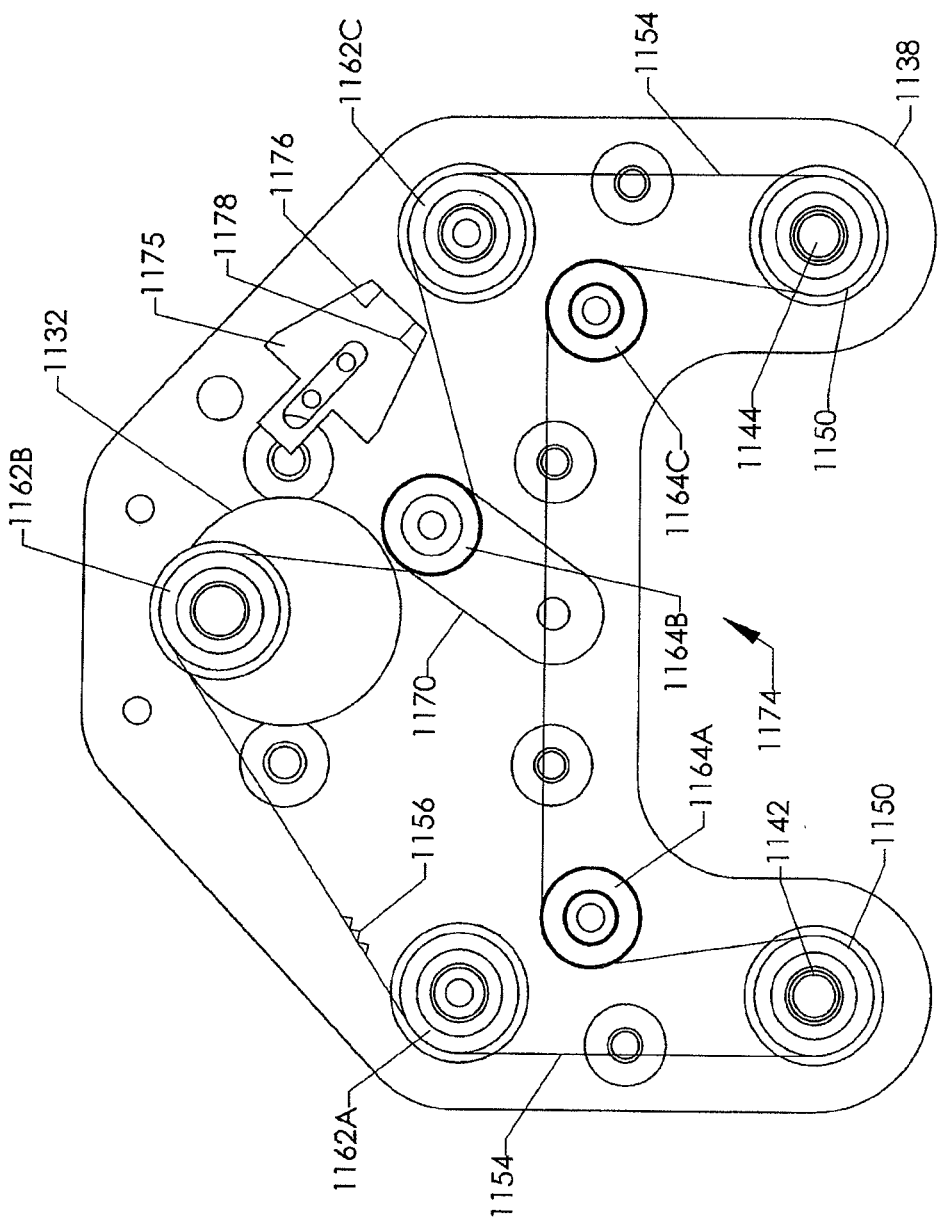
FIG. 11 illustrates a side or end view of the external adjustment device of FIG. 10.
Figure 12:
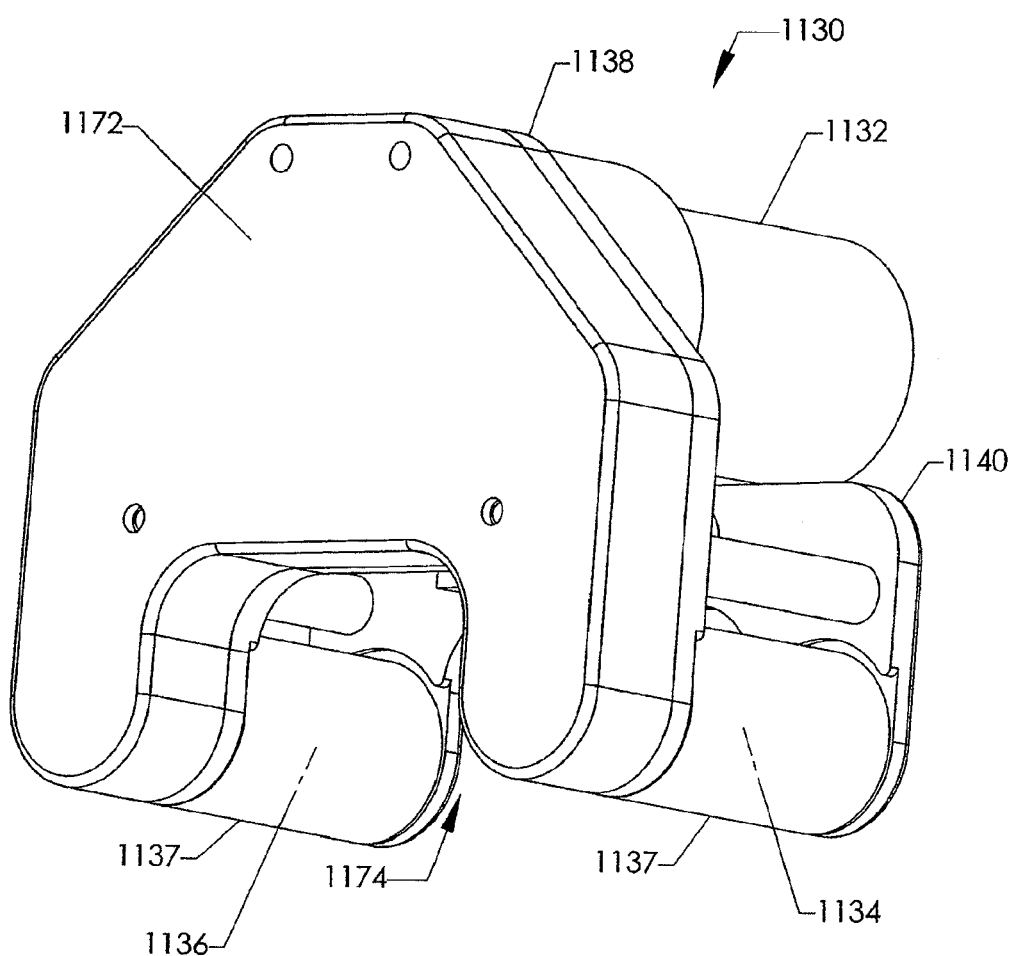
FIG. 12 illustrates a perspective view of an external adjustment device of FIG. 10 with the outer housing or cover in place.

Returning to FIG. 6B, closure device 198 includes a cylindrical magnetic member 200, which can be activated by magnetic coupling with an external adjustment device (such as external adjustment device 1130 illustrated in FIGS. 10-12). Though configurations may vary for this closure device 198, in this particular embodiment, magnetic member 200 is a hollow rare earth magnet, preferably Neodymium-Iron-Boron. As seen from an end view in FIG. 6E, the magnetic member 200 has a threaded insert 202 having a female thread so that when the magnetic member 200 rotates, the threaded insert 202 rotates in unison. Magnetic member 200 is a permanent magnet 217 having a north pole 204 and a south pole 206. Magnetic member 200 is preferably coated with a material, for example Parylene, phenolic resin or Gold, which is non-magnetic, but protective and biocompatible in a body implant application. In certain embodiments, the individual Nd—Fe—B magnets are enclosed within a stainless steel casing/housing or various layers of nickel, gold or copper plating to protect the corrosive Nd—Fe—B material from the environment inside the body. In other embodiments, other magnetic materials may be used, including SmCo (Samarium Cobalt), which is typically available as $SmCo_5$, or $SmCo_{15}$, $Sm_2Co_{17}$, or AlNiCo (Aluminum Nickel Cobalt). In still other embodiments, Iron Platinum (Fe—Pt) may be used. Iron platinum magnets achieve a high level of magnetism without the risk of corrosion, and may possibly preclude the need to encapsulate. In yet other embodiments, the permanent magnets 217 on the implantable interface may be replaced by magnetically responsive materials such as Vanadium Permendur (also known as Hiperco).

It should be noted that magnetic member 200 can also be hermetically sealed within the first elongate element 146. When the external adjustment device 1130 is operated, it applies a moving magnetic field, which causes magnetic member 200 to rotate. Attached to the second linger 192 is a threaded rod 210 which threadedly engages the female thread of the threaded insert 202. When the magnetic member 200 is rotated by the external adjustment device 1130 in a first direction, the threaded rod 210 moves in a first longitudinal direction 212, causing the second finger 192 to move away from the first finger 190, and the gap 194 to open. There may also be a manual adjustment mechanism on the clamp 160 so that the clamp 160 may be opened outside the patient, in preparation for the procedure. When gap 194 is adjusted to be wider than the anatomical structure, for example rib, around which the clamp 160 is to be secured, then through visualization by the scope and manipulation with the dissecting tools, the clamp 160 is placed over the rib, so that rib is contained in cavity 196. At this point the external adjustment device 1130 is operated so that it turns the magnetic member 200 in the opposite direction causing the threaded rod 210 to move longitudinally in a second direction 214, and the two fingers 190, 192 close around the rib. The gap 194 is now smaller than the width of the rib, and thus, the clamp 160 is secure. If the implant is to be removed at a later date, the magnetic clamp mechanism may also be used to remove the implant without having to make an incision adjacent the clamp.

Figure 6C:
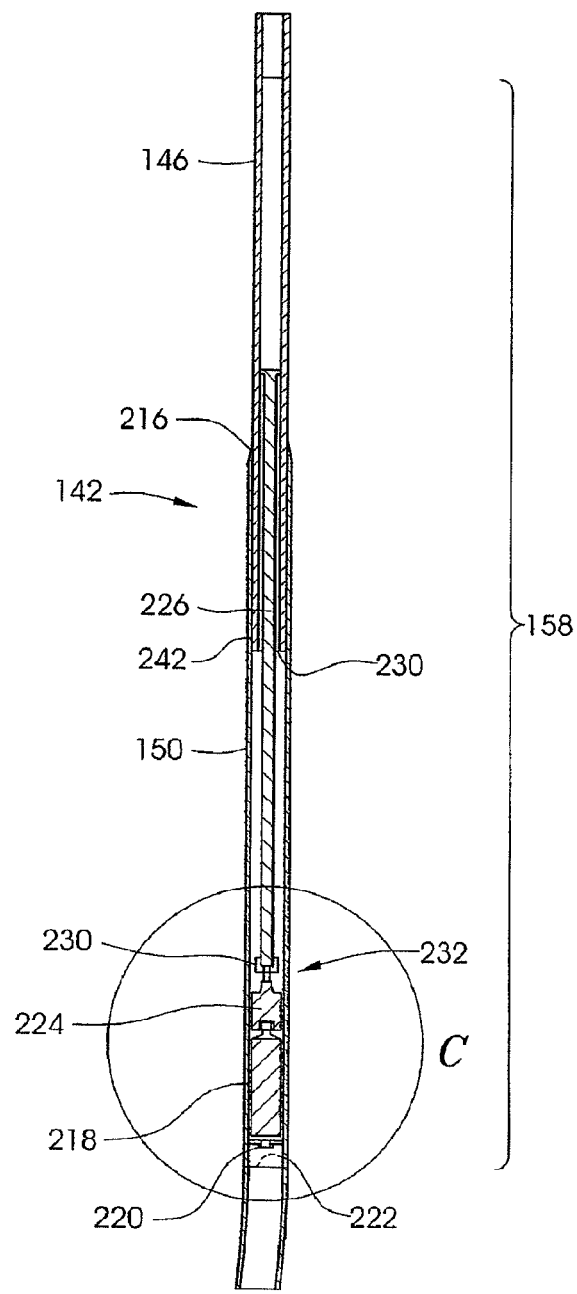
FIG. 6C illustrates a detailed view of portion B of FIG. 6A in accordance with an embodiment of the present invention.
Figure 6F:
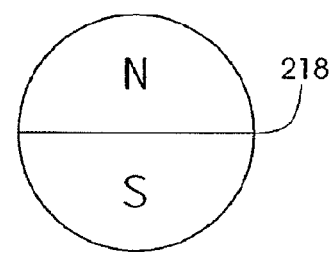
FIG. 6F illustrates an end view of a cylindrical magnetic member for adjusting a distraction device in accordance with an embodiment of the present invention.
Figure 6D:
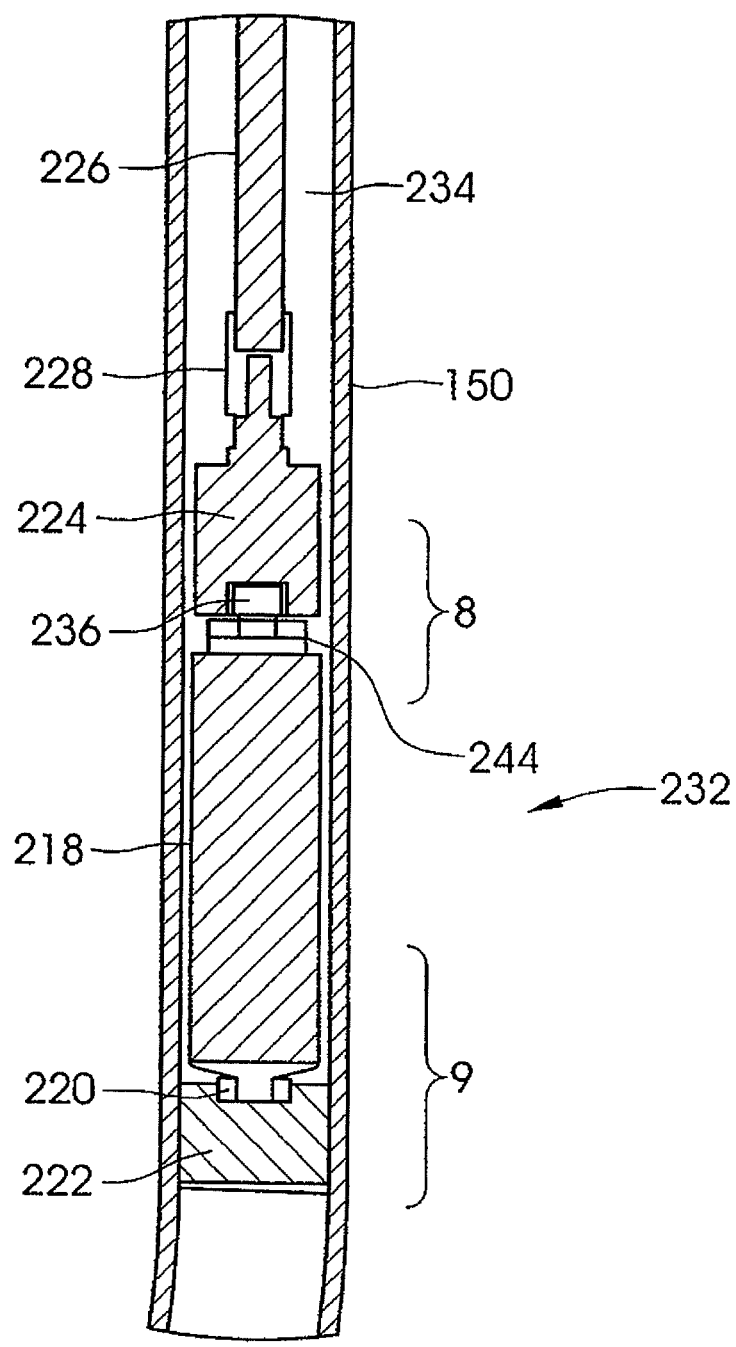
FIG. 6D illustrates a detailed view of portion C of FIG. 6C in accordance with an embodiment of the present invention.

FIG. 6C illustrates a sectional view of the adjustable portion 158 of the first adjustable rod 142. FIG. 6D illustrates a detail of the adjustment device 232. The first elongate element 146 is telescopically contained within the second elongate element 150. The cross-sectional shapes of the first elongate element 146 and the second elongate element 150 may be circular or non-circular, so that they cannot rotate with respect to each other (for example, a keyed configuration). One or both of the elongate elements 146, 150 may contain ribs along the cross section of the adjustable portion 158 in order to minimize contact surface area between the first elongate element 146 and the second elongate element 150 and thus lower frictional resistance. Beveled end piece 216 attached to the second elongate element 150 may serve two purposes. First, it allows for smooth insertion and no catching in tissue when the first adjustable rod 142 is inserted under the skin. Second, it serves as a low friction dynamic seal over the first elongate element 146. Magnetic element 218 comprises a cylindrical permanent magnet which is poled as shown in FIG. 6F. Alternatively, magnetic element 218, may be made from any of the materials described for magnetic member 200 in FIG. 6B. Magnetic element 218 is rotatably secured to an inner cavity 234 of second elongate element 150 by a housing, in this case an acoustic housing 222. A ball bearing 220 is illustrated at one end of the magnetic element 218 in order to reduce rotational friction. A second ball optional bearing (not shown) can be included on the opposite end of the magnetic element 218. Magnetic element 218 is rotated by an external adjustment device 1130 which produces a moving magnetic field.

Figure 6G:
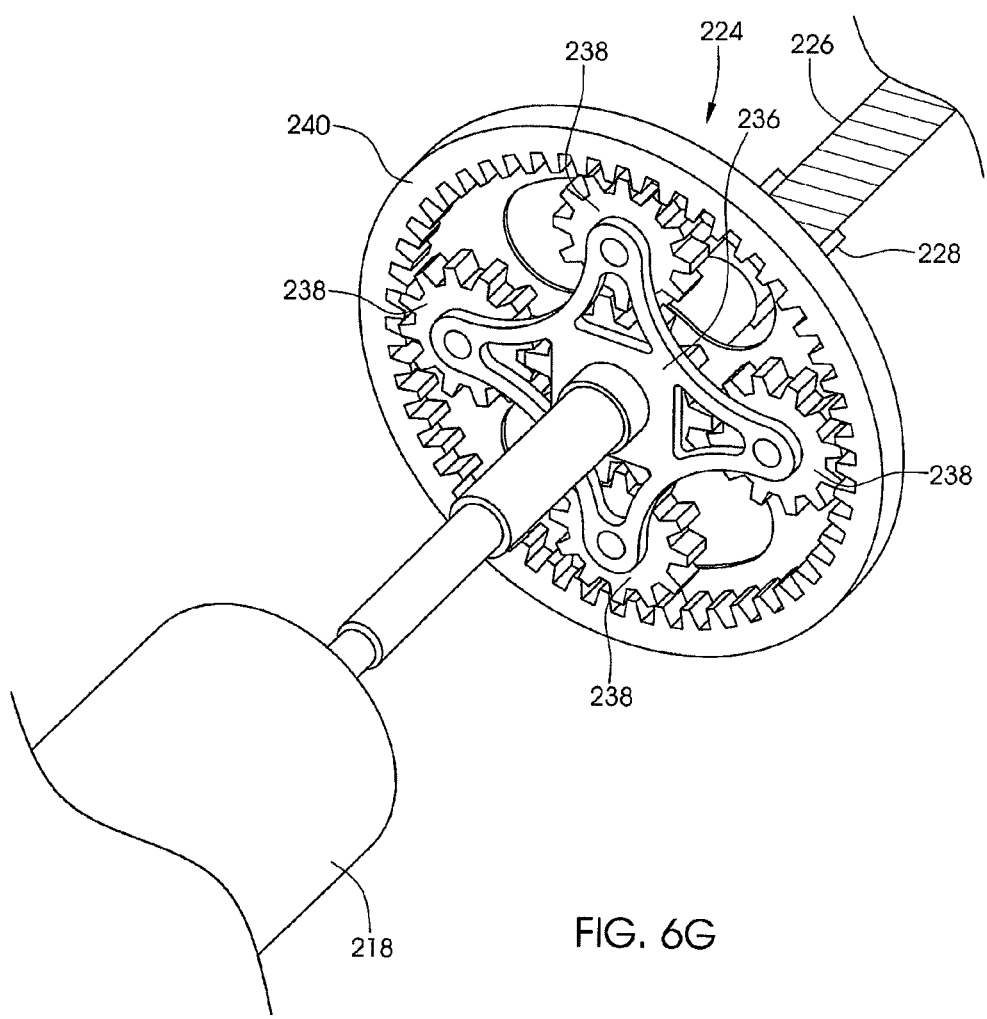
FIG. 6G illustrates the internal planetary gearing of portion of FIG. 7C in accordance with an embodiment of the present invention.

As seen in FIG. 6D, the magnetic element 218 is coupled to a planetary gear set 224, for example, having a 4:1, 16:1 or 64:1 gear reduction, or greater. The purpose of the gear reduction is two-fold. First, it allows the distraction device 140 to be adjusted with a smaller input torque requirement. Second, it adds precision to the adjustment, because a larger number of turns of the magnetic element 218 are required for each adjustment interval Planetary gear set 224 is shown in detail in FIG. 6G. Sun gear 236 is turned in a one-to-one fashion by the rotation of the magnetic element 218. Sun gear 236 engages a plurality of planetary gears 238 (in this case, four are pictured). Planetary gears 238 engage and turn ring gear 240 which is attached to a lead screw 226 via a coupling 228. The gear ratio is the number of teeth in the ring gear 240 divided by the number of teeth in the sun gear 236. For example if the ring gear 240 has four times as many teeth as the sun gear 236, then the gear ratio is 4:1. In this case, only 25% of the torque is required to drive the lead screw 226 as would have been required to drive it directly, ignoring the variance due to frictional factors. As lead screw 226 turns, it threadedly engages with female thread 230, disposed within end 242 of first elongate element 146. The pitch of lead screw 226 threads is preferably very line pitch, for example, 40 to 120, or more specifically 80 to 100 threads per inch, in order to minimize friction between the lead screw 226 and the female thread 230, and thus, minimize the required torque. The materials of the lead screw 226, the rods and other components may be made from non-magnetic, implantable materials such as Titanium or Titanium alloys such as Titanium-6% Al-4% V, although they may also be made from other magnetic materials such as stainless steel.

When the magnetic element 218 is rotated by the external adjustment device 1130, the drive train or chive element that is operatively coupled to the rotatable magnetic element 218 drives the lead screw 226 which changes the length of the adjustable portion 158 of the adjustable rod(s) 142, 144. Rotation of the magnetic element 218 in a first direction increases the distance between the anchors 161 located on opposing ends of the adjustable rod(s) 142, 144. Conversely, rotation of the magnetic element 218 in a second (opposing) direction decreases the distance between the anchors 161 located on opposing ends of the adjustable rod(s) 142, 144.

Currently, devices such as the VEPTR, which can be surgically adjusted, are used for early onset scoliosis patients, and their adjustability is used for the purpose of keeping up with the dimensional growth of the patient. It is a purpose of the present invention to create a device which can be non-invasively adjusted in early onset scoliosis patients, but additionally, in adolescent idiopathic scoliosis (AIS) patients and even adult scoliosis patients. The main purpose for the adjustment in AIS patients is to maintain a distraction force, which in a fusionless growing spine serves to steer growth in the desired manner. Currently, in fusionless surgery, non-adjustable distraction devices are actuated at very high distraction forces, because the physicians know that over time, growth and/or changes within the tissue, will cause this distraction force to lessen, possibly becoming less effective with time. Because of these high distraction forces, it is not uncommon to have rods break inside the patient, or for bone screws to become dislodged, due to the high stresses, it has been contemplated that the high forces that have been measured in some distraction devices of well over 100 pounds, are not necessary at any given time to provide correct growth guidance, and that a distraction force of below 45 pounds, and even as low as 20 pounds may be effective in maintaining the desired growth of the spine, especially the unfused spine. That is, as long as this force can be maintained, which is not currently possible in prior art devices without surgical intervention. The present invention allows this lower force to be continually maintained through non-invasive adjustment. The benefit is that lower stresses can be maintained on the bone screws, clamps, and other attachment means as well as the rods themselves, making for a more reliable and durable system. In addition, through the identification of an optimum distraction force, this desired force can be maintained throughout the treatment of the patient post-surgery, by frequent non-invasive adjustments, which can be performed in a doctor's or nurses office, by a physician or non-physician medical personnel, or even by the patient herself at home. In addition, by incorporating an optional force transducer, as part of the distraction device, that, is read telemetrically, each adjustment can be done to the precise desired distraction force. Additionally, a slip clutch 244, is in line with the magnetic element 218 can be pre-adjusted by the physician, or during the manufacturing process, so that during each adjustment, the adjustment stops when a critical torque (corresponding to the maximum desired distraction force) is reached. For example, the maximum desired distraction force may be set at 45 pounds. The slip clutch 244 is illustrated in FIG. 6D as being located between the magnetic element 218 and the planetary gear set 224, but it is within the scope of the invention that the slip clutch 244 may be located at any other step along the torque transmission chain.

Figure 9:
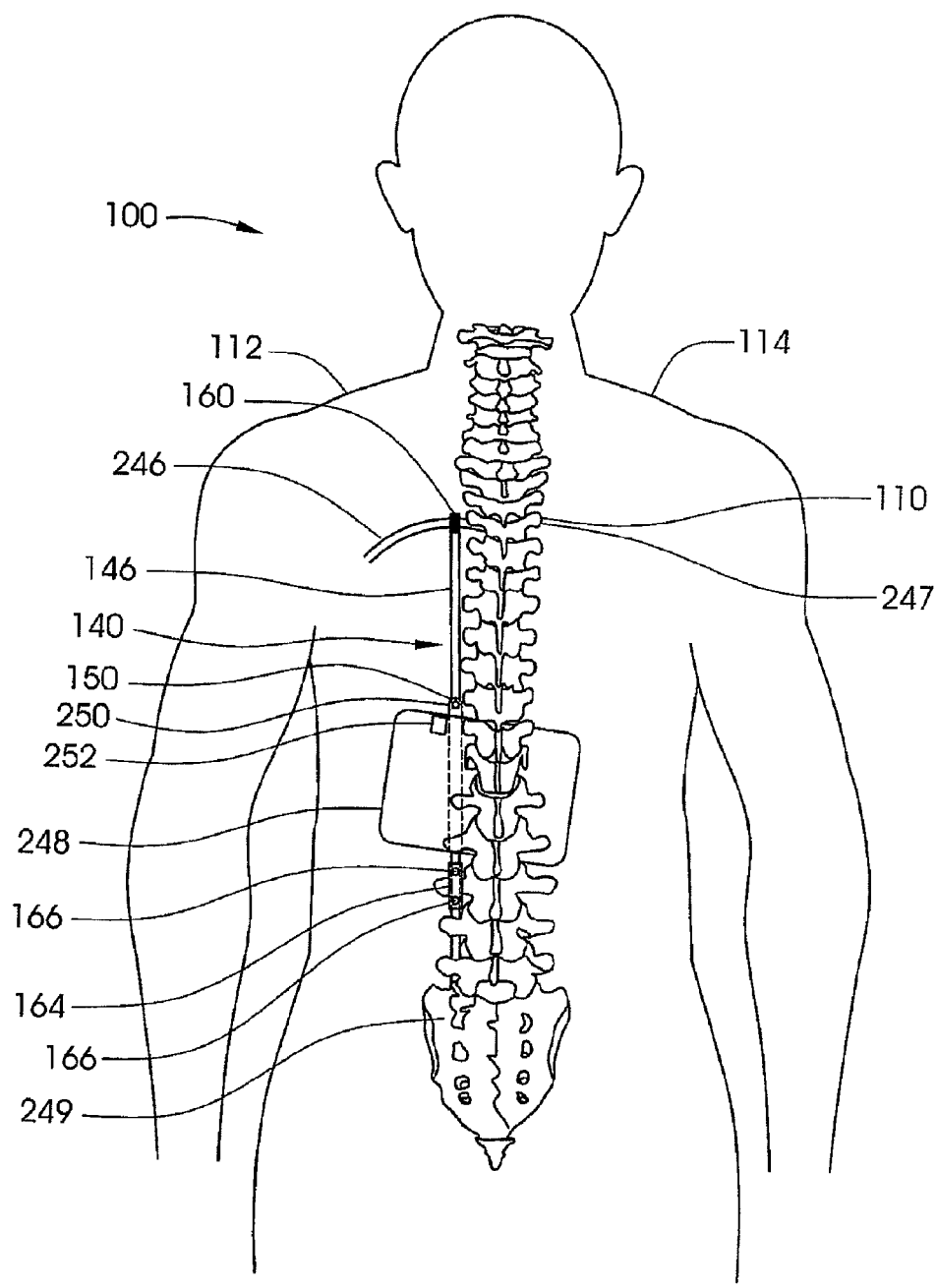
FIG. 9 illustrates a patient with an implanted distraction device during a non-invasive adjustment procedure.

FIG. 9 illustrates a patient 100 with a distraction device 140 implanted on the left side of the spine 110. Though the spine 110 is visible in FIG. 9 for reference, FIG. 9 is actually meant to depict a non-invasive adjustment procedure, and so the patient 100 would typically have all Incisions healed and could be wearing clothes. The clamp 160 of the distraction device 140 is secured to a rib 246 at its articulation with a thoracic vertebra 247. A bracket 164 is secured, in this case to a lumbar vertebra with screws 166. Alternatively, the bracket 164 may be secured, for example, to the sacrum 249. A radio frequency identification (RFID) chip 250 is optionally disposed on the second elongate element 150 of the distraction, device 140 in accordance with an embodiment of the present invention. An RFID (radio frequency identification) chip 250 may be implanted in a patient during the implantation of the distraction device 140. In certain embodiments, the RFID chip 250 may be implanted subcutaneously in a known location, such as a location near the distraction device 140. In other embodiments, the RFID chip 250 may be located on or within the distraction device 140. An external adjustment device 248 is depicted after being placed against the back of the patient 100. Upon the implantation of the distraction device 140 or after surgical recovery, the external adjustment device 248 stores patient information on the RFID chip 250, including the current size or setting of the distraction device 140, the amount adjusted, the serial number of the distraction device 140, the date of the implantation procedure, patient name, distraction force, adjustment torque, and identification. During subsequent adjustment procedures, the external adjustment device 248 may read the RFID chip 250 to determine information related to the patient, such as the current size or setting of the distraction device 140. At the end of the adjustment procedure, the external adjustment device 248 may store updated patient information, including the size or setting of the distraction device 140, to the RFID chip 250. An RFID antenna 252 in the external adjustment device 248 may be used to power the RFID chip in order facilitate the read and write functions.

Several techniques may be used to determine the adjustment setting (current size, distraction force or condition) of the distraction device 140. For example, the adjustment setting may be determined indirectly by the number of rotations of one of the rotating components of the external adjustment device 248. In certain embodiments, the adjustment setting may be determined, by the number of rotations of some dynamic component of the adjustable portion 158 of the distraction device 140, by the number of rotations of any one of the gears or shafts of the distraction device 140, or by the number of rotations of the magnetic element 218. In other embodiments, a feedback mechanism, such as a Hall effect device (two additional magnets that move axially in relation to each other as the lead screw 226 rotates and therefore as the distraction device changes its condition), may be used to determine the current adjustment setting of the distraction device 140. A strain gauge or force transducer disposed on a portion of the distraction device 140 may also be used as an implantable feedback device. For example, the strain gauge may be able to communicate wirelessly the actual distraction force applied to the spine by the distraction device 140. A wireless reader or the like (that also can inductively power the strain gauge) may be used to read the distraction forces. One exemplary strain gauge sensor is the EMBEDSENSE wireless sensor, available from MicroStrain, Inc. of Williston, Vt. 05495. The EMBEDSENSE wireless sensor uses an inductive link to receive power form an external coil and returns digital stain measurements wirelessly.

In still other embodiments, an optical encoder feedback mechanism may be used by placing an optical encoder in line with one of the rotating components of the adjustable portion 158 of the distraction device 140. A through-the-skin optical encoder is even envisioned that shines a light through the skin and fat and counts successive passes of one or more reflective stripes on the specific rotatable component. In other embodiments, the external adjustment device 248 may include an audio sensor to determine the current adjustment, setting of the distraction device 140. For example, the sensor may listen to the cycling sound of gearing, thus giving feedback information on the amount of total adjustment. An additional acoustic feedback device is discussed below.

It should be understood that any of the materials of the distraction device 140 can be made from radiopaque materials, so that the position, condition or alignment of the components may be seen during the initial surgical procedure, or during the subsequent adjustment procedures, by use of X-ray. For example, a circumferential notch or alternatively a circumferential bump disposed on the first or second elongate members 148, 146 may be used so that the distance between this notch or bump and some portion of the second elongate members 150, 152 can be measured easily via an X-ray.

It is conceived that the adjustment procedures would preferably take place every three to four weeks in the physicians' clinic. The adjustment may be done by an orthopedic surgeon, but because of the relative ease of the procedure because of the feedback capabilities of the system, the procedure may be done by a nurse practitioner, a physicians' assistant, a technician, or any other non-M.D. personnel. It is even conceived that the patient may have an external adjustment device 1130 at home and be able to adjust themselves at an even more frequent rate. The external adjustment device 1130 can be designed to transmit stored information over the phone to the physician's office. For example, adjustment dates or adjustment parameters such as distraction force or distraction distance.

FIG. 10 illustrates an external adjustment device 1130 which is one embodiment of an external adjustment device 248 according to one aspect of the invention. The external adjustment device 1130 may be used to externally impart rotational motion or "drive" a permanent magnet (e.g., magnetic element 218) located within the distraction device 140. The external adjustment device 1130 includes a motor 1132 that is used to impart rotational movement to two permanent magnets 1134, 1136. The two permanent magnets 1134, 1136 are located in the same driver 1130 and are configured for placement on the same side of the body of the patient or subject. The motor 1132 may include, for example, a DC powered motor or servo that is powered via one or more batteries (not shown) integrally contained within the external adjustment device 1130. Alternatively, the motor 1132 may be powered via a power cord or the like to an external power source. For example, the external power source may include one or more batteries or even an alternating current source that is converted to DC.

Still referring to FIG. 10, the two permanent magnets 1134, 1136 are preferably cylindrically-shaped permanent magnets. The permanent magnets may be made from, for example, a rare earth magnet material such as Neodymium-Iron-Boron (NdFeB) although other rare earth magnets are also possible. For example, each magnet 1134, 1136 may have a length of around 1.5 inches and a diameter of around 1.0 to 3.5 inches. Both magnets 1134, 1136 are diametrically magnetized (poles are perpendicular the long axis of each permanent magnet 1134, 1136). The magnets 1134, 1136 may be contained within a non-magnetic cover or housing 1137. In this regard, the magnets 1134, 1136 are able to rotate within the stationary housing 1137 that separates the magnets 1134, 1136 from the external environment. Preferably, the housing 1137 is rigid and relatively thin walled at least, at the portion directly covering the permanent magnets 1134, 1136, in order to minimize the gap between the permanent magnets 1134, 1136 and the internal magnet 1064 (as shown in FIGS. 13A-13D).

As seen in FIG. 10, the permanent magnets 1134, 1136 are rotationally mounted between opposing bases members 1138, 1140. Each magnet 1134, 1136 may include axles or spindles 1142, 1144 mounted on opposing axial faces of each magnet 1134, 1136. The axles 1142, 1144 may be mounted in respective bearings (not shown) that are mounted in the base members 1138, 1140. As seen in FIG. 10, driven pulleys 1150 are mounted on one set of axles 1142 and 1144. The driven pulleys 1150 may optionally include grooves or teeth 1152 that are used to engage with corresponding grooves or teeth 1156 (partially illustrated in FIG. 12) contained within a drive belt (indicated by path 1154).

Still referring to FIG. 10, the external adjustment device 1130 includes a drive transmission 1160 that includes the two driven pulleys 1150 along with a plurality of pulleys 1162A, 1162B, 1162C and rollers 1164A, 1164B, 1164C on which the drive belt 1154 is mounted. The pulleys 1162A, 1162B, 1162C may optionally include grooves or teeth 1166 used for gripping corresponding grooves or teeth 1156 of the drive belt 1154. Pulleys 1162A, 1162B, 1162C and rollers 1164A, 1164B, 1164C may be mounted on respective bearings (not shown). As seen in FIG. 10, pulley 1162B is mechanically coupled to the drive shaft (not shown) of the motor 1132. The pulley 1162B may be mounted directly to the drive shaft or, alternatively, may be coupled through appropriate gearing. One roller 1164B is mounted on a biased arm 1170 and thus provides tension to the belt 1154. The various pulleys 1150, 1162A, 1162B, 1162C and rollers 1164A, 1164B, 1164C along with the drive belt 1154 may be contained within a cover or housing 1172 that is mounted to the base 1138 (as seen in FIG. 12). For safety and convenience, it may be desired for the external adjustment device 1130 to have a removable safety cover that would be placed over the portion containing the permanent magnets 1134, 1136, for example during storage, so that the high magnetic field cannot come closely in contact with anything that would be strongly attracted to it or damaged by it.

As seen in FIGS. 10 and 11, rotational movement of the pulley 1162B causes the drive belt 1154 to move around the various pulleys 1150, 1162A, 1162B, 1162C and rollers 1164A, 1164B, 1164C, in this regard, rotational movement of the motor 1132 is translated into rotational movement of the two permanent magnets 1134, 1136 via the drive transmission 1160. In one aspect of the invention, the base members 1138, 1140 are cut so as to form a recess 1174 that is located between the two magnets 1134, 1136. During use, the external adjustment device 1130 is pressed against the skin of a patient, or against the clothing which covers the skin (e.g., the external adjustment device 1130 may be used through clothing so the patient may not need to undress). The recess 1174 allows skin as well as the underlying tissue to gather or compress within the recessed region 1174 as seen in FIGS. 13A and 13B. This advantageously reduces the overall distance between the external drive magnets 1134, 1136 and the magnet 1064 contained within the distraction device 140. By reducing the distance, this means that the externally located magnets 1134, 1136 and/or the internal magnet 1064 may be made smaller. This is especially useful in the case of an obese patient.

In one embodiment, the two permanent magnets 1134, 1136 are configured to rotate at the same angular velocity. In another embodiment, the two permanent magnets 1134, 1136 each have at least one north pole and at least one south pole, and the external adjustment device 1130 is configured to rotate the first magnet 1134 and the second magnet 1136 such that the angular location of the at least one north pole of the first magnet 1134 is substantially equal to the angular location of the at least one south pole of the second magnet 1136 through a full rotation of the first and second magnets 1134, 1136.

FIGS. 13A and 13B illustrate cross-sectional views of the patient having an implanted distraction device 140 containing an internal magnet 1064. For sake of clarity, the first and second elongate members 146, 150 have been removed to illustrate the relationship between the external adjustment device 1130 and the rotationally-driven internal magnet 1064. The internal magnet 1064 is seen disposed on one side of a vertebra 1185. Further, the internal magnet 1064 is seen being outside or external with respect to the fascia 1184 and muscle 1186 of the subject. FIGS. 13A and 13B illustrate an obese patient in which skin and other tissue gather within the recess 1174. It should be understood that obese Adolescent Idiopathic Scoliosis patients are rare, and FIGS. 13A and 13B generally indicate a worst-case situation but as seen in FIGS. 13A and 13B the excess skin and other tissue is easily accommodated within the recess 1174 to enable close positioning between the internal magnet 1064 and the external drive magnets 1134, 1136. For most AIS patients, the air gap or distance between the internal magnet 1064 and the external drive magnets 1134, 1136 is generally one inch or less. In FIGS. 13A through 13D, the internal magnet 1064 is depicted somewhat larger than its size in the preferred embodiment, in order for its poles to be more clearly visible.

Still referring to FIGS. 10 and 11, the external adjustment device 1130 preferably includes an encoder 1175 that is used to accurately and precisely measure the degree of movement (e.g., rotational) of the external magnets 1134, 1136. In one embodiment, an encoder 1175 is mounted on the base member 1138 and includes a light source 1176 and a light receiver 1178. The light source 1176 may include an LED which is pointed or directed toward pulley 1162C. Similarly, the light receiver 1178 may be directed toward the pulley 1162C. The pulley 1162C includes a number of reflective markers 1177 regularly spaced about the periphery of the pulley 1162C. Depending on the rotational orientation of the pulley 1162C, light is either reflected or not reflected back onto the light receiver 1178. The digital on/off signal generated by the light receiver 1178 can then be used to determine the rotational speed and displacement of the external magnets 1134, 1136.

FIGS. 13A, 13B, 13C, and 13D illustrate the progression of the external magnets 1134, 1136 and the internal magnet 1064 that is located within the distraction device 140 during use. Internal magnet 1064 is shown for illustration purposes. Internal magnet 1064 is one possible embodiment of the magnetic element 218 described herein. FIGS. 13A, 13B, 13C, and 13D illustrate the external adjustment device 1130 being disposed against the external surface of the patient's skin 1180 adjacent the spine (not shown for clarity sake). In the non-invasive adjustment procedure depicted, the patient 100 lies in a prone position, and the external adjustment device 1130 is placed upon the patient's back. However, the adjustment is conceived possible with the patient in supine, standing or positions. The external adjustment device 1130 is placed against the skin 1180 in this manner to remotely rotate the internal magnet 1064. As explained herein, rotation of the internal magnet 1064 is translated into linear motion via the adjustment device 232 to controllably adjust the distraction device 140.

As seen in FIGS. 13A, 13B, 13C and 13D, the external adjustment device 1130 may be pressed down on the patient's skin 1180 with some degree of force such that skin 1180 and other tissue such as the underlying layer of fat 1182 are pressed or forced into the recess 1174 of the external adjustment device 1130. FIGS. 13A, 13B, 13C, and 13D show the magnetic orientation of the internal magnet 1064 as it undergoes a full rotation in response to movement of the permanent magnets 1134, 1136 of the external adjustment device 1130.

With reference to FIG. 13A, the internal magnet 1064 is shown being oriented with respect to the two permanent magnets 1134, 1136 via an angle θ. This angle θ may depend on a number of factors including, for instance, the separation distance between the two permanent magnets 1134, 1136, the location or depth of where the implantable interface 1104 is located, the degree of force at which the external adjustment device 1130 is pushed against the patient's skin. Generally in applications including some obese patients, the angle θ should be at or around 90° to achieve maximum drivability (e.g., torque). The inventors have calculated that in the AIS application, where there are few obese patients, an angle of about 70° is preferred for the majority of patients when the permanent magnets 1134, 1136 have an outer diameter of about three (3.0) inches.

FIG. 13A illustrates the initial position of the two permanent magnets 1134, 1136 and the internal magnet 1064. This represents the initial or starting location (e.g., 0° position as indicated). Of course, it should be understood that, during actual use, the particular orientation of the two permanent magnets 1134, 1136 and the internal magnet 1064 will vary and not likely will have the stalling orientation as illustrated in FIG. 13A. In the starting location illustrated in FIG. 13A, the two permanent magnets 1134, 1136 are oriented with their poles in an N-S/S-N arrangement. The internal magnet 1064 is, however, oriented generally perpendicular to the poles of fire two permanent magnets 1134, 1136.

FIG. 13B illustrates the orientation of the two permanent magnets 1134, 1136 and the internal magnet 1064 after the two permanent magnets 1134, 1136 have rotated through 90°. The two permanent magnets 1134, 1136 rotate in the direction of arrow A (e.g., clockwise) while the internal magnet 1064 rotates in the opposite direction (e.g., counter clockwise) represented by arrow B. It should be understood that the two permanent magnets 1134, 1136 may rotate in the counter clockwise direction while the internal magnet 1064 may rotate in the clockwise direction. Rotation of the two permanent magnets 1134, 1136 and the internal magnet 1064 continues as represented by the 180° and 270° orientations as illustrated in FIGS. 13C and 13D. Rotation continues until the starting position (0°) is reached again.

During operation of the external adjustment device 1130, the permanent magnets 1134, 1136 may be driven to rotate the internal magnet 1064 through one or more full rotations in either direction to increase or decrease distraction of the distraction device 140 as needed. Of course, the permanent magnets 1134, 1136 may be driven to rotate the internal magnet 1064 through a partial rotation as well (e.g., ¼, ⅛, 1/16, etc.). The use of two magnets 1134, 1136 is preferred over a single external magnet because the driven magnet 1064 may not be oriented perfectly at the start of rotation, so one external magnet 1134, 1136 may not be able to deliver its maximum torque, which depends on the orientation of the internal driven magnet 1064 to some degree. However, when two (2) external magnets (1134, 1136) are used, one of the two 1134 or 1136 will have an orientation relative to the internal driven magnet 1064 that is better or more optimal than the other. In addition, the torques imparted by each external magnet 1134, 1136 are additive. In prior art magnetically driven devices, the external driving device is at the mercy of the particular orientation of the internal driven magnet. The two-magnet embodiment described herein is able to guarantee a larger driving torque—as much as 75% more than a one-magnet embodiment in the AIS application—and thus the internal driven magnet 1064 can be designed smaller in dimension, and less massive. A smaller internal driven magnet 1064 will have a smaller image artifact when performing MRI (Magnetic Resonance Imaging), especially important when using pulse sequences such as gradient echo, which is commonly used in breast imaging, and leads to the largest artifact from implanted magnets. In certain configurations, it may even be optimal to use three or more external magnets, including one or more magnets each on two different sides of the body (for example front and back).

While the external adjustment device 1130 and adjustment device 232 have generally been described as functioning using rotational movement of driving elements (i.e., magnetic elements) it should be understood that cyclic or non-rotational movement can also be used to drive or adjust the distraction device 140. For instance, cyclic movement of driven magnet 640, magnetic element 218, internal magnet 1064, internally located driven magnet 1402, cylindrical magnet 394, hollow magnet 564, magnet 576, magnet 262, magnets 618, 620, and magnet 1302 may be used to drive or adjust the distraction device 140. Cyclic movement includes partial rotational movement (e.g., rotational movement that is less than a full revolution). Cyclic movement of one or more of the external magnets 624, 626, 1134, 1136 may also be employed.

In still another alternative, linear or sliding motion back-and-forth may also be used to adjust the distraction device 140. In this regard, a single magnet located internal to the patient that slides back-and-forth on a slide or other base can be used to adjust the distraction device 140 using a ratchet-type device. The sliding, internal magnet may be driven via one or more externally-located permanent/electromagnets that slides or moves laterally (or moves the magnetic field) in a similar back-and-forth manner. Rotational movement of the externally-located magnetic element(s) may also be used to drive the internal magnet. The internal magnet may alternatively be able to rotate back-and-forth, thus adjusting the distraction device 140 using a ratchet-type device.

In still another alternative, permanent magnets may be located on a pivoting member that pivots back and forth (like a teeter-totter) about, a pivot point. For example, a first permanent magnet having a North pole oriented in a first direction may be located at one end of the pivoting member while a permanent magnet having a South pole oriented in the first direction is located at the other end of the pivoting member. A ratchet-type device may be used to translate the pivoting movement into linear movement that can actuate or adjust, the distraction device 140. The first and second internally-located permanent magnets may be driven by one or more externally located magnetic elements (either permanent or electromagnets). External motion of the electric field by linear or even rotational movement may be used to the drive the pivoting member.

Two different models of internal driven magnets were constructed, each from a different Neodymium-Iron-Boron Grade. Both magnets had identical dimensions (0.275" diameter, 0.395" long). One magnet was a grade of approximately N38 and the other was a grade of N50. Both magnets were approximately 2.9 grams in mass. A 1" diameter cylindrical permanent magnet (grade N50 Neodymium-Iron-Boron) was attached to a torque gauge and the peak coupling torque (in inch-ounces) between it and each of the internal drive magnet models was measured for three different angular orientations for the cylindrical permanent magnet, in relation to the internal driven magnet. All magnets were two pole (as in FIGS. 13A-13D). Each of the internal driven magnets was tested individually. The orientation was either 0° (worst case coupling torque), 45° or 90° (best case coupling torque). The data for a one inch air gap (separation between magnets) is listed below in Table 1 below. A one (1) inch air gap is an expected worst case separation in the clinical application of adolescent idiopathic scoliosis. The effect of using two external 1" diameter permanent magnets (as in FIGS. 13A-13D) is shown by addition of the values for the worst case (0°) and best case (90°) orientations.

TABLE 1

Peak Coupling Torque (oz-in) at 1" Air Gap

| Internal driven magnet | 0° orientation of single external magnet | 45° orientation of single external magnet | 90° orientation of single external magnet | Two external magnets (0° orientation + 90° orientation) |
|---|---|---|---|---|
| Grade 38 (approx) | 1.37 | 1.92 | 2.47 | 3.84 |
| Grade 50 | 1.70 | 2.04 | 2.80 | 4.50 |

It can be clearly seen that the additive use of two external permanent magnets, especially if synchronised in the orientation shown in FIGS. 13A-13D, delivers significantly more torque than a single external magnet in any orientation. For the data generated using the 50 grade internal driven magnet, the peak coupling torque using two external permanent magnets was 4.50 ounce-inches, 60.7% greater than a single external permanent magnet oriented at the ideal 90° in relation to the internal driven magnet, and 164.7% greater than a single external permanent magnet oriented at the worst case 0°. This significant increase in torque achieved by using two external permanent magnets, makes it possible to incorporate an especially small internal driven magnet, (e.g., less man three grams) into the design of the scoliosis treatment implant, or any implant for manipulating one or more bones or a portion of the skeletal system. For example, the use of two external permanent magnets may impart a coupling torque of at least 3.0 inch-ounces to the internal magnet at a separation distance of around 1.0 inches.

In a gradient echo MRI scan of the breast in a 1.5 Tesla MRI scanner using standard breast imaging coils, a 2.9 gram N50 grade magnet having a 0.275 inch diameter and 0.295" length implanted in the mid-thorax creates an MRI artifact which is small enough to allow full imaging of the breasts. Using the dual 1" diameter external permanent magnets 1134, 1136 as for the external adjustment device 1130, and using the grade 50 for the internal driven magnet 1064 having a mass of 2.9 grams, the 4.50 ounce-inch torque delivered to the magnet will turn a 80 threads per inch lead screw mounted on ball bearing in a sufficient manner to apply a distraction force of approximately 11 pounds. If a 4:1 reduction planetary gear set is incorporated into the design—for example, between the internal driven magnet 1064 and the lead screw 226—then a distraction force of approximately 44 pounds may be delivered. In the system contemplated by this invention, in which several gradual non-invasive adjustments are made, distraction forces on this order (40 to 45 pounds) will be sufficient. In fact, the slip clutch 244 can either be adjusted in tire fabrication of the scoliosis implant or can be adjusted by the implanting physician, so that the slip clutch 244 slips at either a maximum threshold torque (to save the materials of the implant from being damaged or pulling out of the bone by too high a distraction force) or at desired threshold torque (at which the desired distraction force is generated).

The maximum threshold torque corresponds to a critical distraction force, and the desired threshold torque corresponds to a desired distraction force. A critical distraction force may correspond to a force at which anchors such as hooks or screws may cause damage to the bone. For example, one critical distraction force is 100 pounds, which in one embodiment of the invention corresponds to a critical threshold slip torque of 41.7 ounce-inches (if no gear reduction, and a 80 threads per inch lead screw is used), 10.4 ounce-inches (if a 4:1 gear reduction and a 80 threads per inch lead screw is used) or 2.6 ounce-inches (if a 16:1 gear reduction and a 80 threads per inch lead screw is used). Similarly, one desired distraction force is 45 pounds, which in one embodiment of the invention corresponds to a desired threshold slip torque of 18.75 ounce-inches (if no gear reduction and a 80 threads per inch lead screw is used) or 4.69 ounce-inches (if a 4:1 gear reduction and a 80 threads per inch lead screw is used). If a desired distraction force is 20 pounds, then in one embodiment of the invention this corresponds to a desired threshold slip torque of 8.33 ounce-inches (if no gear reduction and a 80 threads per inch lead screw is used) or 2.08 ounce-inches (if a 4:1 gear reduction and a 80 threads per inch lead screw is used). In one aspect, the desired threshold distraction is between 2 inch-ounces and 42 inch-ounces. In another aspect, the desired threshold distraction is between 2 inch-ounces and 19 Inch-ounces. In still another aspect, the desired threshold distraction is between 2 Inch-ounces and 8.5 inch-ounces.

Other distraction devices have been proposed which incorporate a small implantable motor to effect the distraction. The 2.9 gram cylindrical magnet 1064 described as part of the present invention is significantly smaller than the smallest motor which would be feasible in the distraction application, considering torque requirements, etc. In addition, the cost of the magnet 1064 is significantly less than that of a micromotor. The magnet 1064 is also very reliable in relation to a micromotor. The main possible failure would be the loss of the magnetic field, however the inventors have demonstrated that the inventive 2.9 gram magnet 1064 can be placed into the center of a 3.0 Tesla MRI magnet without a significant loss in magnetism. It can also be exposed to temperatures in excess of those used in steam sterilization, for example, without a significant loss of magnetism. Generally, the internal magnet 1064 should be grade N30 or higher, or even grade N48 or higher. While the 2.9 gram cylindrical magnet 1064 has the advantage of being particularly small, in other embodiments, the cylindrical magnet 1064 may have a weight of less than about 10 grams or less than about 6.0 grams. Similarly, the first and second external magnets 1134, 1136 may be a rare earth permanent magnets such as, for instance, Neodymium-Iron-Boron. In addition, the first and second external magnets 1134, 1136 may be grade N30 or higher, or even grade N48 or higher.

Figure 14:
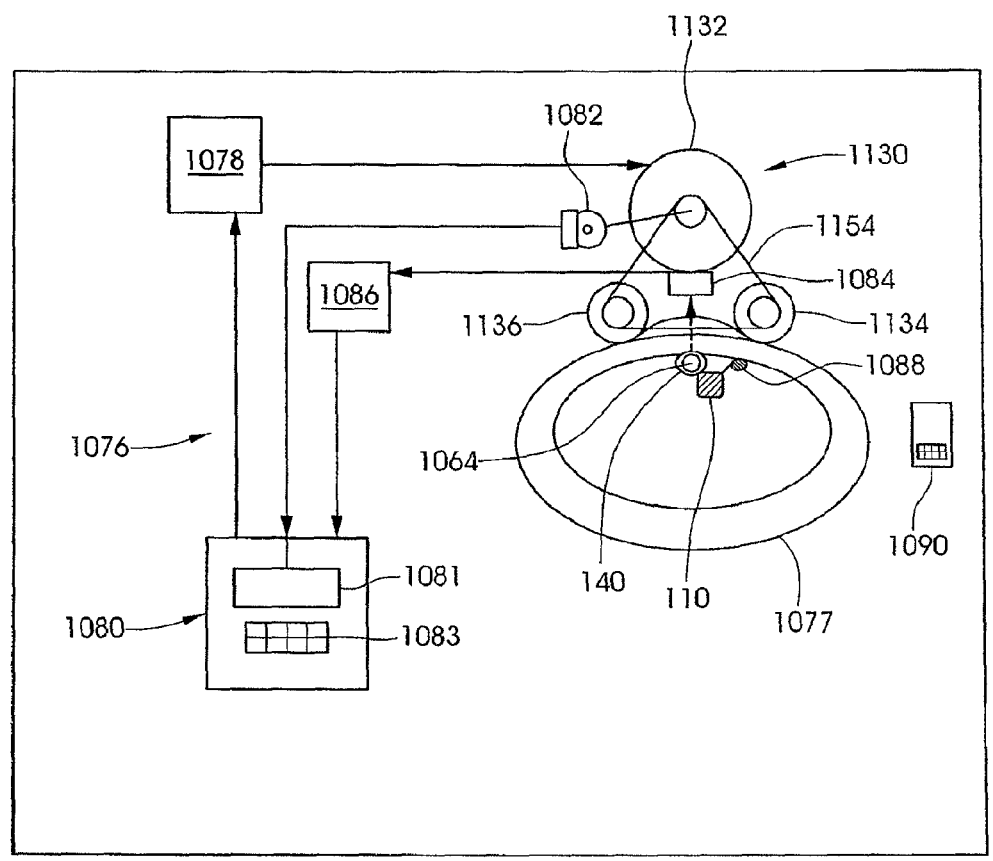
FIG. 14 schematically illustrates a system for driving the external adjustment device according to one embodiment.

FIG. 14 illustrates a system 1076 according to one aspect of the invention for driving the external adjustment device 1130. FIG. 14 illustrates the external adjustment device 1130 pressed against the surface of a patient 1077 (torso face down shown in cross-section). The portion of the distraction device 140 containing the internal driven, magnet 1064 is illustrated. The permanent magnet (e.g., the driven magnet 1064) that is located within the distraction device 140 located inside the patient 1077 is magnetically coupled through the patient's skin and other tissue to the two external magnets 1134, 1136 located in the external adjustment device 1130. As explained herein, one rotation of the external magnets 1134, 1136 causes a corresponding single rotation of the driven magnet 1064 located within the distraction device 140. Turning the driven magnet 1064 in one direction causes the distraction device 140 to lengthen, or increase distraction force while turning in the opposite direction causes the distraction device 140 to shorten, or decrease distraction force. Changes to the distraction device 140 are directly related to the number of turns of the driven magnet 1064.

The motor 1132 of the external adjustment device 1130 is controlled via a motor control circuit 1078 operatively connected to a programmable logic controller (PLC) 1080. The PLC 1080 outputs an analog signal to the motor control circuit 1078 that is proportional to the desired speed of the motor 1132. The PLC 1080 may also select the rotational direction of the motor 1132 (i.e., forward or reverse). In one aspect, the PLC 1080 receives an input signal from a shaft encoder 1082 that is used to identify with high precision and accuracy the exact relative position of the external magnets 1134, 1136. For example, the shaft encoder 1082 may be an encoder 1175 as described in FIGS. 10-11. In one embodiment, the signal is a pulsed, two channel quadrature signal that represents the angular position of the external magnets 1134, 1136. The PLC 1080 may include a built in screen or display 1081 that can display messages, warnings, and the like. The PLC 1080 may optionally include a keyboard 1083 or other input device for entering data. The PLC 1080 may be incorporated directly into the external adjustment device 1130 or it may be a separate component that is electrically connected to the main external adjustment device 1130.

In one aspect of the invention, a sensor 1084 is incorporated into the external adjustment device 1130 that is able to sense or determine the rotational or angular position of the driven magnet 1064. The sensor 1084 may acquire positional information using, for example, sound waves, ultrasonic waves, light, radiation, or even changes or perturbations in the magnetic or electromagnetic field between the driven magnet 1064 and the external magnets 1134, 1136. For example, the sensor 1084 may detect photons or light that is reflected from the driven magnet 1064 or a coupled structure (e.g., rotor) that is attached thereto. For example, light may be passed through the patient's skin and other tissue at wavelength(s) conducive for passage through tissue. Portions of the driven magnet 1064 or associated structure may include a reflective surface that reflects light back outside the patient as the driven magnet 1064 moves. The reflected light can then be detected by the sensor 1084 which may include, for example, a photodetector or the like.

In another aspect, the sensor 1084 may operate on the Hall effect, wherein two additional magnets are located within the implantable assembly. The additional magnets move axially in relation to each other as the driven assembly rotates and therefore as the distraction increases or decreases, allowing the determination of the current size of the restriction device.

In the embodiment of FIG. 14, the sensor 1084 is a microphone disposed on the external adjustment device 1130. For instance, the microphone sensor 1084 may be disposed in the recessed portion 1174 of the external adjustment device 1130. The output of the microphone sensor 1084 is directed to a signal processing circuit 1086 that amplifies and filters the detected acoustic signal. In this regard, the acoustic signal may include a "click" or other noise that is periodically generated by rotation of the driven magnet 1064. For example, the driven magnet 1064 may click every time a full rotation is made. The pitch (frequency) of the click may differ depending on the direction of rotation. For example, rotation in one direction (e.g., lengthening) may produce a low pitch while rotation in the other direction (e.g., shortening) may produce a higher pitch signal (or vice versa). The amplified and filtered signal from the signal processing circuit 1086 can then pass to the PLC 1080.

During operation of the system 1076, each patient will have a number or indicia that correspond to the adjustment setting or size of their distraction device 140. This number can be stored on an optional storage device 1088 (as shown in FIG. 14) that is carried by the patient (e.g., memory card, magnetic card, or the like) or is integrally formed with the distraction device 140. For example, a RFID tag 1088 implanted either as part of the system or separately may be disposed inside the patient (e.g., subcutaneously or as part of the device) and can be read and written via an antenna 1090 to update the current size of the distraction device 140. In one aspect, the PLC 1080 has the ability to read the current number corresponding to the size or setting of the distraction device 140 from the storage device 1088. The PLC 1080 may also be able to write the adjusted or more updated current size or setting of the distraction device 140 to the storage device 1088. Of course, the current size may recorded manually in the patient's medical records (e.g., chart, card or electronic patient record) that is then viewed and altered, as appropriate, each time the patient visits his or her physician.

The patient, therefore, carries their medical record with them, and if, for example, they are in another location, or even country, and need to be adjusted, the RFID tag 1088 has all of the information needed. Additionally, the RFID tag 1088 may be used as a security device. For example, the RFID tag 1088 may be used to allow only physicians to adjust the distraction device 140 and not patients. Alternatively, the RFID tag 1088 may be used to allow only certain models or makes of distraction devices to be adjusted by a specific model or serial number of external adjustment device 1130.

In one aspect, tire current size or setting of the distraction device 140 is input into the PLC 1080. This may be done automatically or through, manual input via, for instance, the keyboard 1083 that is associated with the PLC 1080. The PLC 1080 thus knows the patient's starting point. If the patient's records are lost, the length of the distraction device may be measured by X-ray and the PLC 1080 may be manually programmed to this known starting point.

The external adjustment device 1130 is commanded to make an adjustment. This may be accomplished via a pre-set command entered into the PLC 1080 (e.g., "increase distraction displacement of distraction device 140 by 0.5 cm" or "increase distraction force of distraction device 140 to 20 pounds"). The PLC 1080 configures the proper direction for the motor 1132 and starts rotation of the motor 1132. As the motor 1132 spins, the encoder 1082 is able to continuously monitor the shaft position of the motor directly, as is shown in FIG. 14, or through another shaft or surface that is mechanically coupled to the motor 1132. For example, the encoder 1082 may read the position of markings 1177 located on the exterior of a pulley 1162C like that disclosed in FIG. 10. Every rotation or partial rotation of the motor 1132 can then be counted and used to calculate the adjusted or new size or setting of the distraction device 140.

The sensor 1084, which may include a microphone sensor 1084, may be monitored continuously. For example, every rotation of the motor 1132 should generate the appropriate number and pitch of clicks generated by rotation of the permanent magnet inside the distraction device 140. If the motor 1132 turns a full revolution but no clicks are sensed, the magnetic coupling may have been lost and an error message may be displayed to the operator on a display 1081 of the PLC 1080. Similarly, an error message may be displayed on the display 1081 if the sensor 1084 acquires the wrong pitch of the auditory signal (e.g., the sensor 1084 detects a shortening pitch but the external adjustment device 1130 was configured to lengthen).

FIGS. 15 through 30 schematically illustrate an acoustic indicator housing 1304 and a driven magnet 1302 as the driven magnet 1302 is rotated in both the clockwise directions (arrow A) and counter-clockwise directions (arrow B). It should be understood that while a description is given with respect to driven magnet 1302, the acoustic sensing features may also apply to magnetic element 218 of FIGS. 6C-6G, the internal magnet 1064 of FIGS. 13A-13D, 14, the internally located driven magnet 1402 of FIG. 35, cylindrical magnet 394 of FIGS. 41,42, and 44, the hollow magnet. 564 of FIG. 48, magnet 576 of FIG. 50, magnet 262 of FIG. 53, aid magnets 618, 620 of FIG. 51 magnet 640 of FIG. 52, or even magnetic member 200 of FIG. 6B (these various implementations of driven magnets may be referred to, in some instances, as magnetic elements). The acoustic indicator housing 1304 is illustrated in an annular configuration with respect to the circumference of the driven magnet 1302, but an alternative relationship is contemplated, for example wherein the outer diameter of the acoustic indicator housing 1304 is substantially the same as the outer diameter of the driven magnet 1302, and they are oriental with an end-to-end axial relationship instead of an annular relationship. Acoustic indicator housing 1304 is one possible embodiment of the acoustic housing 222 of FIG. 6C and FIG. 6D. The acoustic indicator housing 1304 is used to create an acoustic signal (e.g., a click) that can be used to count rotational movement of the driven magnet 1302 and also determine its rotational direction. An acoustic signal (i.e., sound) is generated when a magnetic ball 1306 strikes either a first impact surface 1308 or a second impact surface 1310. FIGS. 15-22 illustrate rotation of the driven magnet 1302 in the clockwise direction (arrow A) while FIGS. 23-30 illustrate rotation of the driven magnet 1302 in the counter-clockwise direction (arrow B). When the driven magnet 1302 is rotated in the clockwise direction, the magnetic ball 1306 strikes the first impact surface 1308 two times (2×) per full rotation, with the first impact surface 1308 producing sound with a first amplitude and/or frequency. When the driven magnet 1302 is rotated in the counter-clockwise direction, the magnetic ball 1306 strikes the second impact surface 1310 two times (2×) per full rotation, with the second impact surface 1310 producing sound with a second amplitude and/or frequency.

As illustrated in FIGS. 15-30, the first impact surface 1308 is thinner than the second impact surface 1310, and thus, the first impact surface 1308 is configured, to resonate at a higher frequency than the second impact surface 1310. Alternatively, the difference in frequency can be achieved by making the first impact surface 1308 from a different material than the second impact surface 1310. Alternatively, the amplitude of acoustic signal generated by the magnetic ball 1306 hitting the first and second impact surfaces 1308, 1310 may be used to discriminate rotational direction. For example, clockwise rotation may produce a relatively loud click while counter-clockwise rotation may produce a relatively quiet click.

The magnetic ball 1306 is made from a magnetic material, for example 400 series stainless steel. The magnetic ball 1306 is attracted to both a south pole 1314 of the driven magnet 1302 and a north pole 1316 of tire driven magnet 1302. As seen in FIG. 15, the driven magnet 1302 begins to rotate in the clockwise direction (arrow A). As pictured, the starting point of the magnetic ball 1306 is adjacent to the north pole 1316 of the magnet 1302. As seen in FIG. 16, as the magnet 1302 rotates, the magnetic ball 1306 follows tire north pole 1316. This continues until, as shown in FIG. 17, the magnetic ball 1306 is stopped by the second impact surface 1310. Now, as seen in FIG. 18, the magnetic ball 1306 is trapped against the second impact surface 1310, while the driven magnet 1302 continues to rotate. The magnetic ball 1306 may roll at this point, but it is forced against the second impact surface 1310 by its attraction to the north pole 1316 of the magnet 1302, until the south pole 1314 becomes substantially closer to the magnetic ball 1306 as shown in FIG. 19, at which point the magnetic ball 1306 accelerates towards the first impact surface 1308 in the direction of arrow α, thereby hitting it (as seen in FIG. 20) and creating an acoustic signal or sound having a greater intensity than when the magnetic ball 1306 was stopped by the second impact surface 1310. Now, as the driven magnet 1302 continues to turn, the magnetic bah 1306 follows the south pole 1314 of the driven magnet 1302 as seen in FIG. 21, and continues to follow the south pole 1314 until the magnetic ball 1306 is stopped by the second impact surface 1310 as seen in FIG. 22.

Figure 27:
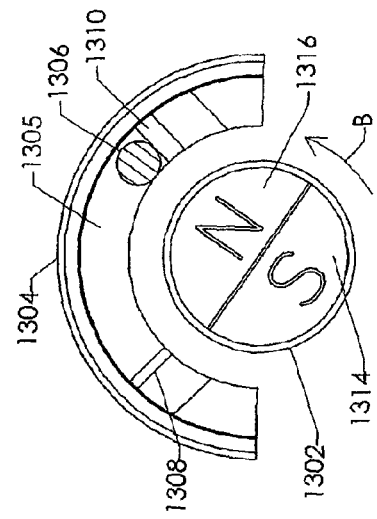
Figure 29:
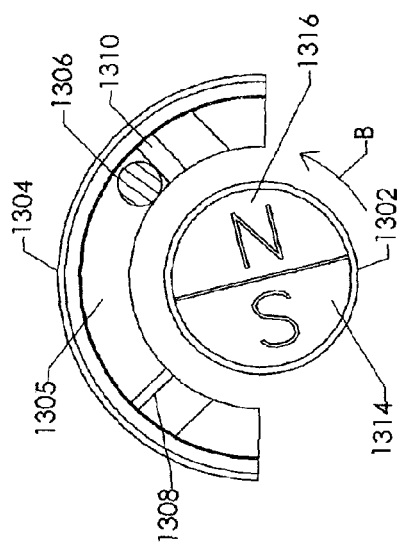
Figure 28:
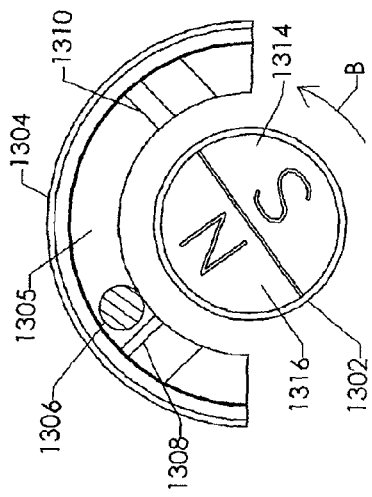
Figure 30:
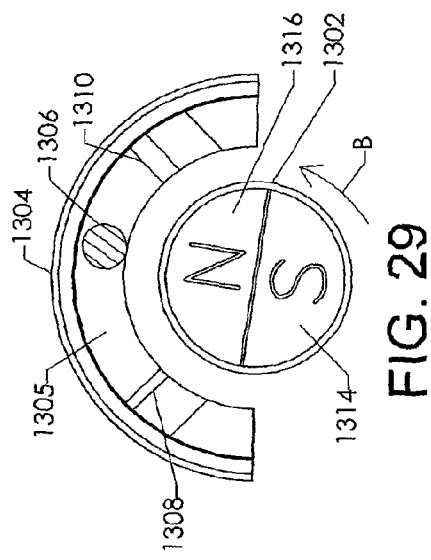

FIGS. 23-30 illustrate the acoustic mechanism being activated by counter-clockwise rotation of the driven magnet 1302. In this process, the first impact surface 1308 serves to stop the magnetic ball 1306, and the magnetic ball 1306 accelerates and impacts the second impact surface 1310, creating a different acoustic signal. For example, the different acoustic signal may include a louder signal or a signal with a different frequency (e.g., pitch). In FIG. 23, the driven magnet 1302 begins to rotate in the counter-clockwise direction (arrow B). As illustrated, the starting point of the magnetic ball 1306 is adjacent tire south pole 1314 of the magnet 1302. As seen in FIG. 24, as the magnet 1302 rotates, the magnetic ball 1306 follows the south pole 1314. This continues until, as shown in FIG. 25, the magnetic ball 1306 is stopped by the first impact surface 1308. As seen in FIG. 25, the magnetic ball 1306 is trapped against the first impact surface 1308, while the driven magnet 1302 continues to rotate. The magnetic ball 1306 may roll at this point but if is forced against the first impact surface 1308 by its attraction to the south pole 1314 of the magnet 1302, until the north pole 1316 becomes closer to the magnetic ball 1306 as shown in FIG. 26, at which point the magnetic ball 1306 accelerates towards the second impact plate 1310 in the direction of arrow β, thereby hitting it (as seen in FIG. 27) and creating an acoustic signal or sound having a greater intensity than when the magnetic ball 1306 was stopped by the first impact surface 1308. Now as seen in FIG. 28, as the magnet 1302 continues to turn, the magnetic ball 1306 follows the north, pole 1316 of the magnet 1302, and continues to follow the north pole 1316 (FIG. 29) until the magnetic ball 1306 is stopped by the first impact surface 1308 as illustrated in FIG. 30.

It can be appreciated that each turn of the magnet 1302 creates two (2) relatively loud strikes, which can be detected by a non-invasive, external device comprising a sonic sensor, for example, a microphone (e.g., sensor 1084 in FIG. 14). If, for example, the magnet 1302 is turning a 0-80 lead screw (e.g., lead screw 226) to adjust the distraction device 140), then each turn represents 1/80 of an inch in the distraction displacement, and thus each half turn represents 1/160 of an inch, or 0.00625". If there is gear reduction at the output of the magnet 1302, for example 4:1, then a full turn represents 1/320 of an inch and each half turn represents 1/640 of an inch. Therefore, acoustic sensing of this nature allows for very precise control of adjustment of the distraction device 140. If the speed is too high, the sensor can alternatively be programmed to sense only specific turns. Alternatively, a secondary magnet may be disposed on the post gear reduction portion of the torque transmission system, so that the number of turns to sense are fewer in number and less frequent.

It can also be appreciated that the acoustic signal or sound made by the strike due to the acceleration of the magnetic ball 1306 against the first impact surface 1308 during clockwise rotation of the magnet 1302 will contain a different frequency spectrum than the acoustic signal or sound made by the strike due to the acceleration of the magnetic ball 1306 against the second impact surface 1310 during counterclockwise rotation of the magnet 1302. As one example, the acoustic sensor 1084 illustrated in FIG. 14 may provide a relatively simple, low-cost device in which the direction of the rotation (i.e., increasing distraction vs. decreasing distraction) can be automatically identified. Further, the acoustic sensor 1084 is able to determine the exact number of half rotations in each direction.

The acoustic sensor 1084 may be operatively integrated with a programmable logic controller (PLC) such as the PLC 1080 described herein. In this regard, the exact distraction length of the distraction device 140 can be determined. The PLC 1080 is able to identify the direction of rotation via the frequency of sound, and then change the direction of rotation if this is not the desired direction. The PLC 1080 is also able to count the number of half rotations until amount of restriction Is achieved. If there is any slip between the magnets 1134, 1136 of the external device 1130 and the driven magnet 1302, the PLC 1080 will not detect the acoustic signal and thus will not count these as rotations.

There may be cases in which the medical personnel performing the non-invasive adjustment is not aware which direction of rotation of the external device magnets 1134, 1136 will cause increased distraction and which will cause decreased distraction, the PLC 1080, however, will be able to immediately identify the correct direction of rotation by the detected frequency.

Figure 31:
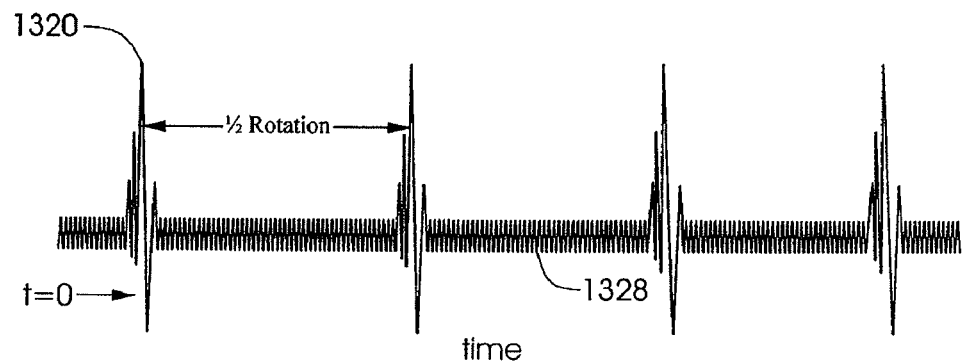
FIG. 31 illustrates the acoustic signal as a function of time of an embodiment of the invention having an acoustic or sonic housing that contains a magnetic ball. Peaks are seen every ½ rotation of the driven magnet in the counter-clockwise direction.
Figure 32:
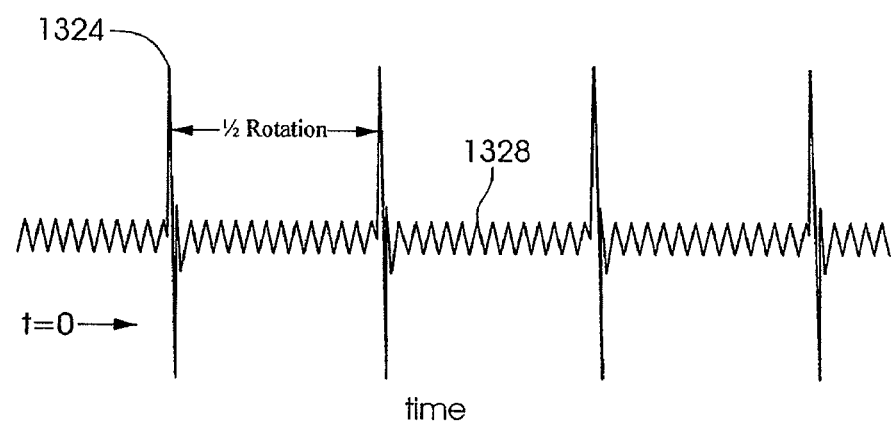
FIG. 32 illustrates the acoustic signal as a function of time of an embodiment of the invention having an acoustic or sonic housing that contains a magnetic ball. Peaks are seen every ½ rotation of the driven magnet in the clockwise direction.
Figure 33:
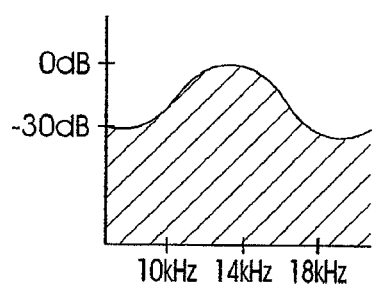
FIG. 33 illustrates the frequency response of the acoustic or sonic housing of the type illustrated in FIGS. 15-30 during counter-clockwise rotation of the driven magnet.
Figure 34:
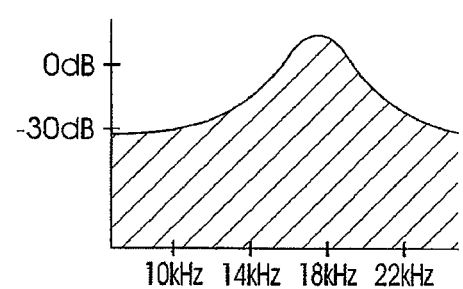
FIG. 34 illustrates the frequency response of the acoustic or sonic housing of the type illustrated in FIGS. 15-30 during clockwise rotation of the driven magnet.

For example, FIG. 31 illustrates the sound 1320 detected from counter-clockwise rotation of the magnet 1302 and FIG. 32 illustrates the sound 1324 detected from clockwise rotation of the magnet 1302. There may be additional background acoustic signals or noise 1328 created by, for example, the sound of the motor 1132 of the external device 1130. In both rotation directions, the acoustic "clicks" 1320 and 1324 look very similar to each other. However, by analyzing the frequency spectrum of the clicks, one is able to discern differences between clockwise and counter-clockwise rotation of the magnet 1302. As seen in FIG. 33, the frequency spectrum for the counter-clockwise rotation is centered at about 14 kHz, while the spectrum for clockwise rotation (FIG. 34) is centered at about 18 kHz. This shift or change in center frequency can be used as a basis for determining the absolute rotational direction of the magnet 1302.

Figure 35:
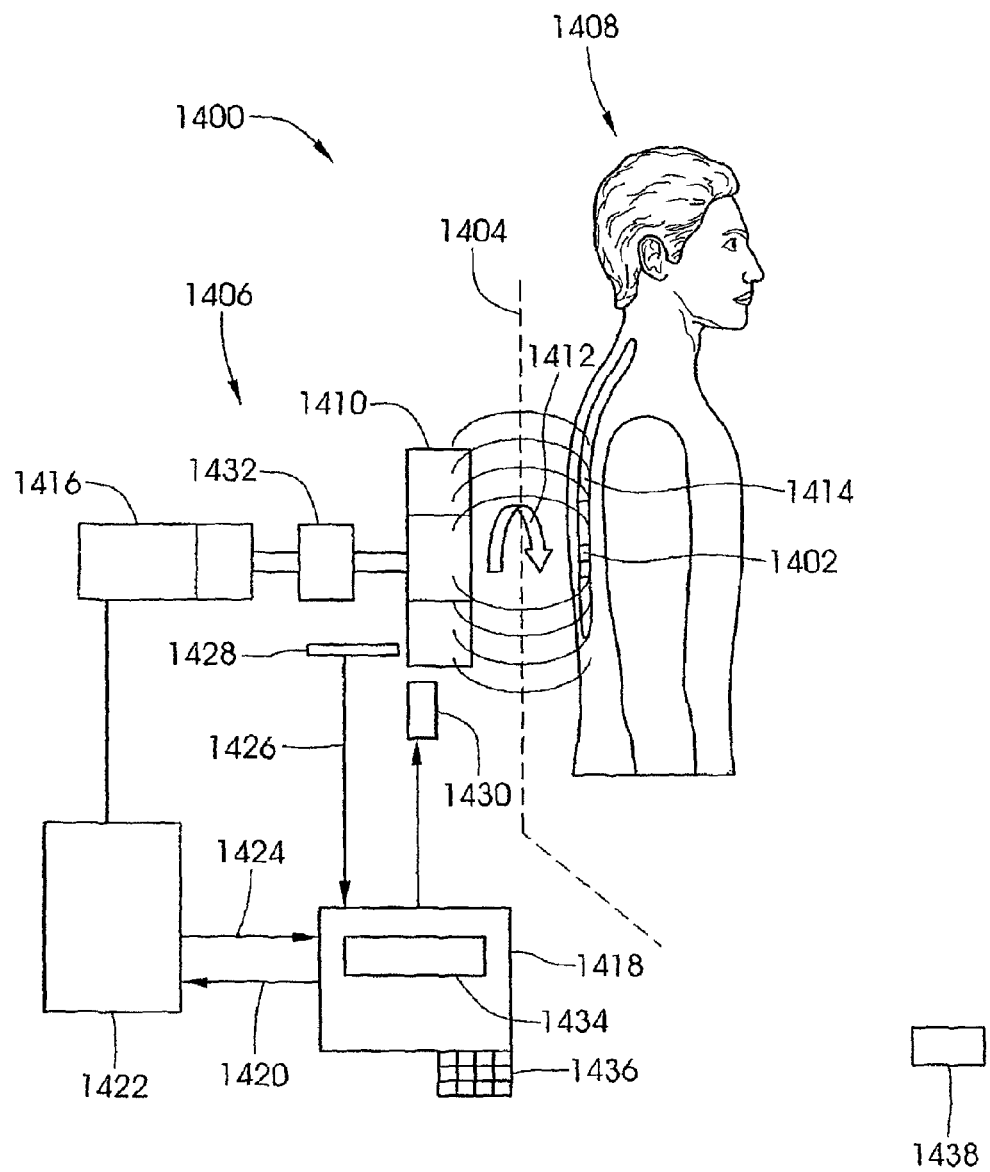
FIG. 35 illustrates a system for driving an internally located driven magnet via an external device using a feedback mechanism.

FIG. 35 illustrates a system 1400 for driving an internally located driven magnet 1402 of a distraction device 140 via an external device 1406 using a feedback device. One or more implanted driven magnets 1402 are coupled magnetically through the skin 1404 of a patient 1408 to one or more external drive magnets 1410. A rotation or movement of the external drive magnets 1410 causes an equal rotation of the driven magnet(s) 1402. Turning the driven magnet(s) 1402 in one direction 1412 causes the distraction device 1414 to increase distraction while turning the driven magnet(s) 1402 in the opposite direction causes the distraction device 1414 to decrease distraction. Changes to the distraction device 1414 distraction distance or distraction force depend upon the number of turns by the one or more drive magnets 1410.

The drive magnets 1410 are rotated by the external device 1406, which has an electric gear motor 1416 which is controlled by a programmable logic controller (PLC) 1418. The PLC 1418 outputs an analog signal 1420 to a motor drive circuit 1422 which is proportional to the motor speed desired. The PLC 1418 receives an analog signal 1424 from the motor drive circuit 1422 that is proportional to the current draw of the motor. The gear motor's 1416 current consumption is proportional to its output torque. An electronic torque sensor may be used for this purpose. The measured current draw may be used to monitor the change in output torque.

The PLC 1418 receives a pulsed input, signal 1426 from art encoder 1428 that indicates the angular position of the drive magnets 1410. The PLC 1418 controls a spring loaded braking system 1430 that automatically stops the drive magnet 1410 if there is a loss of electrical power or other emergency.

A slip clutch 1432 is included between the gear motor 1416 and the drive magnet 1410 to prevent the gear motor 1416 from over torqueing the driven magnet 1402 and potentially damaging the distraction device 140, for example, if the distraction device 140 does not have its own slip clutch. The PLC 1418 has a built in screen 1434 to display messages and a keypad 1436 for entering data. External push button switches and indicator lights may be incorporated for user comfort and ease of use.

The motor current (output torque) is monitored continuously whenever the device is turning. If the motor current exceeds the maximum allowable current (based on safety requirements of the device components and/or patient tissue) the gear motor 1416 is stopped and the brake 1430 is applied. This can be done both in software and hardware. The mechanical slip clutch 1432 also prevents over torqueing of the device. An exemplary threshold torque is 5.0 ounce-inches.

In one embodiment, each patient will have a number that corresponds to the distraction displacement of their particular distraction device 1414. A distracted device 1414 will have a number such as 5.0 cm for its distraction displacement and a fully non-distracted device will have a number such as 0.0 cm.

This number can be stored on an electronic memory card 1438 that the patient 1408 carries. The PLC 1418 can read the current number from the memory card 1438 and update the number after adjustment. The patient's number can be recorded manually in the patient's chart and kept at the physician's office or printed on an information card that the patient carries. Alternatively, the information can be stored on and read from an RFID chip implanted in the patient.

The patient's number is first entered into the PLC 1418 so it knows the patient's starting point. If the patient's records are completely lost, the system can always have a new setting manually input based on an X-ray image determination of the distraction displacement of the restriction device 1414.

A physician may adjust the distraction device 1414 several ways. An absolute move to a new distraction displacement (or force) may be entered directly. For example, a patient 1408 currently at 2.00 cm distraction displacement may need to be adjusted to 2.50 cm. The physician simply enters the new distraction displacement and presses a 'GO' button. The physician may prefer a relative (incremental) move from the current distraction displacement. Each press of a button will cause the device to increase or possible decrease a fixed amount, say 0.20 cm of distraction displacement, or 0.02 cm. In another aspect, there may be provided increase and decrease buttons which increase/decrease the distraction of the distraction device 1414 as long as the button is held. It should be noted that the displacement of distraction is a relative term, and that the force gauge disclosed in this invention may be the preferred manner to adjust distraction, instead of a dimensional manner. Further, the PLC 1418 may automatically adjust the external device 1406 to reach the desired final distraction force or length based at least in part on a response generated by a feedback device. The particular feedback device may be any number of devices described herein including strain or force gauge feedback, acoustic feedback, optical feedback, motor current and the like.

Once the external device 1406 is commanded to move, the PLC 1418 slowly ramps up the speed of the gear motor 1416 while monitoring the motor current (torque). A known minimum drive torque must be present for verification that the magnetic coupling to the restriction device is locked and not slipping. This can be monitored with, for example, the acoustic feedback system. The minimum, torque value can be a curve that is stored in the PLC 1418 that is based on the amount of distraction, the direction of movement (increasing/decreasing), even the model number or serial number of the distraction device 1414.

Also, if a sudden torque reversal is detected by the PLC 1418, a slip has occurred. As the like magnet poles (North-North & South-South) which are repelling slip past each other, they are attracted to the adjacent opposite poles (North-South & South-North). This causes a momentary reversal of drive torque. This torque reversal can be detected by the PLC 1418. If a slip occurs, the PLC 1418 can subtract the appropriate amount from the move. If too many consecutive slips occur, the PLC 1418 can stop and display a message.

As the drive magnet 1410 rotates, revolutions and fractions of revolutions are counted by the PLC 1418 and converted to changes in the distraction. Once the move is complete, the PLC 1418 stops the gear motor 1416 and applies the brake 1430. It should be understood that the feedback devices mentioned above is applicable to the external device, and to many other types of magnetic drives with the exception of nearby or proximally-located electromagnetic coils which do not have a motor.

Any of the compatible configurations of a distraction device/adjustment mechanism/external adjustment device are contemplated to be combinable as alternative embodiments to those specifically described herein. In addition, the mechanical mechanism of the distraction device can be achieved by any of the designs and methods by using a rotating drive shaft, or by a tension/compression member. In other words, rotation can be done only to proximal assemblies or assemblies within the distraction device, which then, through gearing, cause longitudinal shortening or lengthening of a wire or cable, which pulls tension on a belt or rod to cause the distraction device to increase or decrease distraction (distance or force).

Figure 36:
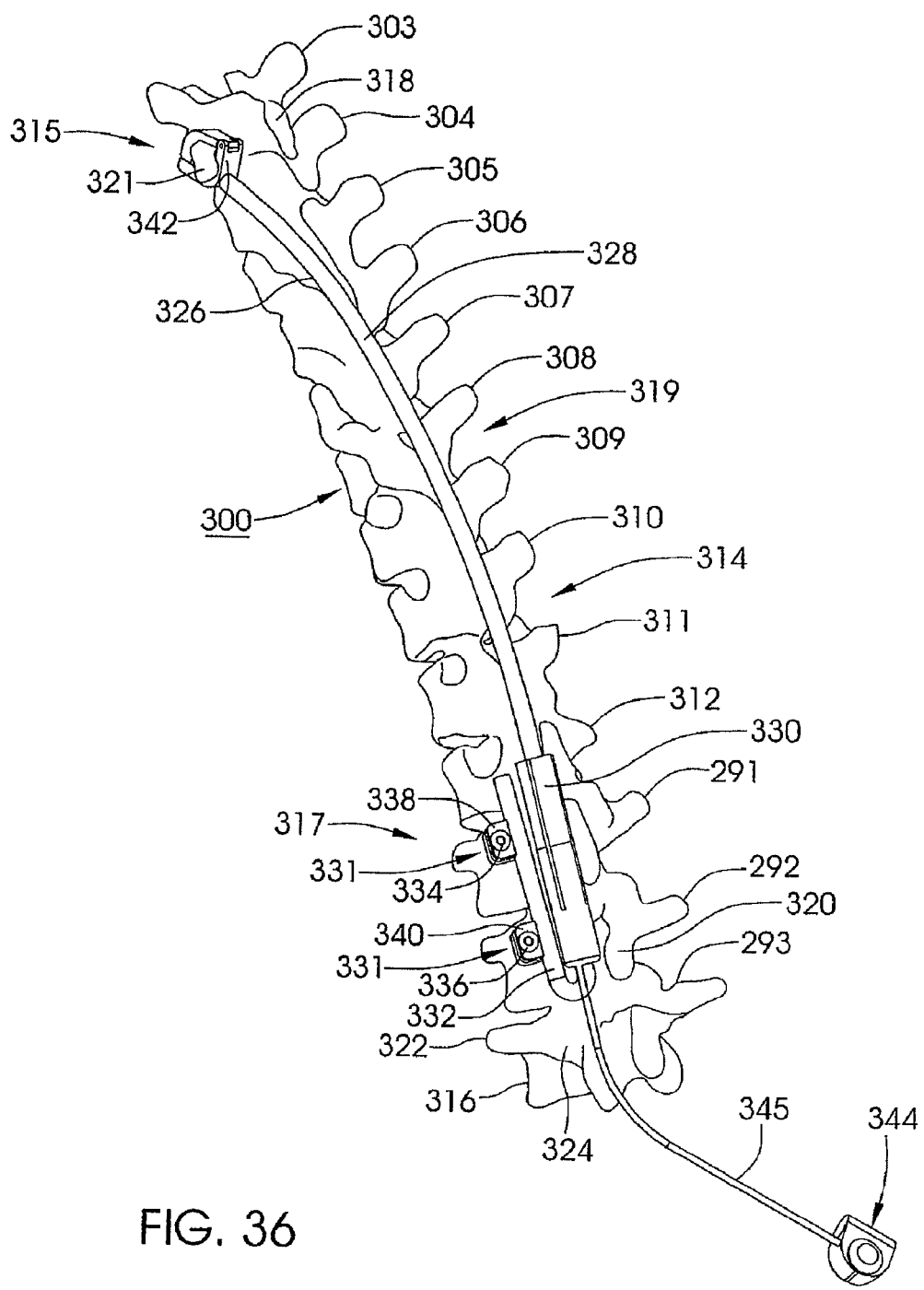
FIG. 36 illustrates a distraction device affixed to a spine of a patient according to one embodiment.

FIG. 36 illustrates an embodiment of a distraction device 314 implanted within a patient and fixated at its upper end 315 and lower end 317 to the patient's spine 300. The illustrated example of the spine 300 includes the particular thoracic and lumbar vertebrae that typically encompass a scoliotic curve, for example the curve of a patient with adolescent idiopathic scoliosis. The T3 through T12 thoracic vertebrae, 303, 304, 305, 306, 307, 308, 309, 310, 311, 312, respectively and the L1 through L3 vertebrae, 291, 292, 293 are depicted in FIG. 36, not in a severe scoliotic condition, but in a very slight residual curve that represents a modest curve that has been partially or completely straightened during the implantation procedure. Each vertebra is different from the other vertebra by its size and shape, with the upper vertebra generally being smaller than, the lower vertebra. However, generally, the vertebrae have a similar structure and include a vertebral body 316, a spinous process 318, 320, laminae 326, transverse processes 321, 322 and pedicles 324. In this embodiment, the distraction device 314 includes a distraction rod 328 which is adjustable (lengthwise) via a coupled adjustable portion 330. The distraction device 314 is fixated to the spine 300 via a clamp 342 at the upper end of the distraction rod 328. In FIG. 36, the clamp 342 is secured around the transverse process 321 of the T4 vertebra 304. Alternatively, the clamp 342 may be secured around an adjacent rib (not shown) or rib facet. In still another alternative, the clamp may be replaced by a laminar and pedicle hook system, or pedicle screw system. FIG. 37 illustrates one such alternative embodiment in which a distraction device 314 includes one or more laminar hooks 346 that are used to secure an upper end 315 of the distraction device 314 to the spine (not shown). The lower end 317 of the distraction device is secured to the spine using one or more pedicle hooks 348.

Referring back to FIG. 36, the distraction device 314 is illustrated as being fixated to the spine 300 with a pedicle screw system 331 comprising a connecting rod 332 and two toe clamps 338, 340. This particular embodiment composes a magnetic adjustment device 344 which is spaced from the adjustable portion 330 via a transmission cable 345.

Turning to FIG. 38, more detail of the pedicle screw system 331 is shown. The pedicle screw 349 passes through a hole in base 350, securing base to the L1 vertebra 291 (FIG. 36) though its pedicle (left pedicle in this case). Locking screw 334 can be loosened to adjust the angle α of the connecting rod 332, and then locking screw 334 can be tightened so that toe clamp 338 securely holds connecting rod 332 in place without further rotation. The second toe clamp 340 is adjusted in the same way by tightening locking screw 336. Because a scoliotic spine is also rotated (usually the center section is rotated to the right in AIS patients), the non-fusion embodiment presented here allows de-rotation of the spine 300 to happen naturally, because there is no fixation at the middle portion 319 of the distraction device 314.

Figure 39:
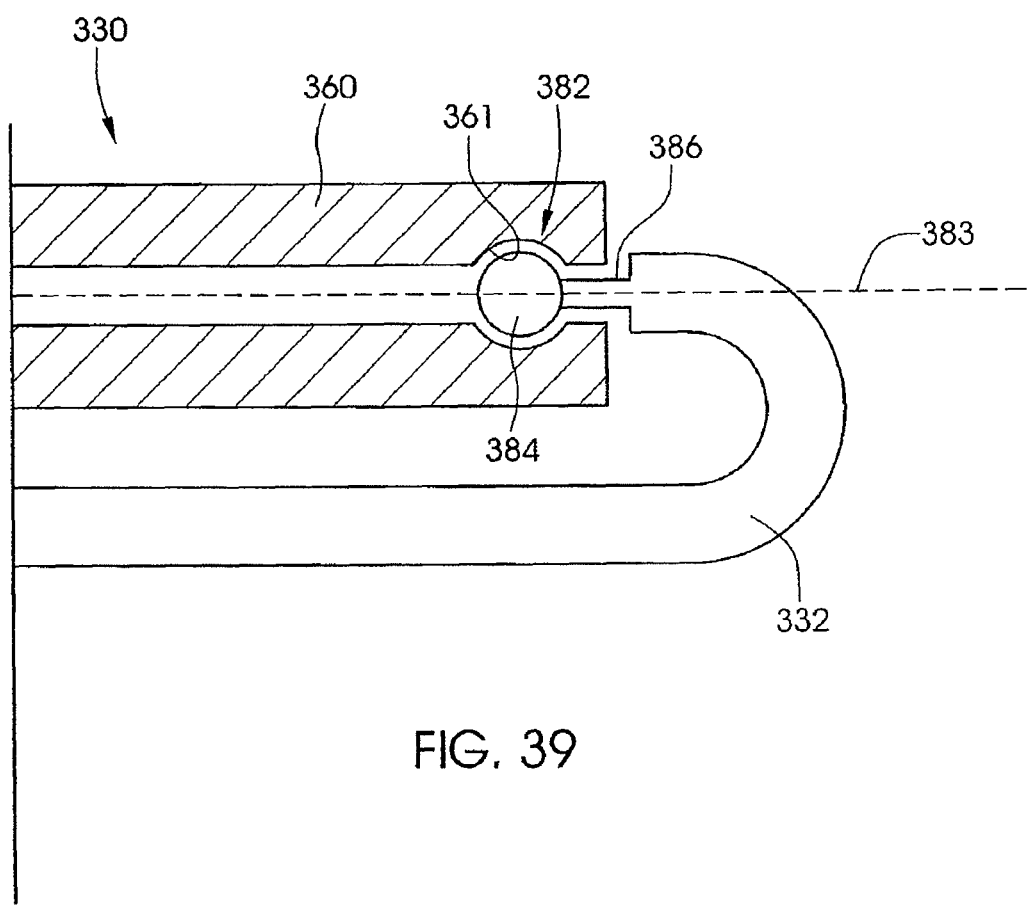
FIG. 39 illustrates the connection between an adjustable portion of the distraction device and a connecting rod that allows for, among other movements, free rotation.

In order to further facilitate this de-rotation, the distraction device 314 allows for free rotation at its ends. For example, turning to FIG. 39, the adjustable portion 330 is attached to the connecting rod 332 via a ball joint 382. The end of the connecting rod 332 has a substantially 180° degree curve which allows it to meet the adjustable portion 330 along the same axis 383. The extreme end of the connecting rod 332 comprises a stem 386 and a ball 384. A mount 360 is disposed at the end of the adjustable portion 330 and has a partial spherical internal contour 361 to mate with the ball 384, and allow for free rotation. It may also allow for polyaxial motion. It should be noted that distraction rod 328 may be precurved with the typical shape of a normal sagittal spine, but it should also be noted that the curve may be slightly different than standard scoliosis fusion instrumentation, because in the non-fusion embodiment described herein, the distraction device 314 is not flush with the spine but rather is placed either subcutaneous or subfascial, and thus is not below the back muscles. The only portions of the distraction device 314 that are designed to be placed below the muscles are the clamp 342 and the portion of the distraction rod 328 immediately adjacent the clamp 342, the pedicle screw system 331 and the connecting rod 332. Thus, FIG. 36 illustrates an embodiment in which the bulk of the hardware associated with the distraction device 314 is placed over the muscle. It should be understood, however, that in alternative configurations, any other part of the entire implantable embodiment may be placed under the muscle (i.e., sub-muscular). It should be appreciated that a much smaller amount of muscle needs to be dissected during the procedure in comparison with current fusion procedures. This will allow for a much shorter procedure, much less blood loss, much quicker recovery, and less time in the hospital/less risk of infection. Further, it may be desirable to produce the "J" curve of the connecting rod 332 or the "S" curve of connecting rod 323 of FIG. 37 with flanges or ribs at their highest stress points in order to increase their durability in demanding implant conditions.

Figures 40, 41:
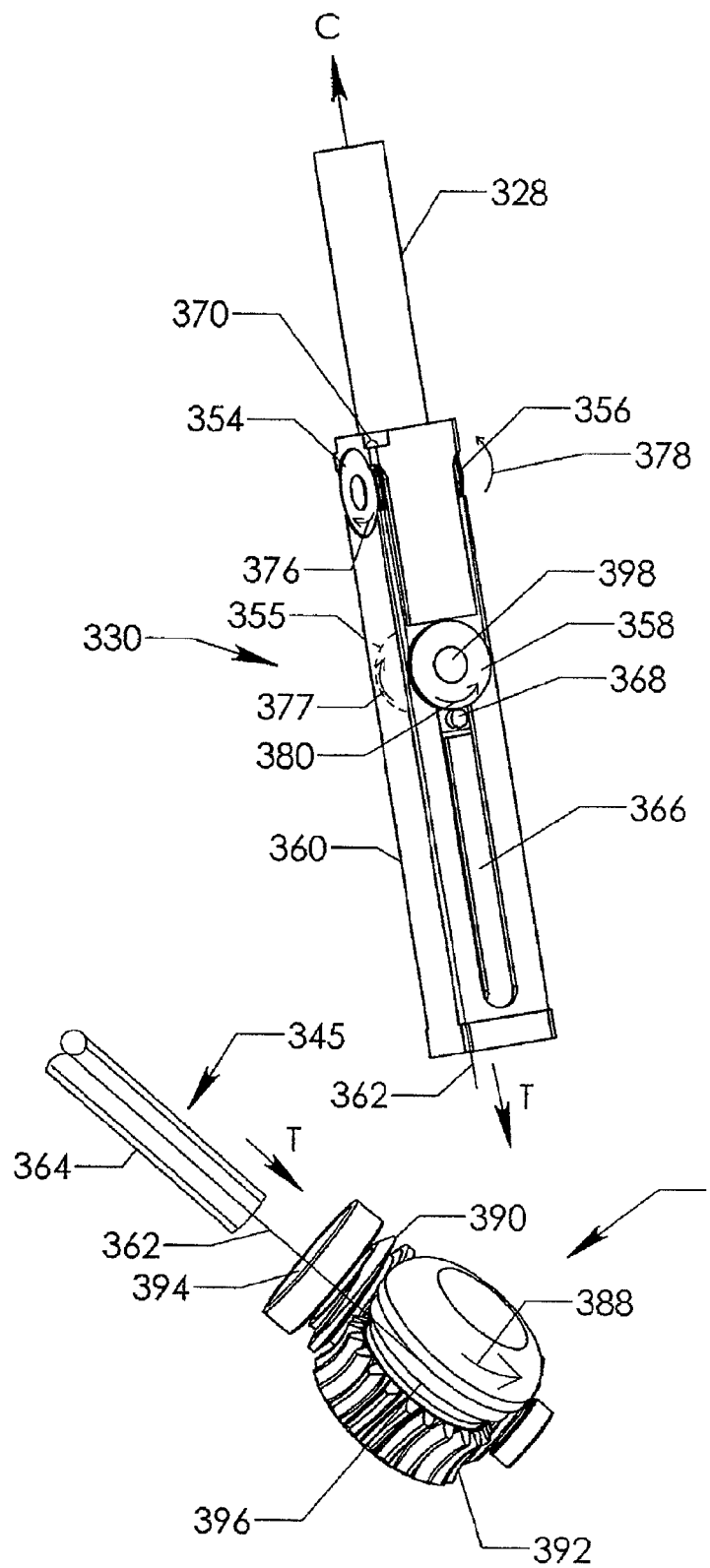
FIG. 40 is a perspective view of an adjustable portion of a distraction device according to another embodiment.
FIG. 41 is a perspective view of a remotely located magnetic adjustment device that, is used in connection with the adjustable portion illustrated in FIG. 40.
Figure 42:
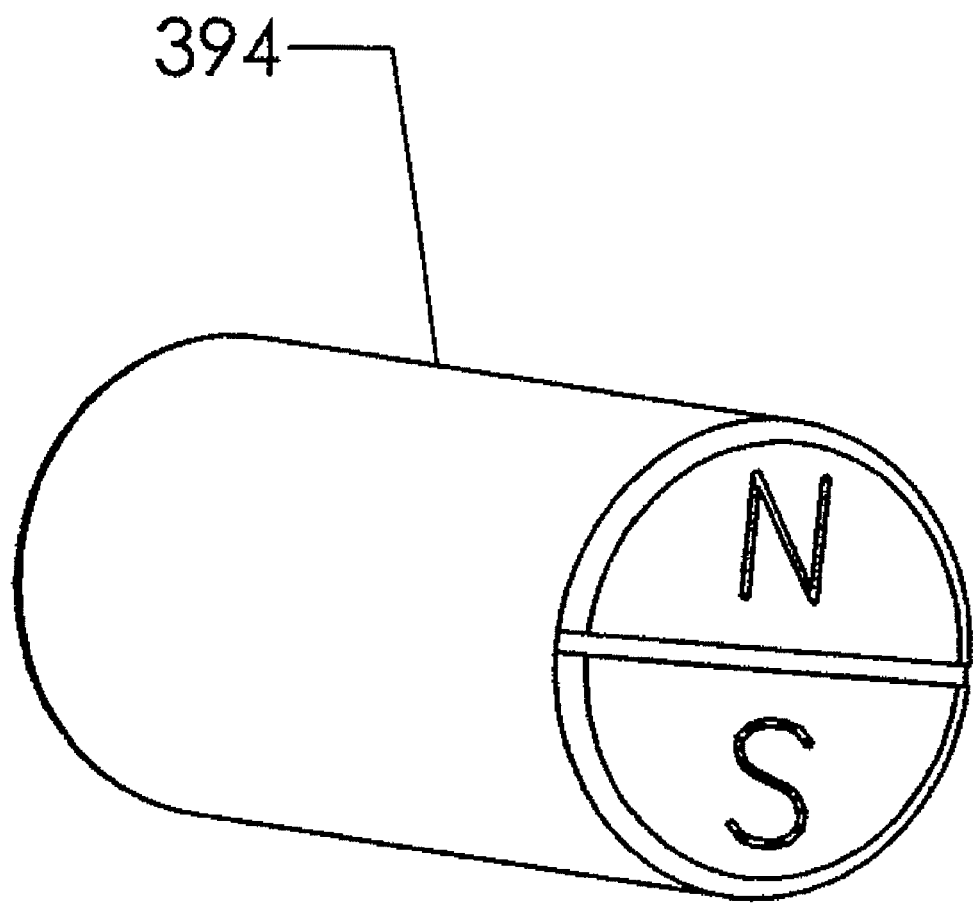
FIG. 42 illustrates a perspective view of a cylindrical magnet that is magnetized in the radial direction according to one embodiment.

FIGS. 40 and 41 illustrate one embodiment of a remotely-located magnetic adjustment device 344 that enables adjustment of the distraction device 314 from a location that is remote from the adjustable portion 330. As explained below, the adjustable portion 330 is operatively coupled to the magnetic adjustment device 344 via a transmission cable 345. For example, the magnetic adjustment device 344 may be placed subcutaneously in the buttocks area or even the abdominal area. Alternatively, the magnetic adjustment device 344 may be located integral to the adjustable portion 330. In its remote configuration, however, the magnetic adjustment device 344 (depicted in FIG. 41 without its protective outer cover) includes a worm 390 and a cylindrical magnet 394 fixedly secured inside the worm 390. The cylindrical magnet 394 is preferably magnetized radially as illustrated in FIG. 42. Activation of an external adjustment device (e.g., external adjustment device 1130) causes the cylindrical magnet 394 and worm 390 to turn. The worm 390 contains threads about its exterior surface and engages with a rotatable gear 392 which, in turn, is operatively coupled to a spool 396. The spool 396 includes a groove or the like about its periphery in which a cable 362 is disposed. During operation of the device, rotational movement of the cylindrical magnet 394 causes rotation of the gear 392 that, in turn, causes rotation of the spool 396. As the gear 392 turns, the spool 396 winds or unwinds a cable 362 that extends through a protective sheath 364 located in the elongated transmission cable 345 that couples the adjustment device 344 to the adjustable portion 330. Depending on the direction of rotation of the gear 392, the cable 362 is either tightened or loosened.

Referring to FIG. 41, as the gear 392 turns in direction 388, tension (T) is increased. The opposite end of cable 362 is secured to frame 360 by stop 370. In one embodiment the cable 362 is pulled over first pulley 354, which turns in a first rotational direction 376. Cable 362 then wraps around second pulley 355 (shown in phantom) In the back of frame 360 causing second pulley 355 to turn in second rotational direction 377. The cable 362 then wraps around a third pulley 356 causing it to turn in third rotational direction 378. After the third pulley 356, the cable 362 wraps around a fourth pulley 358, causing it to turn in a fourth rotational direction 380. Second pulley 355 and fourth pulley 358 are rotationally attached to the distraction rod 328 via axle 398, and are slidably contained within frame 360 by pin 368 which slides in a groove 366.

The combination of the pulleys 354, 355, 356, 358 act as a block and tackle arrangement that amplifies the force applied to the distraction rod 328 in response to an applied tension (T). For instance, a tension (T) that is placed on cable 362 imparts a compressive force (C) on the distraction rod 328 that is four times as large (i.e., C=4*1). Of course, it should be understood that by driving the cylindrical magnet 394 and worm 390 in the opposite direction, the gear 392 causes the spool 396 to unwind, and thus both T and C are decreased.

Figure 43:
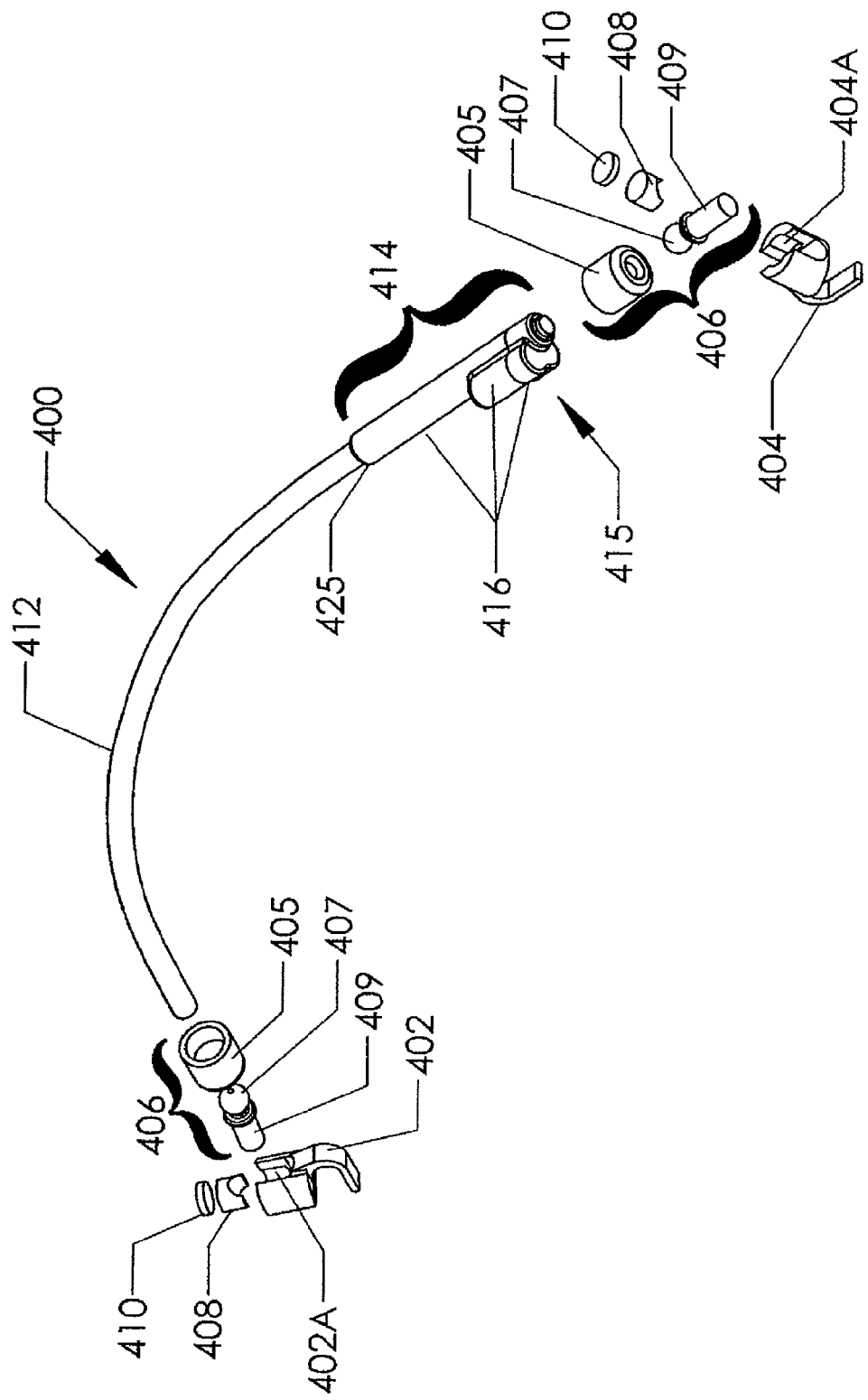
FIG. 43 illustrates a perspective view of a distraction device according to another embodiment.

FIG. 43 illustrates another embodiment of a distraction device 400. In this embodiment, hook fixation systems are used to secure to distraction device 400 to the patient's spine. The hook fixation, system is depicted in an exploded configuration in FIG. 43 and includes hooks 402, 404 (for example lamina hooks, facet hooks or rib hooks) located on opposing ends of the distraction device. The hooks 402, 404 are operatively coupled to hall joints 406. Each ball joint 406 includes a coupler 405 that interfaces with a ball 40 or other substantially spherical member disposed at the end of a post 409. The hooks 402, 404 each include a recess 402A, 404A that are dimensioned to receive the post 400 of each ball joint 406. The post 409 is frictionally engaged or locked with respect to its respective hook 402, 404 using a clamping member 408 and overlying cap 410. The coupler 405 includes a receiving portion such as an internal threaded portion (not shown) that interfaces with opposing ends of the distraction rod 412. Of course, the coupler 405 may be secured to distraction rod 412 in other ways such as, for instance, mounting screws, a bond, weld, or even through the use of a cement or other adhesive material. In this regard, once mounted, both hooks 402, 404 are able to articulate about the swivel-action ball joint 406 to accommodate the changing geometry as the spine is subject to distraction forces.

As seen in FIG. 43, the distraction rod 412 is supplied in a precurved configuration, and can be cut to the desired length and bent into a custom configuration to fit the patient's specific anatomy. Typically, the portion that is to be cut would be the end of the distraction rod 412 that is located away from the adjustable portion 414. Adjustable portion 414 in this embodiment comprises an offset gearing assembly 415 having a cover 416.

Figure 44:
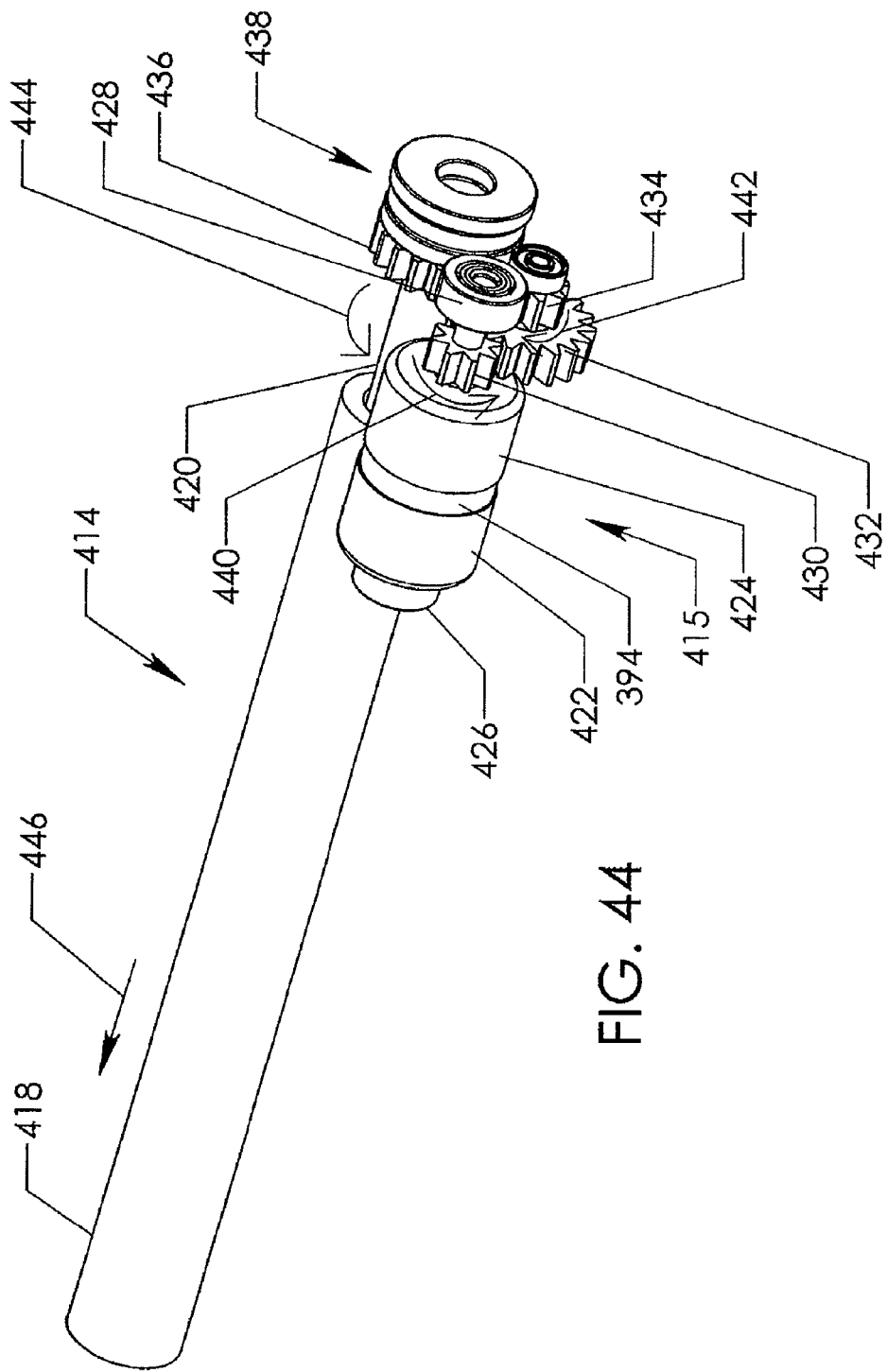
FIG. 44 illustrates the adjustable portion of FIG. 43 without the cover.

FIG. 44 illustrates the offset gearing assembly 415 with the cover 416 removed from the adjustable portion 414 in order to better show the internal components responsible for effecting the distraction forces on the distraction rod 412. As seen in FIG. 44, a cylindrical magnet 394 is rotationally held by cups 422, 424 and the assembly 415 is free to rotate between ball bearings 426, 428 disposed on opposing ends thereof. The cylindrical magnet 394 may include a permanent magnet made out of the materials described herein with respect to the other embodiments. The assembly 415 includes a first gear 430 which rotates as the assembly 415 is rotated about its axis of rotation. An external adjustment device (e.g., 1130) causes cylindrical magnet 394 to turn in a first rotational direction 440 which also causes the first gear 430 to turn in same, first direction 440. The first gear 430 meshes with a second gear 432 causing the same to turn in a second rotational direction 442. A third gear 434 is secured to the second gear 432 and rotates along with, second gear 432. The third gear 434 meshes with a fourth gear 436, causing it to turn in a third rotational direction 444. The fourth gear 436 is secured to a lead screw 420 which extends longitudinally inside a sleeve 418 or jacket. A thrust bearing 438 is provided in a face-to-face arrangement with the fourth gear 436 to reduce frictional forces during rotation of the lead screw 420. The inner surface of the sleeve 418 contains a threaded inner bore (not shown) which extends at least a portion of the length of the sleeve 418. Lead screw 420 is allowed to turn because of a thrust bearing 438 located at end of the lead screw 420.

When the lead screw 420 turns in the fourth rotational direction 444 and engages threaded inner bore of sleeve 418, the sleeve 418 begins to move in the distraction direction 446. The sleeve 418 is coupled at one end to the distraction rod 412, and thus, when sleeve 418 and distraction rod 412 are distracted by the offset gearing assembly 415, the distraction device 400, which is coupled to the spine, imparts an increased distraction force. If the cylindrical magnet 394 is turned in the opposite direction, tire distraction force is lessened. Because of both the gearing and the lead screw thread, a relatively low torque can be delivered to rotate the cylindrical magnet 394 which, in turn, can impart a very high distraction force on the sleeve 418, and thus the distraction rod 412. In one embodiment, the first gear 430 has eight (8) teeth, second gear 432 has eighteen (18) teeth, third gear 434 has ten (10) teeth, and fourth gear 436 has eighteen (18) teeth. The meshing of the first gear 430 and second gear 432 has a gear ratio of 18:8 and the meshing of the third gear 434 and fourth gear 436 has a gear ratio of 18:10. This creates an overall gear ratio for the offset gearing assembly 415 of 81:10, and thus an output torque to input torque ratio of 4.05. Assuming a typical gear efficiency of 0.90 (due to fractional effects in the each of the two gear meshes), a 6.0 ounce-inch torque applied to the cylindrical magnet 394 can produce an approximate torque of 19.7 ounce-inches on the lead screw. A lead screw 420 having a diameter of approximately 3.5 mm (0.138") and approximately 100 threads per inch has been measured to have an efficiency of approximately 0.084. Thus, a 6.0 ounce-inch torque applied to the cylindrical magnet 394 will produce a distraction force of as high as 65 pounds. This assumes an external adjustment, device 1130 having two external magnets 1134, 1136 each having a diameter of approximately two (2) inches.

Returning to FIG. 43, an annular dynamic seal 425 provided at one end of the adjustable portion 414 allows the distraction rod 412 to pass through the end of the adjustable portion 414 without any body fluids or materials being able to enter the adjustable portion 414. The interior of the adjustable portion 414 is thus substantially isolated, or sealed off from the surrounding implant environment. While FIG. 43 illustrates a pair of hooks 402, 404 that are used to secure the distraction device 400 to the spine of the patient. It should be understood that, other anchors may be used to affix the ends of the distraction device 400 to the spine. For example, screws or other fasteners may be used to secure one or both ends of the distraction device 400 to the patient's spine. Typically, screws are used for the lower portion of the distraction device 400 while hooks or screws are generally preferred for the upper portion of the distraction device 400. Clamps may also be used to secure one or both ends of the distraction device 400 to the patient's spine. Generally, clamping structures are used to secure the upper portion of the distraction device 400 to a rib or transverse process of the subject.

Figure 45:
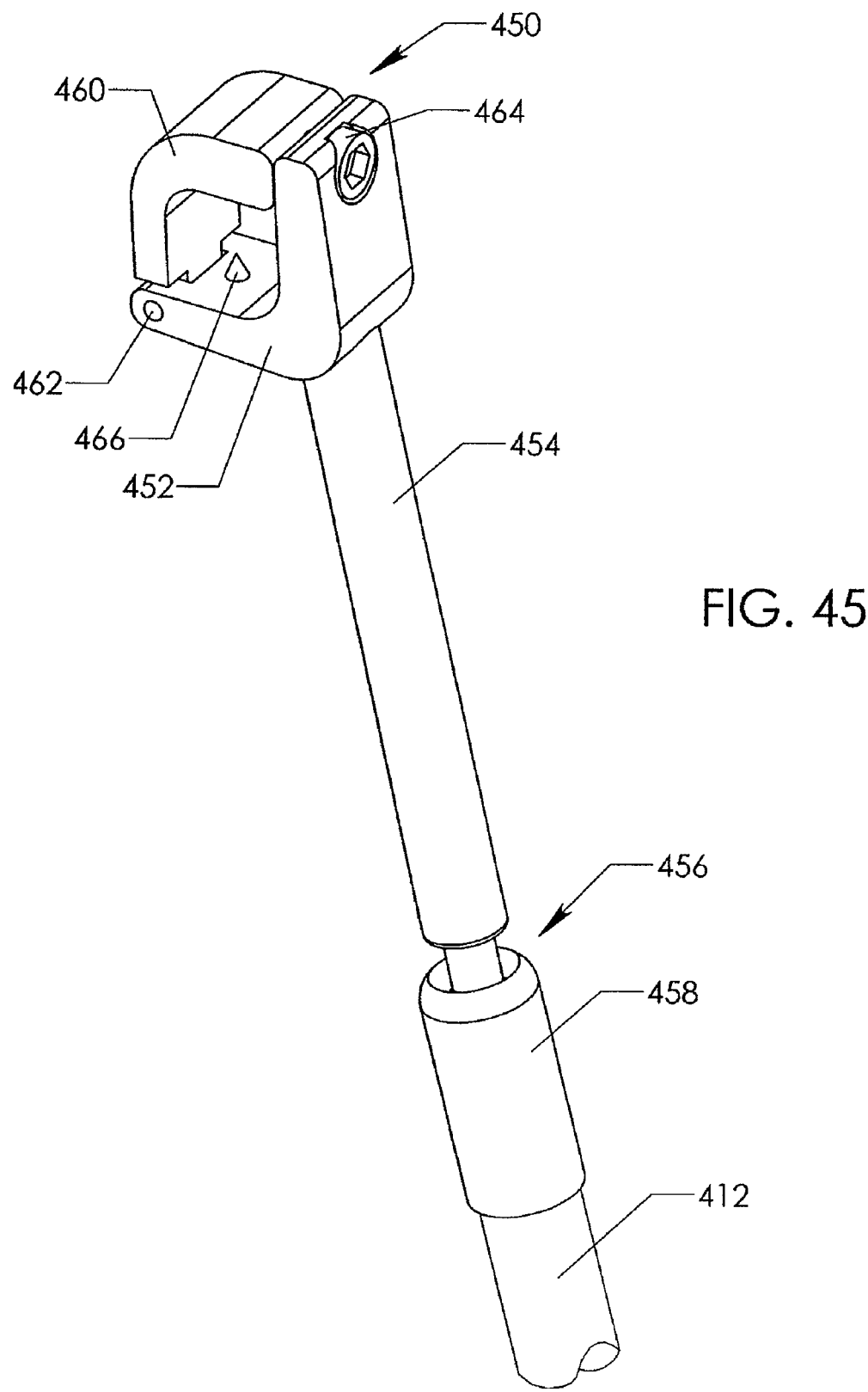
FIG. 45 illustrates a clamp used to affix the distraction device to a patient's anatomical structure according to one embodiment.

For example, FIG. 45 illustrates a clamp 450 that can be used to secure one end of the distraction device 400 to a rib or transverse process. The clamp 450 includes an "L-shaped" bracket 452 that is mounted on a shall 454. The shaft 454 terminates at a swivel joint 456 that provides swiveling movement between a coupler 458 and the clamp shaft 454. The coupler 458 is configured to receive one end of the distraction rod 412 (e.g., using threads, mounting screw(s), adhesive, cement, laser weld, or the like). The clamp 450 includes a pivoting bracket 460 that pivots about a pin 462 from, an open configuration to a closed configuration. The clamp 450 that is illustrated in FIG. 45 pivots from the front of the patient to the back of the patient and is referred to as a "front-to-back" clamp. In alternative configurations, the clamp 450 may be constructed as a "back-to-front" clamp in which the pivoting bracket 460 pivots from the back of the patient to the front. The pivoting bracket 460 can be locked in the closed configuration by the fastener 464 which engages and holds the pivoting bracket 460 to the L-shaped bracket 452. The fastener 464 may be a screw, bolt or the like that can be tightened or loosened by rotation using a tool (e.g., wrench or driver). In one embodiment, the clamp 450 further includes an optional detent 466 or other protuberance on the L-shaped bracket 452 that aids in fixedly securing the clamp 450 to the rib or other anatomical structure.

Figure 46:
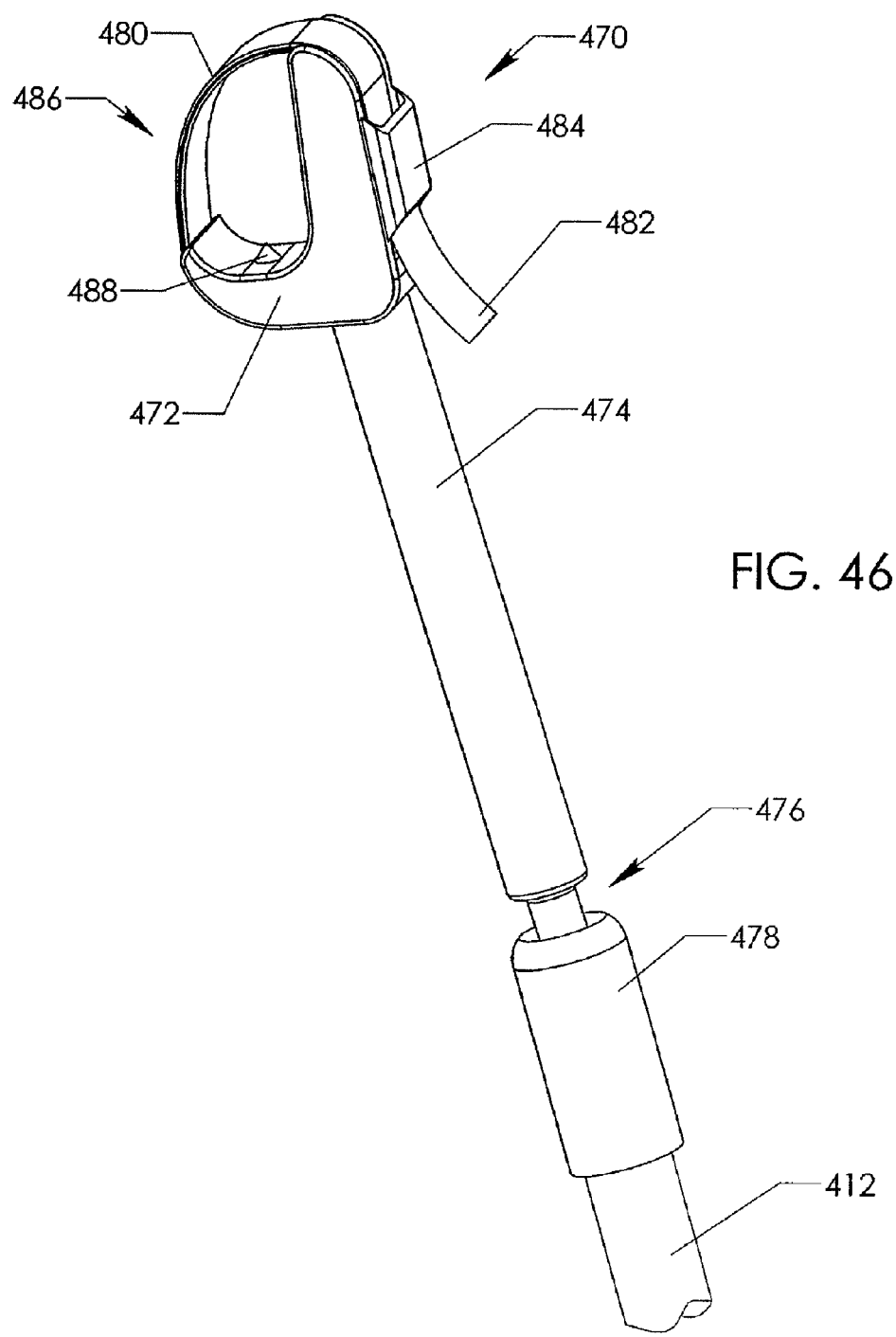
FIG. 46 illustrates a clamp used to affix, the distraction device to a patient's anatomical structure according to another embodiment.

FIG. 46 illustrates another embodiment of a clamp 470 that can be used to secure one end of the distraction device 400 to a rib or transverse process. The clamp 470 includes a "J-shaped" bracket 472 that is mounted on a shaft 474. The shaft 474 terminates at a swivel joint 476 that provides swiveling movement between a coupler 478 and the clamp shaft 474. The coupler 478 is configured to receive one end of the distraction rod 412 (e.g., using threads, mounting screw(s), adhesive, cement, laser weld, or the like). The clamp 470 includes a band 480 secured to one end of the J-shaped bracket 472. The band 480 is flexible in nature includes a free end 482 that is insertable into a lock 484 disposed on the J-shaped bracket 472. The band 480 may be made from a polymeric material or even a metallic material. The band 480 preferably has a small thickness that minimizes the amount of material that is exposed to the front side of the patient. Because the patient's lungs are located somewhat near the front portion 486 of the clamp 470, it is preferred to keep the amount of material in this section of the clamp 470 to a minimum. The band 480 provides the ability to ensure that the clamp 470 is secured to the rib or other anatomical structure.

The clamp 470 that is illustrated in FIG. 46 has a hand 480 that bends about the clamp 470 from the front of the patient to the back of the patient and is referred to as a "front-to-back" clamp. While the clamp 470 may be constructed as a "back-to-front" clamp in an alternative embodiment, this is not preferred because of the added material thus points toward sensitive organs (e.g., lungs) of the patient. In one embodiment, the clamp 470 further includes an optional detent 488 or other protuberance on the J-shaped bracket 472 that aids in fixedly securing the clamp 470 to the rib or other anatomical structure.

Figure 48:
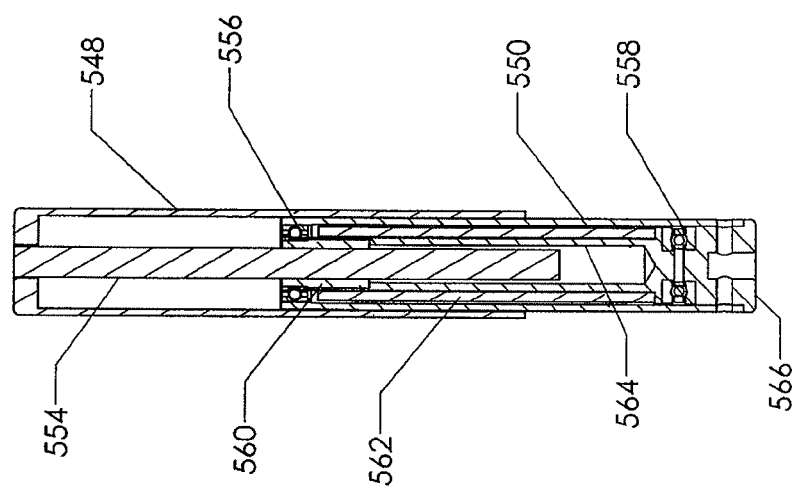
FIG. 48 illustrates a cross-sectional view of the adjustable portion of FIG. 47 taken along the line 48-48 of FIG. 47.
Figure 47:
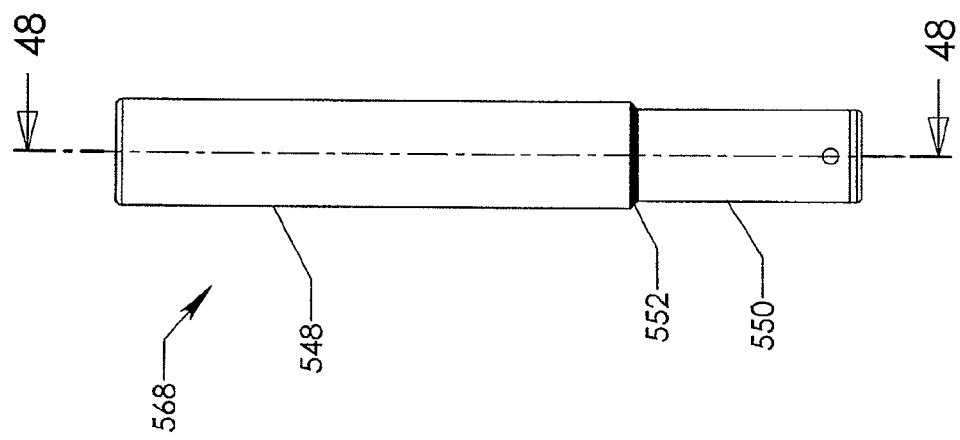
FIG. 47 illustrates an adjustable portion of a distraction device according to one embodiment.

FIGS. 47 and 48 illustrate an alternative embodiment of an adjustable portion 568 that is used in connection with a distraction device 400 utilizing a hollow magnet 562 (FIG. 48). While the description of the adjustable portion 568 is given in the context of the dish-action device 400, it should be understood that the alternative embodiment may apply equally to other distraction devices described herein (e.g., distraction devices 140, 314, 1414, etc.). As seen in FIGS. 47 and 48, the adjustable portion 568 is contained within two slidable sections which include an outer tube 548 and an inner tube 550. The outer tube 548 and inner tube 550 are moveable relative to one another as explained below. As best seen in FIG. 48, a hollow magnet 562 is mounted on an inner sleeve 564 and a nut 560 having internal threads thereon. That is to say that the inner sleeve 564 and nut 560 are entirely or at least partially disposed within the hollow portion of the magnet 562. The hollow magnet 562, inner sleeve 564, and nut 560 rotate together in unison, between opposing ball bearings 556, 558. An end cap 566 holds the assembly together. In this embodiment, the hollow magnet 562 permits the lead screw 554 to pass through it, thereby lessening the necessary total length of the adjustable portion 568, and thus the length of a larger diameter portion of the distraction device 400. Rotation of the hollow magnet 562 effectuates rotation of the nut 560 that depending on the direction of rotation, either pulls inward or pushes outward the lead screw 554 which engages with the internal threads (not shown) of the nut 560. While FIG. 48 illustrates a completely hollow magnet 562, some of the reduced length benefits discussed above may still be gained if only a portion of the magnet 562 were hollow or contained a recess configured to receive the lead screw 554. The magnet 562 is advantageously a permanent magnet and may be formed from the materials described herein with respect to the other embodiments. Still referring to FIG. 48, a dynamic seal 552 is provided at the interface between the outer tube 548 and the inner tube 550 to ensure that no body fluids enter the assembly.

FIGS. 49 and 50 illustrate still another embodiment of an adjustable portion 570. This embodiment is longer but thinner as compared to the adjustable portion 468 illustrated in FIGS. 47 and 48. Again, it should be understood that the alternative embodiment of the adjustable portion 570 may apply to other distraction devices described herein (e.g., distraction devices 140, 314, 1414, etc). As seen in FIGS. 49 and 50, the adjustable portion 570 is contained within two slidable sections which include an outer tube 572 and an inner tube 574. The outer tube 572 and inner tube 574 are moveable relative to one another as explained below. As best seen in FIG. 50, a rotatable magnet 576 is held within a magnetic cup 580 which rotates on a thrust beating 582. The magnet 576 is operatively coupled to a lead screw 578 that rotates along with the magnet 576 in response to an externally applied magnetic field as described herein. The adjustable portion 570 does not include an inner sheath such as that illustrated in the prior embodiment (FIGS. 47 and 48) thereby enabling a thinner profile. In this embodiment, the nut 584 is affixed to the inner tube 574. Rotation of the magnet 576 causes rotation of the lead screw 578 which then pulls or pushes the inner tube 574 relative to the outer tube 572. A dynamic seal 586 is provided at the interface between the outer tube 572 and the inner tube 574 to ensure that no body fluids enter the assembly.

In any of the above-described embodiments, the external adjustment device (e.g., external adjustment device 1130) may optionally include a vibrator attached thereto that transmits vibrational motion to the adjustable portion 570 (or other adjustable portions described herein) which lessens frictional effects on the components giving them less resistance. For example, vibration may enhance or better enable axial motion of the outer tubes 448, 572 and inner tubes 450, 574, respectively and enhance freer rotation of the rotational components. The vibrational motion may also be delivered via a separate vibrator device that is separate from the external adjustment device.

Figure 51:
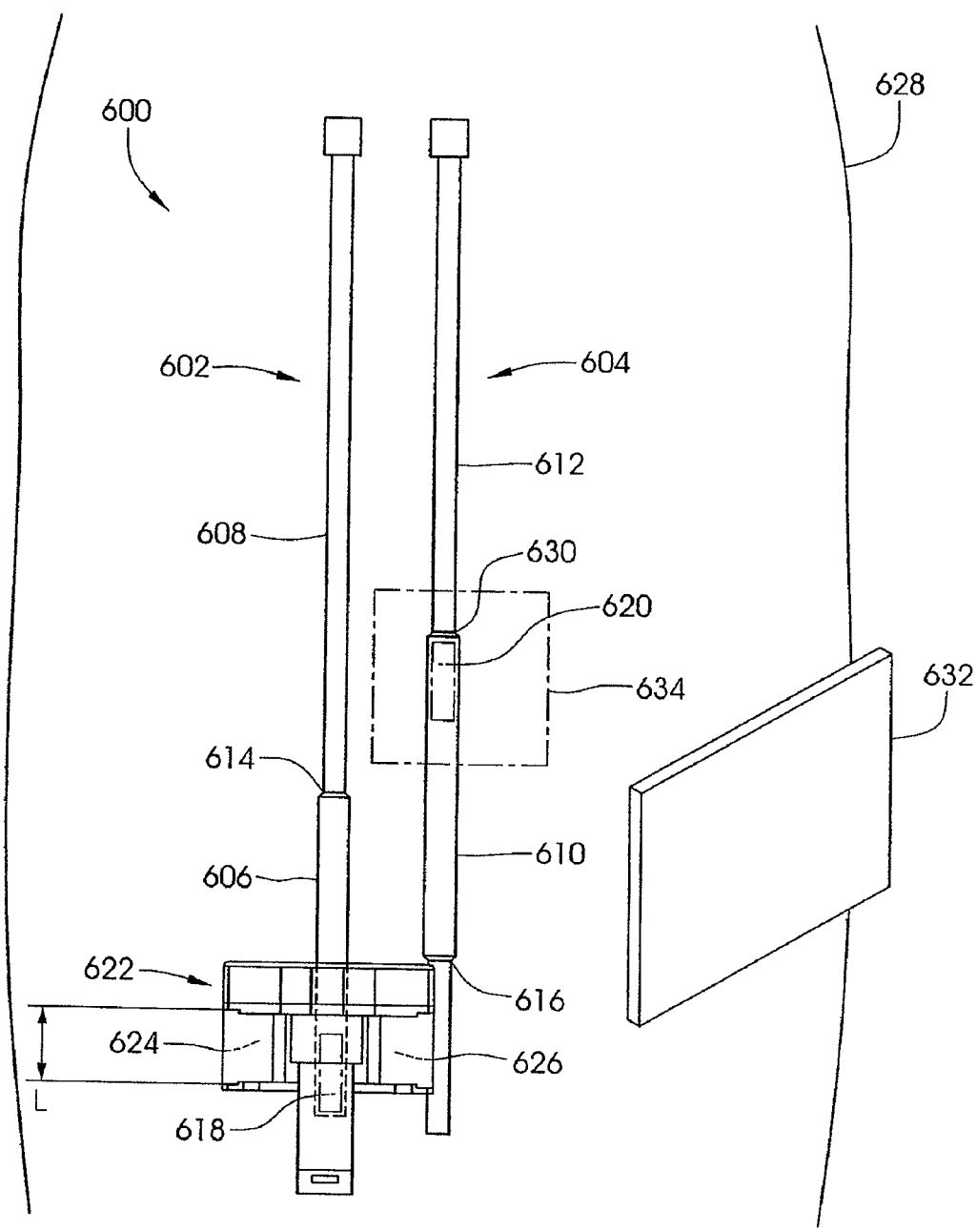
FIG. 51 illustrates an embodiment of a distraction device that includes two (2) adjustable rods, which each rod being independently adjustable.

FIG. 51 illustrates another embodiment of a distraction system 600 undergoing adjustment. In this embodiment, the implanted distraction system 600 includes two distraction devices 602, 604. The first distraction device 602 includes a first adjustable portion 606 and a first rod 608. The first adjustable portion 606 is similar to the adjustable portion 570 of FIGS. 49 and 50, with a first cylindrical permanent, magnet 618 located at a far end of the first adjustable portion 606. The distraction system 600 includes a second distraction device 604 having a second adjustable portion 610 and a second rod 612. The second adjustable portion 610 is oriented in an inverted relation with respect to first adjustment portion 606, so that a second cylindrical permanent magnet 620 is not at the same level on the body 628 (e.g., height if the subject is standing up) as the first cylindrical permanent magnet 618. In this regard, the first and second cylindrical permanent magnets 618, 620 are offset from one another relative to their location vis-à-vis the spine. For instance, the second cylindrical permanent magnet 620 is located higher on the body 628 when compared to the first cylindrical permanent magnet 618.

Due to this inversion, the point of telescopic displacement 614 of the first distraction device 602 is also at a different level on the body 628 than the point of telescopic displacement 616 of the second distraction device 604. Due to the oftentimes asymmetric nature of the scoliosis, it may be desired to adjust each of the distraction devices 602, 604 independently from the other. As seen in FIG. 51, an external adjustment device 622 is provided that includes a first permanent magnet 624 and a second permanent magnet 626 that can be selectively placed at the proper level (e.g., height) along the body 628 corresponding to the location of the permanent magnet 618, 620 of the respective distraction device 602, 604 intended for adjustment. The length (L) of each of the permanent magnets 624, 626 of the external adjustment device 622 is preferably longer than the length of the permanent magnet 618, 620 for maximal coupling, yet short enough, for example, one (1) inch long, so that the operation of the external adjustment device 622 allows the permanent magnets 624, 626 to sufficiently couple with the first cylindrical permanent magnet 618, without sufficiently coupling with the second cylindrical permanent magnet 620. It should be noted, that in the inverted version, the second adjustable portion 610 is permanently attached to the second rod 612 at joint 630.

Still referring to the embodiment, of FIG. 51, it may be desired to adjust the distraction length (or force) of the first distraction device 602 a certain amount followed by adjustment of the distraction length (or force) of the second distraction device 604. This may be accomplished by first placing the external adjustment device 622 over the first adjustable portion 606 which contains the first permanent magnet 618. The external adjustment device 622 may then be operated to rotate the first permanent magnet 618 with the appropriate number of rotations, or partial rotation as the case may be, to achieve the desired distraction length or force. The external adjustment device 622 may be operatively coupled with a PLC 1080 such as mat illustrated in FIG. 14 to automatically adjust the external adjustment device 622, For instance, using the PLC 1080, the external adjustment device 622 may be input, to adjust the first distraction device 602 one (1.0) mm. Optionally, external adjustment device 622 and/or PLC 1080 may operate under feedback control. For instance, the acoustic feedback modality described with respect to FIGS. 15-30 may be used to listen for an acoustic signal (e.g., clicks). As another alternative, an optical feedback, force feedback, or magnetic Hall effect feedback control may be used to provide feedback control of the external adjustment device 622.

Once the first adjustable portion 606 has been adjusted as desired, the external adjustment device 622 is moved over the second adjustable portion 610 which contains the second permanent, magnet 620, for example directly over the permanent magnet 620. The external adjustment device 622 may then be operated to rotate the second permanent magnet 620 with the appropriate number of rotations, or partial rotation as the case may be, to achieve the desired distraction length or force. For instance, the external adjustment device 622 may be input to adjust the second distraction device 604 one-half (0.5) mm. This may be conducted as described above with respect to the first distraction device 604, including the option, use of the PLC 1080 with feedback control.

While the independent adjustment described above pertains to application of a particular distraction distance (e.g., 1 mm or 0.5 mm), it should also be understood that the external adjustment device 622 may be used to adjust the first distraction device 602 to a different distraction force than the second distraction device 604. For instance, the first distraction device 602 may be adjusted to have a force of 40 pounds, while the second distraction device 604 may be adjusted to 30 pounds. Of course, one alternative is leave on the distraction devices 602, 604 at its current or then-current setting with adjustment only Wing performed on the other distraction device 602, 604.

In still another embodiment, a magnetic shield 632 is used that permits the first and second cylindrical permanent magnets 618, 620 to be closer to one another. For example, if it is desired to adjust the first distraction device 602 and not the second distraction device 604, the magnetic shield 632 is placed at location 634. The external adjustment device 622 is placed with its permanent magnets 624, 626 in proximity to the first cylindrical permanent magnet 618. The magnetic shield 632 diminishes the ability for the permanent magnets 624, 626 to be able to magnetically couple with the second cylindrical permanent magnet 620. The magnetic shield 626 may then be placed at a different, location, closer to the first cylindrical permanent magnet 618, in order to independently adjust the second cylindrical permanent magnet 620. The magnetic shield 632 may be made from nickel, iron, steel or a nickel-iron alloy such as Mu-Metal, for example 75% Nickel/15% iron. Other materials with similar magnetic shielding properties may also be used.

Figure 52:
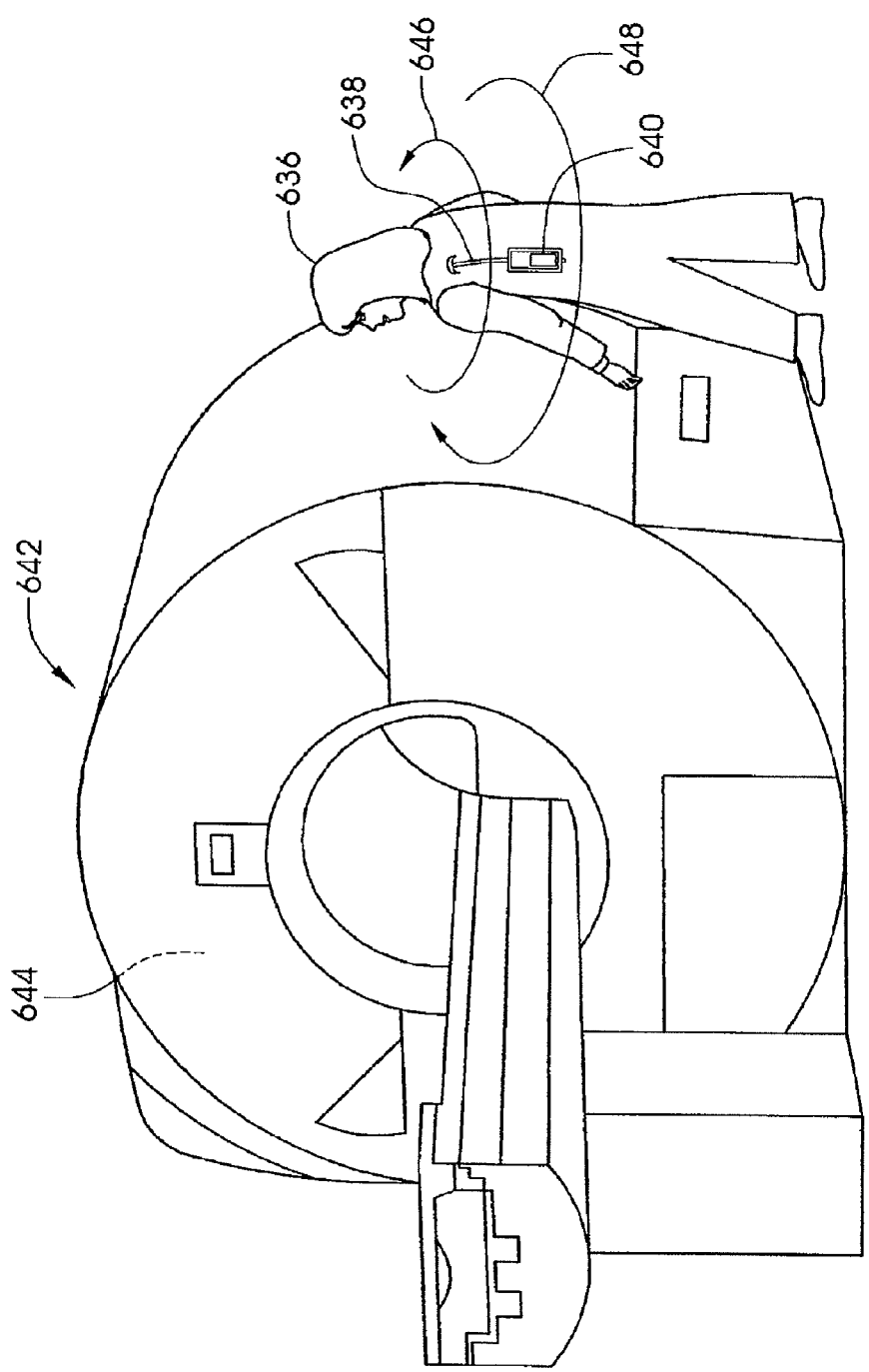
FIG. 52 illustrates a technique of performing an emergency adjustment of a magnetically-actuated distraction device.

FIG. 52 illustrates another embodiment of a technique for the emergency adjustment of a distraction device 638. As seen in FIG. 52, the patient 636 has an implanted distraction device 638 similar to those described herein. In some instances, the patient 636 may be in need of emergency adjustment due to any number of reasons including, for example, incorrect prior adjustment, trauma, bone, joint muscle or connective tissue pain, pregnancy, or growth.

If the patient 636 arrives at a hospital that does not have the external adjustment device 1130, 622 available for use, the implanted distraction device 638 containing the cylindrical permanent magnet 640 may be adjusted by using a magnetic resonance imaging (MRI) seamier 642—a diagnostic instrument that is commonly found in hospitals. Magnetic resonance imaging (MRI) scanners 642 contain a primary magnet 644 comprising a supercooled electromagnetic coil. The primary magnet 644 is designed to be "always on", except in cases of maintenance or malfunction. The primary magnet 644 generates a very large magnetic field (i.e., magnetic flux density). Older MRI scanners had magnetic fields of 0.2 Tesla, for example, but most today have fields of 1.5 Tesla or 3 Tesla while still others are 7 Tesla.

Generally, all of these fields will strongly orient a cylindrical permanent magnet 640, 394 so that it is aligned with the magnetic field of the primary magnet 644 if it is near the MRI scanner 642. It should be understood that while a description is given with respect to driven magnet 640, the acoustic sensing features may also apply to magnetic element 218 of FIGS. 6C-6G, the internal magnet 1064 of FIGS. 13A-13D, and 14, the internally located driven magnet 1402 of FIG. 35, cylindrical magnet 394 of FIGS. 41, 42, and 44, the hollow magnet 564 of FIG. 48, magnet 576 of FIG. 50, magnet 262 of FIG. 53, magnets 618, 620 of FIG. 51, and magnet 1302 of FIGS. 15-30.

The torque required to turn the cylindrical permanent magnet 640 into a different orientation than the MRI aligned orientation would be significantly high, and much greater than the rotational resistance of the cylindrical magnet assembly. Therefore, by placing a patient 636 close to the primary magnet 644 of the MRI scanner 642 (for example, at a distance of ten feet or less, or more specifically five feet or less) and by turning the body of the patient in either a first rotational direction 646 or a second rotational direction 648, the implanted distraction device 638 may be adjusted without the need of an external adjustment device 1130, 622. Generally, the patient turns or rotates him or herself about an axis of rotation (which may change slightly during the rotational procedure). For example, the patient may stand on their feet and turn their body. Alternatively, the patient may sit in a swivel chair, for example a chair made of MRI safe materials such as aluminum, and the chair may be spun in the desired direction. If patient turns or is turned in first rotational direction 646, the distraction is reduced. If patient turns or is turned in second rotational direction 648, the distraction is increased. It is desirable that the implanted distraction device 638 is well secured to the patient 636, for example with pedicle screws, hooks or clamps, so that the attraction of the cylindrical permanent magnet 640 to the primary magnet 644 of the MRI device does not cause unsafe displacement of the implanted distraction device 638 at its fixation points. Additionally it is preferable to use mostly non-magnetic materials in the implant, such as Titanium or Titanium alloys such as Ti-6AL-4V, so that the implant itself is not strongly attracted to the primary magnet 644. If the implanted distraction device 638 uses acoustic feedback, such as that described in FIGS. 15 through 34, medical personnel may listen, to the patient with an MRI safe stethoscope to confirm that clicks are heard, which would indicate that the magnet 640 is indeed turning. The clicks may also be counted in order to quantify the amount of adjustment precisely.

The above-described use of the primary magnet 644 to adjust the magnet 640 of the distraction device 638 may also be employed in other implantable devices that utilize a rotating or cyclically-movable magnet. For instance, the implantable device may include a restriction device (e.g., gastric band or annuloplasty ring), or a valve, or the other devices. Examples of such devices that may be adjusted in this manner may be found in U.S. Patent Application Publication Nos. 2008/0097487 and 2008/0097496. For this method to work, it should be noted that the magnets don't have to be cylindrical, but the axis of magnetization should not be parallel to the axis of rotation.

As mentioned, one of the benefits of a fully fushionless procedure is the ability to remove the implants after the spine has been able to be manipulated by the initial surgery and the non-invasive adjustments of the distraction device. The embodiments described herein allow for a completely adjustable scoliosis treatment system, which can achieve the goal of a straightened spine and no lifetime implant through a total of two surgical procedures; one procedure to implant the device and one procedure to remove the device. This is a significant improvement to the adjustable scoliosis treatment devices which have been proposed, and require adjustment techniques utilising surgical incisions. It should be noted that after the initial implant procedure, the physician may desire to have the patient use a brace for a one or a few months, in order to protect the healing process. This protective brace serves a different purpose than the scoliosis braces that attempt to affect the patient's Cobb angle.

It is envisioned that patients may be identified for their genetic susceptibility to scoliosis and treated with a distraction device as described herein. For example, a genetic test may identify that a particular subject that has a current Cobb angle of less than or equal to 30° is predisposed or otherwise at risk for his or her Cobb angle to increase beyond this initial angle (e.g., increase to or beyond 40°). In this regard, a genetic test may be run on the patient's nucleic acid (e.g., DNA or RNA) to identify genes or gene sequences that are associated with this predisposition. If the patient has this genetic susceptibility, a distraction device of the type described herein may be used to preemptively correct or mitigate the anticipated spinal malformation. For example, Gao et al. have been reported that CHD7 gene polymorphisms are associated with susceptibility to idiopathic scoliosis. Gao et al., CHD7 Gene Polymorphisms Are Associated with Susceptibility to Idiopathic Scoliosis, American Journal of Human Genetics, Vol. 80, pp. 957-65 (May, 2007). The above-noted Gao et al. publication is incorporated herein as if set forth fully herein. In particular, the CHD7 gene spans 188 kb and contains one non-coding exon and thirty-seven coding exons. The SNP loci associated with idiopathic scoliosis were contained within an ~116 kb region encompassing exons 2-4 of the CHD7 gene. For example, the genetic test may look for the SNP loci discussed above which are associated with IS susceptibility.

Though many of the embodiments described herein have generally been in the area of adolescent idiopathic scoliosis and early onset scoliosis treatment, it is contemplated that the devices and methods described herein also have application in the treatment of adult scoliosis. Adult scoliosis can continue to worsen with time. Though the adult is skeletally mature, the Cobb angle may still continue to increase with time. The relaxation or slight reduction in height that occurs in adults may have some relation with this increase in Cobb angle. Curves above 100° are rare, but they can be life-threatening if the spine twists the body to the point where pressure is put on the heart and lungs. The devices and methods described herein can also be used to treat adult scoliosis, e.g., allowing adult scoliosis to be treated with a minimally invasive and/or fusionless approach. In addition, gradual adjustment of the spine may be desired, especially in the cases of very high Cobb angles. For example, it may be desired to limit the amount of stresses on the bones or on the implant materials, by first adjusting an adult scoliosis patient so that their Cobb angle is reduced 50% or less, then 15% or less each few months, until the spine is straight. As one example, the initial surgical implantation may reduce the Cobb angle by 50% or more by the physician performing manual distraction on the spine. Post-Implantation, the Cobb angle can be reduced in a non-invasive manner by application of a constant or periodically changing distraction force. A first non-invasive adjustment may result in a Cobb angle reduction of less than 50%. Additional non-invasive adjustments may be performed which result in even smaller Cobb angle reductions (e.g., less than 15% from original Cobb angle).

In this regard, the Cobb angle may be reduced by a smaller amount over the next few months (e.g., less than around 15% each month post-operation). The non-invasive adjustment of a fusionless implant made possible by the invention allows tor a gradual adjustment scheme of this nature. Moreover, the distraction forces used over this period of time are generally low (e.g., distraction force less than 45 pounds) which means, among other things, less patient discomfort, and less chance of failure within the adjustable rods 142, 144. Non-invasive adjustments may be periodically performed when the patient visits his or her physician. This may occur over a span of more than one week (e.g., a several week process). Of course, the number and periodicity of the adjustments is a function of, among other things, the Cobb angle of the patient.

Oftentimes, the adult spine has less dense or even osteoporotic bone, so it may be desirable to combine the sort of gradual adjustment described here with additional methods to strengthen the bone, for example the bone of the vertebral bodies. One method is to strengthen the vertebral body by performing prophylactic vertebroplasty or kyphoplasty, wherein the internal area of the vertebral body is strengthened, for example by injection of bone cement or Polymethyl Methacrylate (PMMA). Additionally, if pedicle screws are used for fixation, foe surface of the screws may be treated with a biologic material that promotes bone growth, or a surface characteristic that improves bone adhesion. Any of these methods would further improve the possibilities that the distraction forces would not cause fracture or other damage to the vertebrae of the patient.

Another embodiment includes a bone growing implant, wherein the manipulation of a portion of the skeletal system is limited to a single bone, and the bone growing implant is a distraction device, capable of distracting a first and second locations located on or in the same bone. For example, in many cases of dwarfism, the femur and the humerus bones are short in relation to the other bones. Currently these bones may be grown longer using a device such as the Taylor Spatial Frame, which is an external frame having wires or pins that extend through the skin and attach to the bone. The frame can be continually adjusted by the external adjustment knobs to stimulate bone growth in the desired direction. This device may also be used on patients whose bones stop growing due to, for example, pediatric bone cancer, such as Swing's sarcoma or osteosarcoma. Another application for this device is in patients who have had broken bones which are healing in an unsatisfactory manner, for example, in the case of one leg that is shorter than the other because of a badly healed femur fracture. One problem that is seen with the Taylor Spatial Frame is the occurrence of pin tract infections, which occur because there is an open channel for bacteria to enter from the outside of the patient to the bone. Another application for bone growth is for selective growth to only one side of the hone, for example in Blount's disease (bowleggedness), in which one side of the bone grows normally while in the other side there is an arrest in the growth plate.

Figure 53:
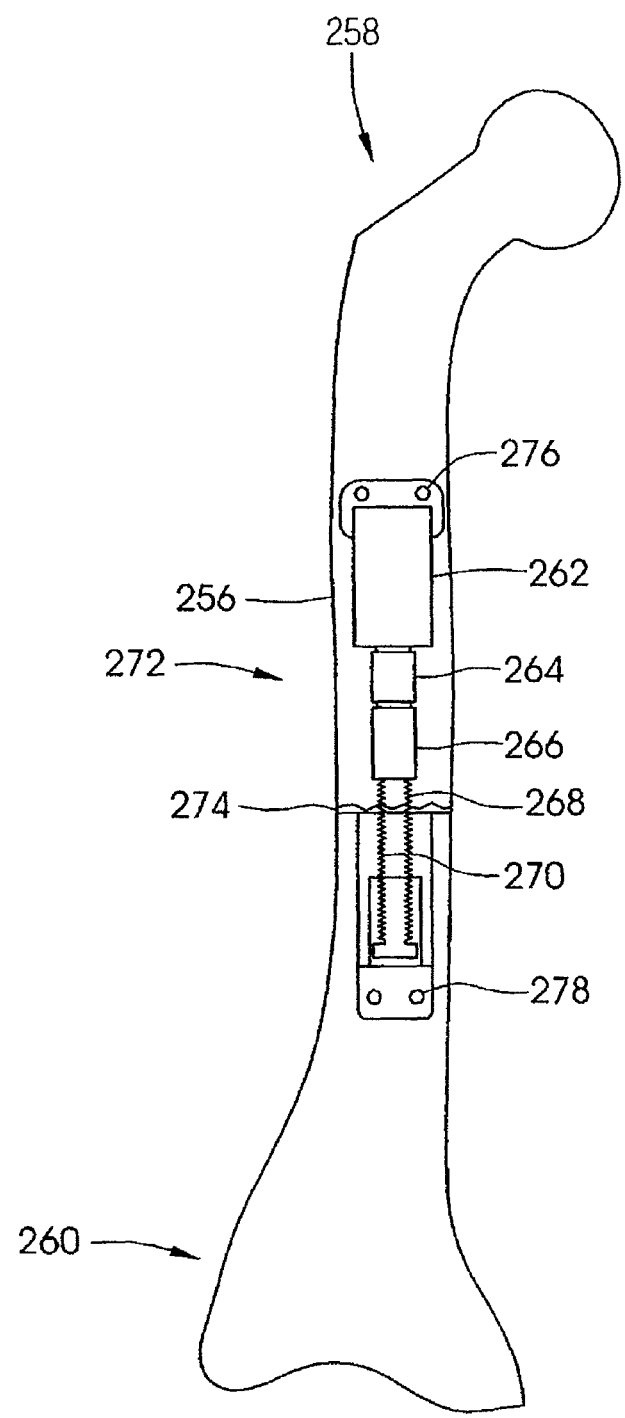
FIG. 53 illustrates an embodiment of a distraction device disposed on a bone.

In all of these bone growth applications, a non-invasively adjustable bone growth distraction device is needed. A device of this nature is presented as an embodiment of this invention in FIG. 53. A bone growth distraction device 272 is attached to bone 256 having a proximal portion 258 and a distal portion 260 by a proximal securement member 276 and a distal securement member 278. The securement members 276, 278 may operate using any number of securement devices or methods known to attach a device to bone, including screws, clamps or even adhesive materials. In cases of a bone fracture, a fracture site 274 is Illustrated, though it should be noted that this fracture is not always present in some of the applications previously mentioned. As seen in FIG. 53, the bone growth distraction device 272 includes a cylindrical magnet 262 that is configured to rotate on its axis in response to an externally applied magnetic field (as described above in the context of other embodiments). Rotation of the cylindrical magnet 262 effectuates rotation of a planetary gear set 266. An optional slip clutch 264 is illustrated as being disposed between the cylindrical magnet 262 and the planetary gear set 266, though slip clutch 264 may be disposed at any other location along the drive transmission. Rotation of the planetary gear set 266 in a first direction (e.g., either clockwise or counter-clockwise depending on configuration) causes lead screw 268 to turn within internal thread 270 causing distraction (e.g., elongation) of the bone 256. Bone growth distraction device 272 may be implanted in a single operation. Subsequent adjustments are performed non-invasively, and if desired can be performed frequently in order to precisely control bone growth. An adjustment device such as external adjustment device 1130 described herein may be used, to rotate the cylindrical magnet 262. The cylindrical magnet 263 may be dimensioned and made of the same materials as described herein with respect to the other embodiments.

Figure 54:
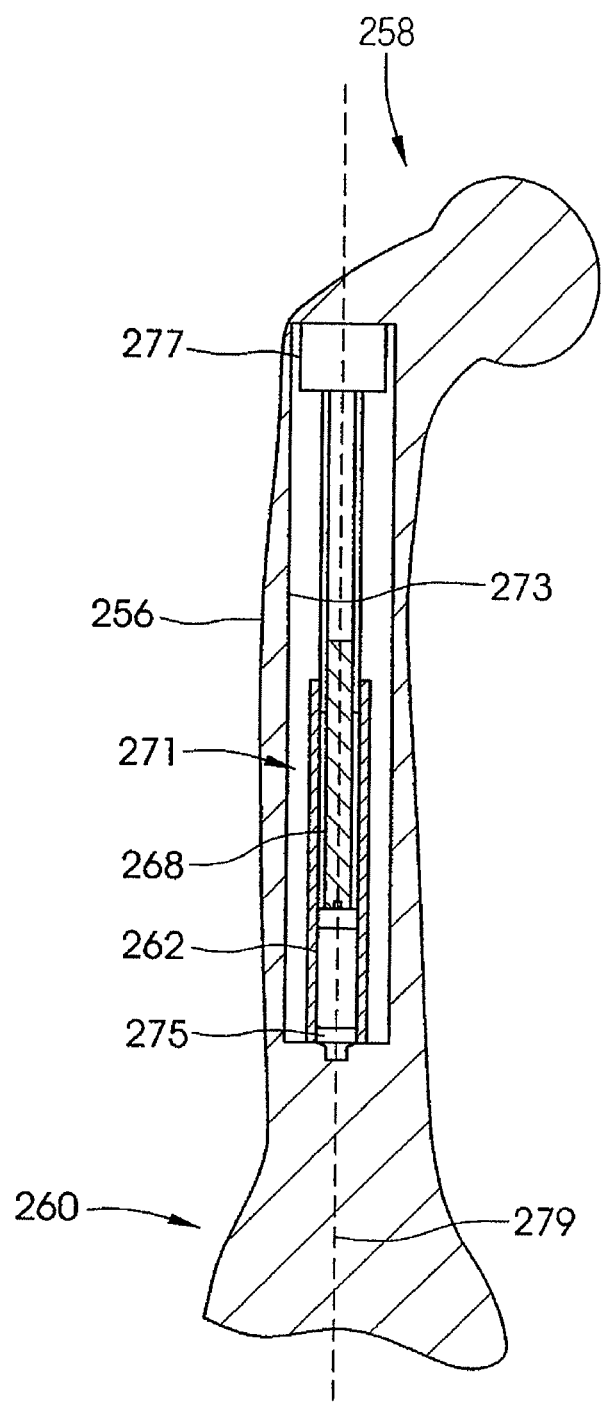
FIG. 54 illustrates an embodiment of a distraction device disposed within the intramedullary canal of a bone.

While FIG. 53 may be especially effective in treating Blount's disease, or any other condition that requires selective growth (for example on one side of the bone), FIG. 54 illustrates an alternative embodiment of the invention incorporating an intramedullary magnetic elongation device. Bone distraction device 271 is placed within the intramedullary canal 273 and secured at first attachment point 275 and second attachment point 277. By being centered within the intramedullary canal 273, the bone distraction device 271 is capable of lengthening the bone 256 substantially parallel to its longitudinal axis 279. It should be understood that the embodiments described herein may be applicable to bones and/or skeletal structures other than those specifically described or illustrated in the drawings. For instance, the embodiments may be utilized in the tibia, mandible, jawbone, and the like.

Figure 55:
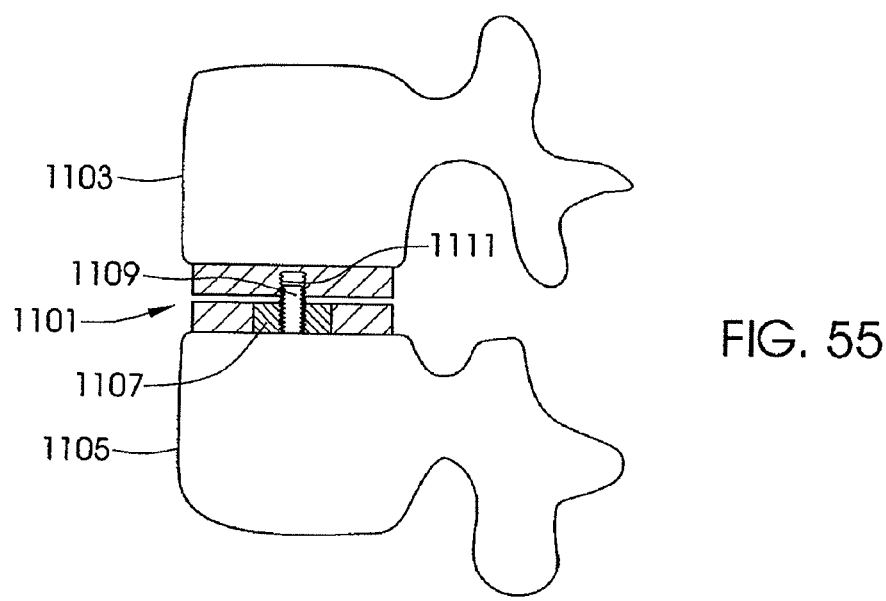
FIG. 55 illustrates an embodiment of a distraction device for intervertebral placement.

Other orthopedic distraction devices are conceived using the present invention. FIG. 55 illustrates a distraction device 1101 configured for replacement of an intervertebral disk, and for distraction between a first, vertebral body 1103 and a second vertebral body 1105. Intervertebral disks can degenerate, bulge, herniate or thin, and cause accompanying back pain. Degenerative disk disease (ODD) has caused a large increase in the use of intervertebral disk replacement devices. Current intervertebral disk replacement devices have had incomplete success, due to a large rate of patients whose pain returns with time. The inventive art describes an intervertebral disk replacement device that allows for additional adjustment after disk replacement surgery and after the healing period. If a patient has recurring pain, the device may be adjusted non-invasively to increase or decrease distraction in order to eliminate recurrent pain. Using the external adjustment device 1130 in the same non-invasive manner as the other embodiments an internal magnet 1107 is non-rotated. Internal magnet 1107 is coupled to lead screw 1109 so that rotation motion changes the displacement between lead screw 1109 and the female thread 1111 inside a portion of the distraction device 1101.

This technique may also be used to treat other spinal problems, such as spondylolisthesis. In certain situations, the entire vertebral body may be removed, for example due to a crushed, fractured or diseased vertebral body. The embodiment of FIG. 55 may be supplied in a number of sizes, for example thicknesses, in order to fill the desired dimension between the other vertebral bodies.

Figure 56:
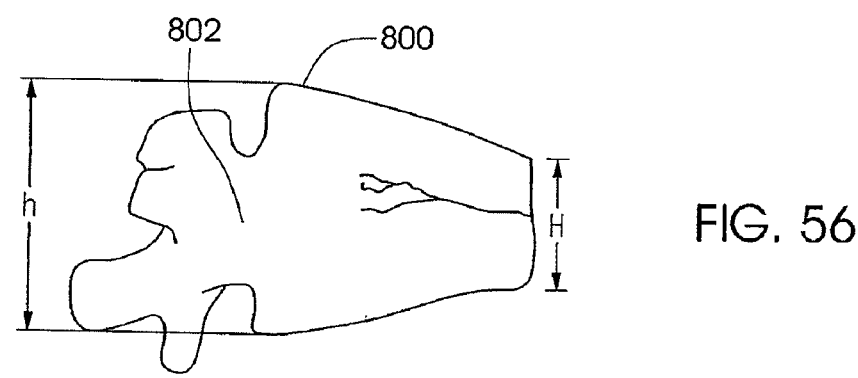
FIG. 56 illustrates a fractured vertebral body.
Figure 57:
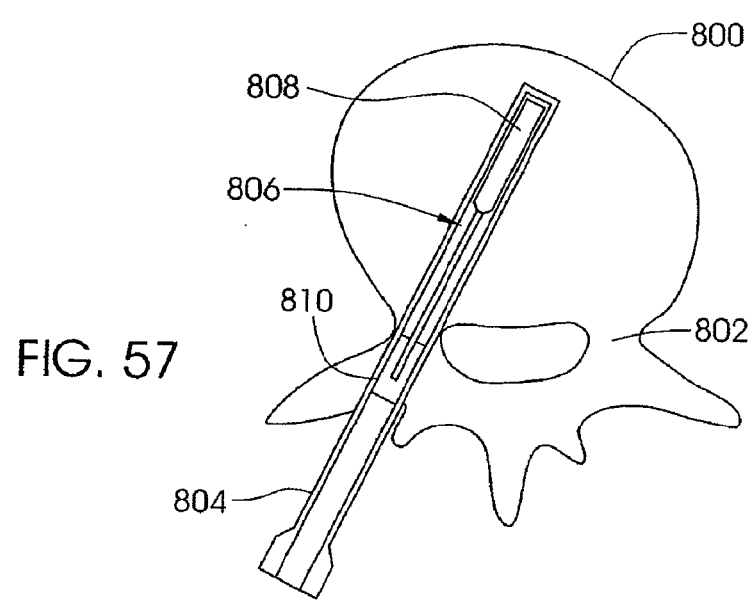
FIG. 57 illustrates a distraction device being placed into the vertebral body of FIG. 56.
Figure 58:
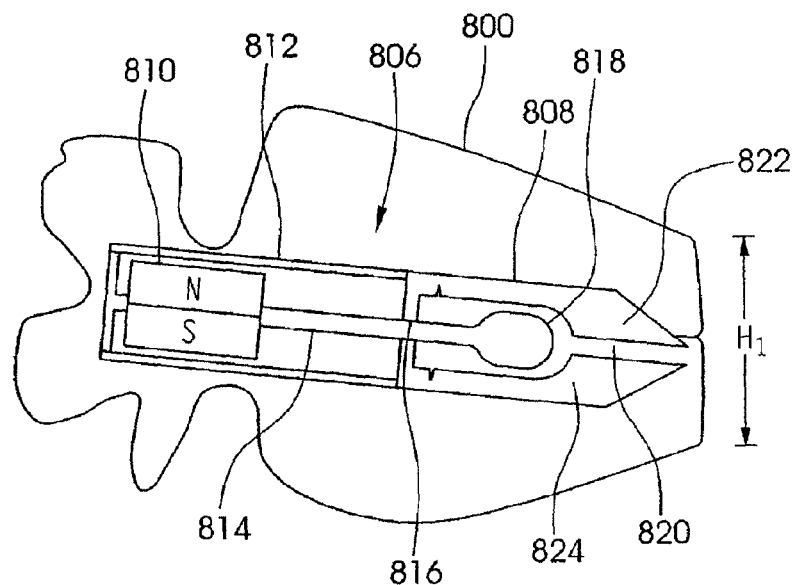
FIG. 58 illustrates a distraction device within a vertebral body.
Figure 59:
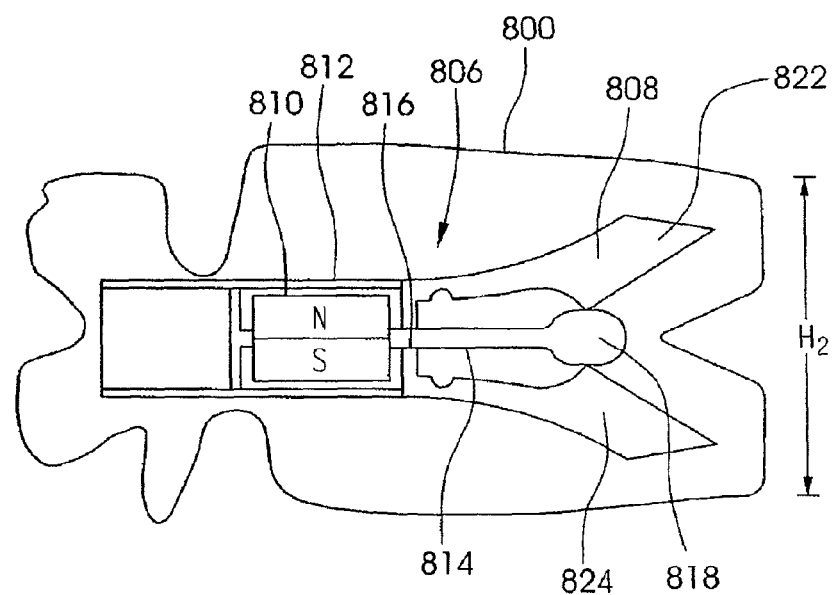
FIG. 59 illustrates a distraction device manipulated to add height to a vertebral body.

FIGS. 56 through 60 illustrate a device for modification of a fractured vertebra is illustrated. Vertebrae can become weak with osteoporosis, and may fracture easily, causing an increased kyphosis and increasing the risk of fracture of subsequent vertebrae. Fractured vertebral body 800 is illustrated in FIG. 56. The fracture shown is a wedge fracture, which is very common in this type of patient. Anterior height H has been significantly reduced in comparison to original height h. Currently, fractured vertebrae can be treated by a vertebroplasty procedure, in which cement, for example polymethyl methacrylate (PMMA) is injected into the inside of the vertebral body. Vertebroplasty does very little in terms or restoring height. An alternative method known as kyphoplasty is sometimes performed during which a balloon is inflated inside the vertebral body to crush in inner bone material prior to filling with the cement. Kyphoplasty has shown to increase height slightly, but the height gain is still considered unsatisfactory by many surgeons. In an alternative embodiment of the invention illustrated in FIG. 57 a hole is drilled through one of the pedicles 802 which lead to the vertebral body 800. Cannula 804 is placed through the hole and distraction device 806 is placed through the cannula 804. If desired, a kyphoplasty balloon may be placed through the cannula first in order to pre-dilate. Cannula. 804 may be partially or completely removed at this point. Distraction device 806 comprises a protective sheath 812, a distraction head 808 and a cylindrical magnet 810. Protective sheath 812 is configured to be secured inside of pedicle 802 and/or inside vertebral body 800. Cylindrical magnet 810 is free to rotate within protective sheath 812 and is coupled to externally threaded shaft 814. As cylindrical magnet. 810 is rotated by an external rotating magnetic field (for example that, from external adjustment device 1130) threaded shaft 814 rotates within internal thread 816 causing threaded shaft 814 to extend axially. As threaded shaft 814 extends, dilating tip 818 is forced through separation 820, forcing apart first distractor 822 and second distractor 824 and increasing the height of the fractured vertebral body from $H_1$ to $H_2$. It can be appreciated that the external adjustment device 1130 can apply a significant, torque to the cylindrical magnet 810 and thus allow a high separation force applied to the two distractors 822, 824 of the distraction head 808. Several options are now possible at this point.

In the first option, the cylindrical magnet 810 may be removed from the assembly and cement may be applied through the protective sheath 812 to fully set the vertebral body in its distracted configuration, leaving, the protective sheath 812 and the distraction head 808 permanently implanted.

Figure 60:
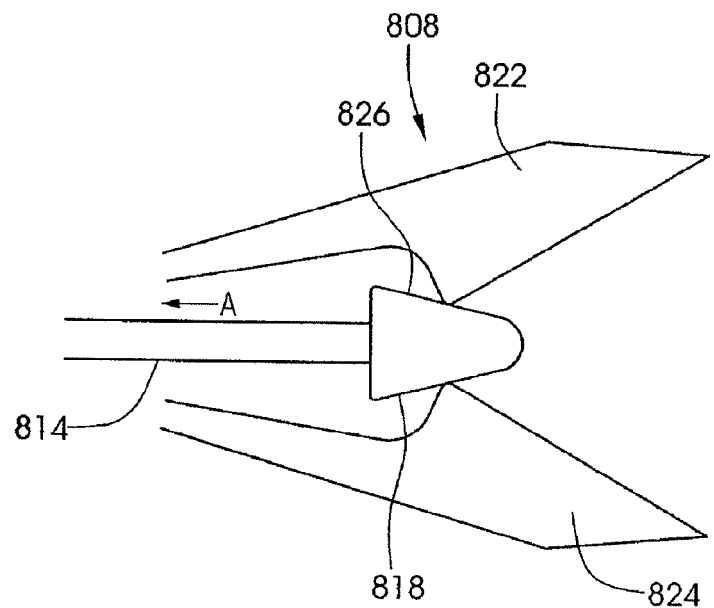
FIG. 60 illustrates an alternative configuration of a distraction device for use in a vertebral body.

In the second option, no cement is applied and the patient is recovered with the entire distraction device 806 intact. After reviving from anesthesia, and most likely also following recovery from the normal pain that accompanies post-surgery, the patient returns for a non-invasive adjustment. Wherein the distraction device is adjusted to the specific distraction height that most reduces pain. For example, FIG. 60 shows the dilating tip 818 having a tapered outer diameter 826. By adjusting the distraction device 806 in either direction, the extent of the spread of the two distractors 822, 824 can be controlled. Though the distraction head 808 may be made from numerous metallic or polymeric materials, it may be preferably made of a highly elastic metal, such as nickel-titanium, so that the two distractors 822, 824 will return towards their original unexpanded configuration as the dilating tip 818 moves in direction A. This entire non-invasive adjustment process has not been possible with prior devices which could only be manipulated during surgery, when patient is unconscious. Once the patient is at a desired adjustment level with little or no pain, an additional procedure may be performed to remove the magnet and/or inject cement.

In the third option, me cement, is injected at the end of the initial implantation operation, but the distraction device 806 is left intact. It is common for cement to remodel or even recede, for example after 18 months. With the present invention, this is less likely, because the distraction head 808 in its expanded configuration serves as additional reinforcement. In addition, if the cement were to remodel or recede, an additional adjustment procedure can be performed during which the two distractors 822, 824 are further spread and more cement is injected.

Figure 61:
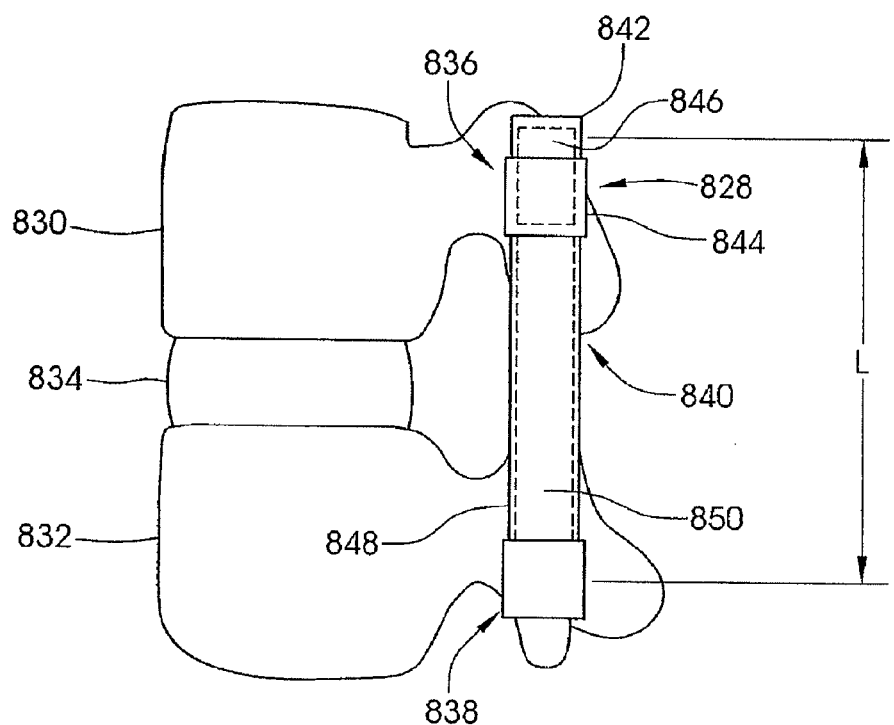
FIG. 61 illustrates a non-invasively adjustable dynamic stabilization device.

FIG. 61 illustrates the present invention incorporated into a motion preservation (or dynamic stabilization) device 828. The motion preservation device 828 is attached to a first vertebra 830 and a second vertebra 832 with pedicle screws. First and second vertebrae 830, 832 are separated by intervertebral disk 834. Second head 838 is static and is attached to second vertebra 832. First head 836 is adjustable and comprises first portion 842, which is attached to first vertebra 830 and second portion 844 which is can be adjusted by using external adjustment device 1130 to rotate internal magnet 846. Intermediate portion 840 comprises an outer spacer 848 and an inner cord 850. Outer spacer 848 and inner cord 850 are preferably made from polymeric materials that allow for some deformation and therefore limited movement between first vertebra 830 and second vertebra 832. By non-invasively adjusting first head 836 with the external adjustment device 1130, the length L can be manipulated so that the desired condition is reached wherein the range of motion allowed by the implant is tailored so that it is within the range of motion where no pain is encountered, and the range of motion for which pain is present is eliminated. Current dynamic stabilization devices do not have this noninvasive adjustability. Therefore, a surgeon is never sure whether the patient's device will maintain a range of motion for which patient feels no pain. The embodiment of this invention allows the ability to adjust the device while the patient is not under anesthesia and after the patient has recovered from any post-surgery pain, so that the real pain that is intended to be cured can actually be assessed.

While embodiments of the present invention have been shown and described, various modifications may be made without departing from the scope of the present invention. The invention, therefore, should not be limited, except to the following claims, and their equivalents.

What is claimed is:

1. A method of treating scoliosis in a skeletally mature subject having a Cobb angle greater than zero, the method comprising:

securing a scoliosis treatment device to first and second locations on the skeletally mature subject's skeletal system, the scoliosis treatment device comprising a first portion, a second portion moveably mounted relative to the first portion, and an adjustment device comprising a rotationally mounted magnetic element and being configured to change at least one of a distraction force and a distance between the first and second locations on the skeletally mature subject's skeletal system, wherein the scoliosis treatment device is configured to be non-invasively actuated by an external adjustment device comprising at least two rotating magnets generating a first magnetic field and a second magnetic field, wherein the scoliosis treatment device is configured to noninvasively change the Cobb angle of the skeletally mature subject from an initial Cobb angle to a final Cobb angle through actuation by the external adjustment device.

2. The method of claim 1, wherein the initial Cobb angle is more than about 40°.

3. The method of claim 2, wherein the initial Cobb angle is more than about 100°.

4. The method of claim 1, wherein the initial Cobb angle is greater than the final Cobb angle.

5. The method of claim 1, wherein, following a single non-invasive adjustment, the Cobb angle is reduced by at least about 50% of the initial Cobb angle.

6. The method of claim 5, wherein, following the single non-invasive adjustment, the Cobb angle is reduced by at least about 15% of the initial Cobb angle.

7. The method of claim 1, wherein the scoliosis treatment device is configured to be actuated using the external adjustment device at least twice, wherein the scoliosis treatment device is configured to reduce the Cobb angle by less than about 50% during the first actuation, and wherein the scoliosis treatment device is configured to reduce the Cobb angle by less than about 15% during each subsequent actuation.

8. The method of claim 7, wherein each actuation subsequent to the first actuation generates a distraction force between the first and second locations on the skeletally mature subject's skeletal system that is less than about 45 pounds.

9. The method of claim 1, further comprising performing manual distraction on the skeletally mature subject's skeletal system.

10. The method of claim 9, wherein the manual distraction on the skeletally mature subject's skeletal system reduces the skeletally mature subject's Cobb angle by at least about 50%.

11. The method of claim 1, wherein the scoliosis treatment device is configured to apply a constant distraction force between the first and second locations on the skeletally mature subject's skeletal system.

12. The method of claim 1, wherein the scoliosis treatment device is configured to apply a periodically changing distraction force between the first and second locations on the skeletally mature subject's skeletal system.

13. The method of claim 1, further comprising strengthening at least a portion of at least one of the first and second locations on the skeletally mature subject's skeletal system.

14. The method of claim 13, wherein the strengthening at least a portion of at least one of the first and second locations on the skeletally mature subject's skeletal system comprises performing a prophylactic vertebroplasty.

15. The method of claim 13, wherein the strengthening at least a portion of at least one of the first and second locations on the skeletally mature subject's skeletal system comprises performing a prophylactic kyphoplasty.

16. The method of claim 13, wherein the strengthening at least a portion of at least one of the first and second locations on the skeletally mature subject's skeletal system comprises treating a surface of one or more screws used for fixation of the scoliosis treatment device to the first and second locations on the skeletally mature subject's skeletal system using at least one of a biologic material that promotes bone growth and a surface finish that improves bone adhesion.

17. A method of treating scoliosis in a skeletally mature subject having a Cobb angle greater than zero, the method comprising:
 non-invasively actuating a scoliosis treatment device secured to first and second locations on a skeletally mature subject's skeletal system using an external adjustment device comprising least two rotating magnets generating a first magnetic field and a second magnetic field, wherein the scoliosis treatment device comprises a first portion, a second portion moveably mounted relative to the first portion, and an adjustment device comprising a rotationally mounted magnetic element and being configured to change at least one of a distraction force and a distance between the first and second locations on the skeletally mature subject's skeletal system, wherein the scoliosis treatment device is configured to noninvasively change the Cobb angle of the skeletally mature subject from an initial Cobb angle to a final Cobb angle through actuation by the external adjustment device.

18. The method of claim 17, wherein the initial Cobb angle is more than about 40°.

19. The method of claim 17, wherein the initial Cobb angle is more than about 100°.

20. The method of claim 17, wherein the initial Cobb angle is greater than the final Cobb angle.

21. The method of claim 17, wherein, following a single non-invasive adjustment, the Cobb angle is reduced by at least about 50% of the initial Cobb angle.

22. The method of claim 21, wherein, following a single non-invasive adjustment, the Cobb angle is reduced by at least about 15% of the initial Cobb angle.

23. The method of claim 17, wherein the scoliosis treatment device is configured to apply a periodically changing distraction force between the first and second locations on the skeletally mature subject's skeletal system.

24. The method of claim 17, further comprising non-invasively actuating the scoliosis treatment device secured to first and second locations on a skeletally mature subject's skeletal system at least a second time.

25. A method of treating scoliosis in a skeletally mature subject having a Cobb angle greater than zero, the method comprising:
 supplying a scoliosis treatment device configured to be secured to first and second locations on the skeletally mature subject's skeletal system, the scoliosis treatment device comprising a first portion, a second portion moveably mounted relative to the first portion, and an adjustment device comprising a rotationally mounted magnetic element and being configured to change at least one of a distraction force and a distance between the first and second locations on the skeletally mature subject's skeletal system, wherein the scoliosis treatment device is configured to be non-invasively actuated by an external adjustment device comprising at least two rotating magnets generating a first magnetic field and a second magnetic field, wherein the scoliosis treatment device is configured to noninvasively change the Cobb angle of the skeletally mature subject from an initial Cobb angle to a final Cobb angle through actuation by the external adjustment device.

26. The method of claim 25, wherein the initial Cobb angle is more than about 40°.

27. The method of claim 25, wherein the initial Cobb angle is more than about 100°.

28. The method of claim 25, wherein the initial Cobb angle is greater than the final Cobb angle.

29. The method of claim 25, wherein the scoliosis treatment device is configured to apply a periodically changing distraction force between the first and second locations on the skeletally mature subject's skeletal system.

30. The method of claim 25, wherein, following a single non-invasive adjustment, the Cobb angle is reduced by at least about 50% of the initial Cobb angle.

31. The method of claim 30, wherein, following a single non-invasive adjustment, the Cobb angle is reduced by at least about 15% of the initial Cobb angle.

32. A method of treating scoliosis in a skeletally mature subject having a Cobb angle greater than zero, the method comprising:
supplying a scoliosis treatment device configured to be secured to first and second locations on the skeletally mature subject's skeletal system, the scoliosis treatment device comprising a first portion, a second portion moveably mounted relative to the first portion, and an adjustment device comprising a rotationally mounted magnetic element and being configured to change at least one of a distraction force and a distance between the first and second locations on the skeletally mature subject's skeletal system, wherein the scoliosis treatment device is configured to be non-invasively actuated; and
supplying an external adjustment device configured to non-invasively actuate the scoliosis treatment device, the external adjustment device comprising at least two rotating magnets generating a first magnetic field and a second magnetic field, wherein the scoliosis treatment device is configured to noninvasively change the Cobb angle of the skeletally mature subject from an initial Cobb angle to a final Cobb angle through actuation by the external adjustment device.

33. The method of claim 32, wherein the initial Cobb angle is more than about 40°.

34. The method of claim 32, wherein the initial Cobb angle is more than about 100°.

35. The method of claim 32, wherein the initial Cobb angle is greater than the final Cobb angle.

36. The method of claim 32, wherein, following a single non-invasive adjustment, the Cobb angle is reduced by at least about 50% of the initial Cobb angle.

37. The method of claim 36, wherein, following a single non-invasive adjustment, the Cobb angle is reduced by at least about 15% of the initial Cobb angle.

38. The method of claim 32, wherein the scoliosis treatment device is configured to apply a periodically changing distraction force between the first and second locations on the skeletally mature subject's skeletal system.

* * * * *